US011229633B2

(12) United States Patent
Hinsby et al.

(10) Patent No.: US 11,229,633 B2
(45) Date of Patent: Jan. 25, 2022

(54) ARIMOCLOMOL FORMULATION

(71) Applicant: Orphazyme A/S, Copenhagen (DK)

(72) Inventors: Anders Mørkeberg Hinsby, Hellerup (DK); Thomas Kirkegaard Jensen, Rødovre (DK); Gert Mads Bolwig, Charlottenlund (DK); Carlos Roberto Camozzi, Basel (CH)

(73) Assignee: Orphazyme A/S, Copenhagen N (DK)

( * ) Notice: Subject to any disclaimer, the term of this patent is extended or adjusted under 35 U.S.C. 154(b) by 0 days.

(21) Appl. No.: 16/826,733

(22) Filed: Mar. 23, 2020

(65) Prior Publication Data
US 2020/0261437 A1 Aug. 20, 2020

Related U.S. Application Data

(62) Division of application No. 15/511,094, filed as application No. PCT/DK2015/050275 on Sep. 15, 2015, now Pat. No. 10,709,700.

(30) Foreign Application Priority Data

Sep. 15, 2014 (DK) .............................. PA201470566

(51) Int. Cl.
| A61K 31/4545 | (2006.01) |
| A61K 9/50 | (2006.01) |
| A61K 9/16 | (2006.01) |
| A61K 9/00 | (2006.01) |
| A61K 9/20 | (2006.01) |
| A61K 9/28 | (2006.01) |

(52) U.S. Cl.
CPC ........ *A61K 31/4545* (2013.01); *A61K 9/0053* (2013.01); *A61K 9/1617* (2013.01); *A61K 9/1694* (2013.01); *A61K 9/2009* (2013.01); *A61K 9/2013* (2013.01); *A61K 9/2054* (2013.01); *A61K 9/2059* (2013.01); *A61K 9/28* (2013.01); *A61K 9/5026* (2013.01); *A61K 9/5042* (2013.01); *A61K 9/5047* (2013.01); *A61K 9/5078* (2013.01)

(58) Field of Classification Search
CPC .............. A61K 31/4545; A61K 9/0053; A61K 9/1694; A61K 9/5078; A61P 13/12; A61P 3/00; A61P 3/10; A61P 43/00; A61P 9/12
See application file for complete search history.

(56) References Cited

U.S. PATENT DOCUMENTS

| 5,133,974 | A | * | 7/1992 | Paradissis ............ A61K 9/5078 424/451 |
| 5,348,945 | A | | 9/1994 | Berberian et al. |
| 5,830,464 | A | | 11/1998 | Srivastava |
| 5,948,646 | A | | 9/1999 | Srivastava |
| 5,985,270 | A | | 11/1999 | Srivastava |
| 6,007,821 | A | | 12/1999 | Srivastava et al. |
| 6,139,841 | A | | 10/2000 | Srivastava |
| 6,187,312 | B1 | | 2/2001 | Srivastava |
| 6,375,953 | B1 | | 4/2002 | Srivastava et al. |
| 6,384,029 | B1 | | 5/2002 | Jednakovits et al. |
| 6,403,095 | B1 | | 6/2002 | Srivastava et al. |
| 6,475,490 | B1 | | 11/2002 | Srivastava et al. |
| 6,649,628 | B1 | | 11/2003 | Kurthy et al. |
| 6,653,326 | B1 | | 11/2003 | Vigh et al. |
| 6,855,802 | B1 | | 2/2005 | Triebel et al. |
| 7,070,785 | B2 | | 7/2006 | Lehner et al. |
| 7,125,843 | B2 | | 10/2006 | DeFrees et al. |
| 7,126,002 | B2 | | 10/2006 | Urogdi et al. |
| 7,148,239 | B2 | | 12/2006 | Vigh et al. |
| 7,326,574 | B2 | | 2/2008 | Boux et al. |
| 7,361,655 | B2 | | 4/2008 | Csakai et al. |
| 7,384,936 | B2 | | 6/2008 | Csakai et al. |
| 7,396,681 | B1 | | 7/2008 | Multhoff |
| 7,517,948 | B2 | | 4/2009 | Multhoff |
| 7,550,457 | B2 | | 6/2009 | Csakai et al. |
| 7,691,849 | B2 | | 4/2010 | Csakai et al. |
| 7,745,465 | B2 | | 6/2010 | Vigh et al. |
| 7,750,050 | B2 | | 7/2010 | Schuchman et al. |
| 9,289,472 | B2 | * | 3/2016 | Jensen ................... A61K 38/47 |
| 9,662,375 | B2 | * | 5/2017 | Jensen ............... A61K 31/4545 |
| 9,884,058 | B2 | * | 2/2018 | Jensen ................... A61K 38/17 |
| 2001/0034042 | A1 | | 10/2001 | Srivastava |
| 2002/0006410 | A1 | | 1/2002 | Lukacs et al. |
| 2002/0035072 | A1 | | 3/2002 | Fan et al. |
| 2002/0037290 | A1 | | 3/2002 | Armen |

(Continued)

FOREIGN PATENT DOCUMENTS

| EP | 0751957 | 9/1995 |
| EP | 2145896 | 1/2010 |

(Continued)

OTHER PUBLICATIONS

Balogh et al.; The hyperfluidization of mammalian cell membranes acts as a signal to initiate the heat shock protein response. FEBS Journal 272 (2005) 6077-6086.

Botzler et al.; Synergistic effects of heat and ET-18-OCH3 on membrane expression of hsp70 and lysis of leukemic K562 cells. Experimental Hematology 27 (1999) 470-478.

Brunk et al.: Lysosomal involvement in apoptosis. Redox Rep. 2001; 6(2):91-7.

Brunk et al.: Photo-oxidative disruption of lysosomal membranes causes apoptosis of cultured human fibroblasts. Free Radical Biology & Medicine, vol. 23, No. 4, pp. 616-626, 1997.

Chung et al.; HSP72 protects against obesity-induced insulin resistance. PNAS Feb. 5, 2008 vol. 105, No. 5, 1739-1744.

(Continued)

*Primary Examiner* — Mark V Stevens
(74) *Attorney, Agent, or Firm* — Cooley LLP; Ivor R. Elrifi; Heidi A. Erlacher

(57) ABSTRACT

The present invention relates to a pharmaceutical formulation which provides for extended release of an active pharmaceutical ingredient selected from N-[2-hydroxy-3-(1-piperidinyl)-propoxy]-pyridine-1-oxide-3-carboximidoyl chloride, its stereoisomers and the acid addition salts thereof.

16 Claims, 12 Drawing Sheets

(56) References Cited

U.S. PATENT DOCUMENTS

| | | |
|---|---|---|
| 2002/0039583 A1 | 4/2002 | Subjeck et al. |
| 2002/0095135 A1 | 7/2002 | Meeker et al. |
| 2002/0119163 A1 | 8/2002 | Srikumaran |
| 2002/0127219 A1 | 9/2002 | Okkels et al. |
| 2002/0127718 A1 | 9/2002 | Kuppner et al. |
| 2002/0156250 A1 | 10/2002 | Wallen et al. |
| 2002/0172682 A1 | 11/2002 | Srivastava |
| 2002/0192230 A1 | 12/2002 | Srivastava |
| 2003/0012794 A1 | 1/2003 | Srivastava et al. |
| 2003/0035808 A1 | 2/2003 | Srivastava |
| 2003/0073094 A1 | 4/2003 | Young et al. |
| 2003/0129196 A1 | 7/2003 | Srivastava |
| 2003/0203846 A1 | 10/2003 | Srivastava et al. |
| 2003/0216315 A1 | 11/2003 | Nicchitta et al. |
| 2003/0236300 A1 | 12/2003 | Caplan et al. |
| 2004/0022796 A1 | 2/2004 | Srivastava |
| 2004/0047876 A1 | 3/2004 | Srivastava |
| 2005/0048608 A1 | 3/2005 | Chan et al. |
| 2005/0112640 A1 | 5/2005 | Davidson et al. |
| 2005/0153906 A1 | 7/2005 | Bedwell et al. |
| 2005/0202044 A1 | 9/2005 | Mizzen et al. |
| 2005/0267020 A1 | 12/2005 | Faure et al. |
| 2006/0009520 A1 | 1/2006 | Tall et al. |
| 2006/0089302 A1 | 4/2006 | Abulafia-Lapid et al. |
| 2006/0093612 A1 | 5/2006 | Srivastava |
| 2006/0264609 A1 | 11/2006 | Lehner et al. |
| 2006/0270833 A1 | 11/2006 | Henot et al. |
| 2007/0231337 A1 | 10/2007 | Multhoff |
| 2008/0009516 A1 | 1/2008 | Wustman |
| 2008/0014191 A1 | 1/2008 | Balch et al. |
| 2008/0019915 A1 | 1/2008 | Hadida-Ruah et al. |
| 2008/0026012 A1 | 1/2008 | Podack et al. |
| 2008/0039400 A1 | 2/2008 | Van Eden et al. |
| 2008/0039497 A1* | 2/2008 | Greensmith ............ A61P 25/14 514/318 |
| 2008/0132450 A1 | 6/2008 | Lee et al. |
| 2008/0161258 A1 | 7/2008 | Henning et al. |
| 2008/0227813 A1 | 9/2008 | Barber |
| 2008/0305084 A1 | 12/2008 | Podsakoff et al. |
| 2009/0163500 A1 | 6/2009 | Lingwood et al. |
| 2009/0203065 A1 | 8/2009 | Gehman et al. |
| 2009/0203605 A1 | 8/2009 | Segatori et al. |
| 2009/0208524 A1 | 8/2009 | Srivastava et al. |
| 2009/0227572 A1* | 9/2009 | Barber ................ A61K 31/165 514/229.2 |
| 2009/0233917 A1 | 9/2009 | Barber |
| 2009/0298857 A1 | 12/2009 | Chiosis et al. |
| 2009/0318343 A1 | 12/2009 | Garigapati et al. |
| 2010/0004277 A1 | 1/2010 | Bulawa et al. |
| 2010/0087490 A1 | 4/2010 | Young |
| 2010/0130730 A1 | 5/2010 | Garigapati et al. |
| 2010/0168016 A1 | 7/2010 | Ackerman et al. |
| 2010/0196279 A1 | 8/2010 | Lockhart |
| 2010/0221225 A1 | 9/2010 | Byrne et al. |
| 2010/0266571 A1 | 10/2010 | Lockhart et al. |
| 2010/0317690 A1 | 12/2010 | Kawamura et al. |
| 2010/0329985 A1 | 12/2010 | Van Eden et al. |
| 2011/0027254 A1 | 2/2011 | Daniel et al. |
| 2011/0028403 A1 | 2/2011 | Le Poole et al. |
| 2011/0081428 A1 | 4/2011 | Lithgow et al. |
| 2011/0105560 A1 | 5/2011 | Wustman |
| 2011/0110938 A1 | 5/2011 | Chiu et al. |
| 2011/0123512 A1 | 5/2011 | Prahlad et al. |
| 2011/0286993 A1 | 11/2011 | Jensen et al. |
| 2012/0115908 A1 | 5/2012 | Greensmith et al. |
| 2013/0230506 A1 | 9/2013 | Jensen et al. |
| 2013/0259875 A1* | 10/2013 | Somera-Molina ...... A61P 21/00 424/173.1 |
| 2014/0080769 A1 | 3/2014 | Platt et al. |
| 2014/0242162 A1 | 8/2014 | Diederich et al. |
| 2015/0126551 A1 | 5/2015 | Greensmith et al. |
| 2015/0284472 A1 | 10/2015 | Sardi et al. |
| 2020/0085812 A1 | 3/2020 | Jensen et al. |

FOREIGN PATENT DOCUMENTS

| | | |
|---|---|---|
| EP | 2318032 | 4/2012 |
| EP | 2484371 | 8/2012 |
| EP | 2659904 A1 | 11/2013 |
| EP | 2481400 B1 | 6/2014 |
| WO | WO-1997016439 | 5/1997 |
| WO | WO-1999/13799 | 3/1999 |
| WO | WO-2000/35914 A1 | 6/2000 |
| WO | WO-2000050403 | 8/2000 |
| WO | WO-200117554 | 3/2001 |
| WO | WO-200134184 | 5/2001 |
| WO | WO-200152877 | 7/2001 |
| WO | WO-200152890 | 7/2001 |
| WO | WO-200234777 | 5/2002 |
| WO | WO-2003026653 A1 | 4/2003 |
| WO | WO-2003049692 | 6/2003 |
| WO | WO-2003/061684 | 7/2003 |
| WO | WO-2003086452 | 10/2003 |
| WO | WO-2005/041965 A1 | 5/2005 |
| WO | WO-2005/102269 A2 | 11/2005 |
| WO | WO-2005/102272 A2 | 11/2005 |
| WO | WO-2005120558 | 12/2005 |
| WO | WO-2006/015943 A2 | 2/2006 |
| WO | WO-2007041285 | 4/2007 |
| WO | WO-2007/150064 | 12/2007 |
| WO | WO-2008021210 | 2/2008 |
| WO | WO-2008112525 | 9/2008 |
| WO | WO-2008117026 | 10/2008 |
| WO | WO-2008/132707 A1 | 11/2008 |
| WO | WO-2009095452 | 8/2009 |
| WO | WO-2009100037 | 8/2009 |
| WO | WO-20091 41627 | 11/2009 |
| WO | WO-2009137721 | 11/2009 |
| WO | WO-2009137796 | 11/2009 |
| WO | WO-2009/155936 A1 | 12/2009 |
| WO | WO-2009155936 | 12/2009 |
| WO | WO-2010015816 | 2/2010 |
| WO | WO-2010022461 | 3/2010 |
| WO | WO-2010053655 | 5/2010 |
| WO | WO-2010086418 | 8/2010 |
| WO | WO-2010/092112 | 8/2010 |
| WO | WO-2010102988 | 9/2010 |
| WO | WO-2010116141 | 10/2010 |
| WO | WO-2010148253 | 12/2010 |
| WO | WO-2011019763 | 2/2011 |
| WO | WO-2011075686 | 6/2011 |
| WO | WO-2011/95973 A1 | 8/2011 |
| WO | WO-2012/012656 A2 | 1/2012 |
| WO | WO-2012/072082 A1 | 6/2012 |
| WO | WO-2013/006076 A1 | 1/2013 |
| WO | WO-2013/148333 A1 | 10/2013 |
| WO | WO-2014/071282 A1 | 5/2014 |
| WO | WO-2016/041561 A1 | 3/2016 |

OTHER PUBLICATIONS

Daugaard et al., "The heat shock protein 70 family: Highly homologous proteins with overlapping and distinct functions," Febs Letters, Elsevier, Amsterdam, vol. 581, No. 19, Jul. 31, 2007, pp. 3702-3710.

Ferlinz et al.; Stimulation of lysosomal sphingomyelin degradation by sphingolipid activator proteins. Chemistry and Physics of Lipids 102 (1999) 35-43.

Fleshner & Johnson: Endogenous extra-cellular heat shock protein 72: Releasing signal(s) and function. Int. J. Hyperthermia, Aug. 2005; 21(5):457-471.

Gehrmann et al.; Differential Up-Regulation of Cytosolic and Membrane-Bound Heat Shock Protein 70 in Tumor Cells by Anti-Inflammatory Drugs. Clinical Cancer Research vol. 10, 3354-3364, May 15, 2004.

Gehrmann et al.; Effects of Antineoplastic Agents on Cytoplasmic and Membrane-Bound Heat Shock Protein 70 (Hsp70) Levels. Biol. Chem., vol. 383, pp. 1715-1725, Nov. 2002.

Gehrmann et al.; The therapeutic implications of clinically applied modifiers of heat shock protein 70 (Hsp70) expression by tumor cells. Cell Stress and Chaperones (2008) 13: 1-10.

(56) References Cited

OTHER PUBLICATIONS

Harada et al.: Heat shock proteins and the antitumor T cell response. Biotherapy 10: 229-235, 1998.
Kalmar & Greensmith; Activation of the heath shock response in a primary cellular model of motoneuron neurodegeneration—evidence for neuroprotective and neurotoxic effects. Cellular & Molecular Biology Letters vol. 14 (2009) pp. 319-335.
Kalmar et al.; Late stage treatment with arimoclomol delays disease progression and prevents protein aggregation in the SOC1G93A mouse model of ALS. Journal of Neurochemistry 2008, 107, 339-350.
Kalmar et al.; Upregulation of Heat Shock Proteins Rescues Motoneurons from Axotomy-lnduced Cell Death in Neonatal Rats. Experimental Neurology 176, 87-97 (2002).
Kieran et al., Treatment with arimoclomol, a coinducer of heat shock proteins, delays disease progression in ALS mice, Nature Medicine, 10(4): 402-45, Apr. 2004.
Kirkegaard et al., Hsp70 stabilizes lysosomes and reverts Niemann-Pick disease-associated lysosomal pathology, Nature Letters, 463: 549-554, Jan. 28, 2010.
Kirkegaard-Sorenson et al.; Interaction between Hsp70 and bis(monoacylglycero)phosphate stabilizes lysosomes and promotes cell survival. APMIS, 116( 5): 436-437, 2008.
Kirkegaard-Sorenson; Hsp70 binding to BMP—A novel mechanism for cellular protection. Dep. of Apoptosis, Danish Cancer Society, Feb. 2008. PhD Thesis. University of Copenhagen, Faculty of Health Sciences.
Kobayashi et al.: A lipid associated with the antiphospholipid syndrome regulates endosome structure and function. Nature Letters, vol. 392 Mar. 12, 1998.
Kolzer et al.: Interactions of acid sphingomyelinase and lipid bilayers in the presence of the tricyclic antidepressant desipramine. FEBS Letters 559 (2004) 96-98.
Ng et al., Predicting deleterious amino acid substitutions. Genome Res. 2001 11: 863-874.
Nylandsted et al.: Heat shock protein 70 promotes cell survival by inhibiting lysosomal membrane permeabilization. J. Exp. Med. vol. 200, No. 4, Aug. 16, 2004 425-435.
Ohtsuka et al.; Inducers and co-inducers of molecular chaperones. Int. J. Hyperthermia, Dec. 2005; 21(8): 703-711.
Sambrook et al., Molecular Cloning, A Laboratory Manual, Cold Spring Harbor, Laboratory Press (1998), 1.101-1.104.
Tavaria et al.: A hitchhiker's guide to the human Hsp70 family. Mini-review. Cell stress & Chaperones (1996) 1 (1), 23-28.
Tidwell et al.: Administration of Hsp70 in vivo inhibits motor and sensory neuron degeneration. Cell Stress & Chaperones (2004) 9(1), 88-98.
Tytell & Hooper; Heat Shock proteins: new keys to the development of cytoprotective therapies. Expert Opin Ther Targets, Apr. 2001;5(2):267-87.
Tytell: Release of heat shock proteins (Hsps) and the effects of extracellular Hsps on neural cells and tissues. Int J Hypothermia, Aug. 2005; 21(5): 445-455.
Torok et al.; Heat shock protein coinducers with No. effect on protein denaturation specifically modulate the membrane lipid phase. PNAS Mar. 18, 2003, vol. 100, No. 6, 3131-3136.
Vigh et al., Bimocolomol: A nontoxic, hydroxylamine derivative with stress protein-inducing activity and cytoprotective effects, Nature Medicine, 3(10): 1150-54, Oct. 1997.
Vigh et al.; Can the stress protein response be controlled by membrane-lipid therapy? Trends in Biochemical Sciences vol. 32 No. 8 (2007).
Wei et al.: Inhibition of proliferation and induction of apoptosis by abrogation of heat-shock protein (HSP) 70 expression in tumor cells. Cancer Immunol. Immunother. (1995) 40:73-78.
Yu et al.: Retinal uptake of intravitreally injected Hsc/Hsp70 and its effects on susceptibility to light damage. Molecular Vision 2001; 7:48-56.
Zhu Yunxiang et al. "Dexmethasone-mediated up-regulation of the mannose receptor improves the delivery of recombinant glucocerebrosidase to Gaucher macrophages," The Journal of Pharmacology and Experimental Therapeutics, Feb. 2004, vol. 308, No. 2, pp. 705-711.
Communication Pursuant to Article 94(3) EPC for Application No. 09768858.4 dated Jul. 26, 2011.
Du, W. et al., Cell Growth Inhibition by Farnseyltransferase Inhibitors is Mediated by Gain of Geranylgeranylated RhoB, Molecular and Cellular Biology, 19(3): 1831-40, Mar. 1999.
Prendergast, G. et al., Farnesyltransferase Inhibition Causes Morphological Reversion of ras-Transformed Cells by a Complex Mechanism that Involves Regulation of the Actin Cytoskeleton, Molecular and Cellular Biology, 14(6): 4193-4202, Jun. 1994.
Balabanov, S. et al., Quantitative proteomics analysis of BMS-214662 effects on CD34 positive cells from chronic myeloid leukaemia patients, Proteomics, 13: 153-68, 2013.
Mazieres, J. et al., Perspectives on farnesyl transferase inhibitors in cancer therapy, Cancer Letters, 206: 159-67, 2004.
Porcu, G. et al., A yeast-based genomic strategy highlights the cell protein networks altered by FTase inhibitor peptidomimetics. Molecular Cancer, 9: 197, 2010.
Jaatela, M. et al., Emerging Role of Heat Shock Proteins in Biology and Medicine, Annals of Medicine, 24: 249-258, 1992.
Goni, F. et al., Sphingomyelinases: enzymology and membrane activity, Federation of European Biochemical Societies, 531: 38-46, 2002.
Yenari, M. et al., The neuroprotective potential of heat shock protein 70 (HSP70), Molecular Medicine Today, 5: 525-31, 1999.
Horvath, I. et al., Membrane-associated stress proteins: More than simply chaperones, Biochimica et Biophysica Acta, 1778: 1653-64, 2008.
Simons, K. et al., Jamming the Endosomal System: Lipid Rafts and Lysosomal Storage Diseases, Trends in Cell Biology, 10: 459-62, 2000.
Hu, W. et al., Proteomic identification of heat shock protein 70 as a candidate target for enhancing apoptosis induced by farnesyl transferase inhibitor, Proteomics, 3: 1904-11, 2003.
Keeling et al., Gentamicin-mediated suppression of Hurler syndrome stop mutations restores a low level of alpha-L-iduronidase activity and reduces lysosomal glycosaminoglycan accumulation, Human Molecular Genetics, 10: 291-99, 2001.
Meikle et al., Effect of lysosomal storage on bis(monoacylglycero)phosphate, Biochem J., 411: 71-78, 2008.
Voellmy et al., Isolation and functional analysis of a human 70,000-dalton heat shock protein gene segment, Proc. Natl. Acad. Sci. USA, 82: 4949-53, 1985.
Wu, et al., Structure and expression of the human gene ancoding major heat shock protein HSP70, Mol. Cell. Biol., 5(2): 330-41, 1985.
Bruening, W. et al., Up-regulation of protein chaperones preserves viability of cells expressing toxic Cu/Zn-superoxide dismutase mutants associated with amyotrophic lateral sclerosis, Journal of Neurochemistry, 72: 693-99, 1999.
Horváth, I. et al., Cell biology: Stability in times of stress, Nature, 463(7280): 436-438, 2010.
Kalmar, B. et al., The effect of treatment with BRX-220, a coinducer of heat shock proteins, on sensory fibers of the rat following peripheral nerve injury, Exp. Neurol., 184: 636-647, 2003.
Polakowski, J. et al., Bimoclomol elevates heat shock protein 70 and cytoprotects rat neonatal cardiomyocytes, European Journal of Pharmacology, 435: 73-77, 2002.
Rakonczay, Z. et al., Nontoxic heat shock protein coinducer BRX-220 protects against acute pancreatitis in rats, Free Radical Biology and Medicine, 32(12): 1283-1292, 2002.
Kabakov, A. et al., Pharmacological attenuation of apoptosis in reoxygenated endothelial cells, Cellular and Molecular Life Sciences, 61: 3076-86, 2004.
Hallows, J. et al., p35/p25 Is Not Essential for Tau and Cytoskeletal Pathology or Neuronal Loss in Niemann-Pick Type C Disease, The Journal of Neuroscience, 26: 2738-2744, 2006.
Patterson, M. et al., Miglustat for treatment of Niemann-Pick C disease: a randomised controlled study, Lancet Neurology, 6: 765-772, 2007.

(56) References Cited

OTHER PUBLICATIONS

Lubbers, N. et al., Oral bimoclomol elevates heat shock protein 70 and reduces myocardial infarct size in rats, European Journal of Pharmacology, 435: 79-83, 2002.

Winchester, B. et al., The molecular basis of lysosomal storage disease, Biochemical Society Transactions, 28: 150-54, 2000.

Au, Q. et al., High-content image-based screening for small-molecule chaperone amplifiers in heat shock, Journal of Biomolecular Screening, 13(19): 953-959, 2008.

Parfitt, D. et al., The heat-shock response co-inducer arimoclomol protects against retinal degeneration in rhodopsin retinitis pigmentosa, Cell Death and Disease, 5: 1-10, 2014.

Cohen, F. et al., Therapeutic approaches to protein-misfolding diseases, Nature, 426:905-909, 2003.

Freeman, B. et al., The human cytosolic molecular chaperones hsp90 (hsc70) and hdj-1 have distinct roles in recognition of a non-native protein and protein refolding, The European Molecular Biology Journal, 15: 2969-79, 1996.

Cudkowicz, M. et al., Arimoclomol at Dosages up to 300 Mg/day is Well Tolerated and Safe in Amyotrophic Lateral Sclerosis, Muscle & Nerve, pp. 837-844, Jul. 2008.

Lepist, E. et al., Contribution of the organic anion transporter OAT2 to the renal active tubular secretion of creatinine and mechanism for serum creatinine elevations caused by cobicistat, Kidney International, 86: 350-357, 2014.

https://adisinsight.springer.com/drugs/800016664 (Year: 2019).

Roth, A. et al., Interaction between Hsp70 and bis(monoacylglycero)phosphate stabilizes lysosomes and promotes cell survival, APMIS, 116: 437, 2008.

Balwani, M. et al., Gaucher disease: When molecular testing and clinical presentation disagree—the novel c.1226A.>G(p.N370S)-RecNcil allele, J Inherit Metab Dis, 34:789-793, 2011.

Bergamin, N. et al., A human neuronal model of Niemann Pick C disease developed from stem cells isolated from patient's skin, Orphanet Journal of Rare Diseases, 8(1): 34, 2013.

Bligh, E. et al., A Rapid Method of Total Lipid Extraction And Purification, Canadian Journal of Biochemistry and Physiology, 37(8): 911-917, 1959.

Blom, T. et al., FTY720 Stimulates 27-Hydroxycholesterol Production and Confers Atheroprotective Effects in Human Primary Macrophages, Circ. Res. 106: 720-729, 2010.

Boyum, A., Separation of white blood cells, Nature, 204: 793-794 1964.

Gan-Or. Z. et al., Differential effects of severe vs mild GBA mutations on Parkinson disease, Neurology, 84: 880-887, Mar. 3, 2015.

Ingemann, L. et al., Lysosomal storage diseases and the heat shock response: convergences and therapeutic opportunities, Journal of Lipid Research, 55: 2198-2210, May 16, 2014.

Mahalka, A. et al., Human heat shock protein 70 (Hsp70) as a peripheral membrane protein, Biochimica et Biophysica Acta, 1838: 1344-1361, Jan. 28, 2014.

McNeill et al., Ambroxol improves lysosomal biochemistry in glucocerebrosidase mutation-linked Parkinson disease cells, Brain, 137: 1481-1495, Feb. 25, 2014.

Mu, T., et al., Chemical and biological approaches synergize to ameliorate protein-folding diseases, Cell, 134: 769-81, Sep. 5, 2008.

Sardi, S. et al., CNS expression of glucocerebrosidase corrects alpha-synuclein pathology and memory in a mouse model of Gaucher-related synucleinopathy, PNAS, 108(29): 12101-12106, Jul. 19, 2011.

Sardi, S. et al., Augmenting CNS glucocerebrosidase activity as a therapeutic strategy for parkinsonism and other Gaucher-related synucleinopathies, PNAS, 110(9): 3537-3542, Feb. 26, 2013.

Wang, S. et al., ABCA1 and nascent HDL biogenesis, Biofactors 40(6): 547-554, Nov. 2014.

Witte, M. Et al., Ultrasensitive in situ visualization of active glucocerebrosidase molecules, Nature Chemical Biology, 6(12): 907-913, Oct. 31, 2010.

Xing, B. et al., Hsp70 plays an important role in high-fat diet induced gestational hyperglycemia in mice, J Physiol Biochem, 71: 649-658, Aug. 29, 2015.

Lanka, V. et al., Arimoclomol: a potential therapy under development for ALS, Expert Opin. Investig. Drugs, 18(12):1907-1918, 2009.

Ibrahim, M. et al., Employing Compritol in a Mixed Matrix for Sustaining Chlorpheniramine Maleate Release: Kinetic Study, Digest Journal of Nanomaterials and Biostructures, 8(2): 737-746, Apr.-Jun. 2013.

Mehvar, R., The Relationship Among Pharmacokinetic Parameters: Effects of Altered Kinetics on the Drug Plasma Concentration-Time Profiles, American Journal of Pharmaceutical Education, 68(2), Article 36, pp. 1-9, 2004.

Mathialagan, S. et al., Evaluation of Renal Transporter Inhibition Using Creatinine as a Substrate In Vitro to Assess the Clinical Risk of Elevated Serum Creatinine, Journal of Pharmaceutical Sciences, 106: 2535-2541, 2017.

Mehvar, The relationship among pharmacokinetic parameters: Effects of altered kinetics on the drug plasma concentration-time profiles. Am J Pharm Edu 2004; 68 (2) Art 36.

Schapira, A., Glucocerebrosidase and Parkinson disease: Recent advances, Molecular and Cellular Neuroscience, 66:37-42, 2015.

Liscic, R., Molecular basis of ALS and FTD: implications for translational studies, Arhiv za Hihijenu Rada i Toksikologiju,, 66: 285-290, Dec. 1, 2015.

Rademakers et al., The Role of Tau (MAPT) in Frontotemporal Dementia and Related Tauopathies. Human Mutation, 24:277-295, 2004.

Gotzl, J. et al., Impaired Protein Degradation in FTLD and Related Disorders, Aging Res Rev. Dec. 32:122-139, 2016.

Malik, B. et al., Co-induction of the heat shock response ameliorates disease progression in a mouse model of human spinal and bulbar muscular atrophy: implications for therapy, Brain, 136:926-43, 2013.

Custer, S. et al., Transgenic Mice Expressing Mutant Forms VCP/p97 Recapitulate the Full Spectrum of IBMPFD Including Degeneration in Muscle, Brain and Bone, Hum Mol Genet. 1;19(9):1741-55, 2010.

Ahmed, M. et al., Targeting Protein Homeostasis in Sporadic Inclusion Body Myositis, Sci. Tran Med; 8(331), 331ra41. Mar. 2016, 13 pages.

Ratti, A. et al., Physiological Functions and Pathobiology of TDP-43 and FUS/TLS Proteins, J Neurochem;138 Suppl 1:95-111, Aug. 2016.

Li, Q. et al., The cleavage pattern of TDP-43 determines its rate of clearance and cytotoxicity, Nature Communications 6; 6183, Jan. 29, 2015.

Yoshiyama.Y. et al ., Frontotemporal Dementia and Tauopathy, Curr Neurol Neurosci Rep.; 1(5):413-21, Sep. 2001.

Tanida, I. et al., LC3 and Autophagy, Methods Mol Biol, 445, 77-88, 2008.

Lee, E. et al., Gains or losses: molecular mechanisms of TDP43-mediated neurodegeneration, Nat Rev Neurosci, 13: 38-50, Nov. 30, 2011.

Tresse, E., et al., VCP/p97 is essential for maturation of ubiquitin-containing autophagosomes and this function is impaired by mutations that cause IBMPFD, Autophagy, 6: 217-227, 2010.

Higuchi, M. et al., Axonal Degeneration Induced by Targeted Expression of Mutant Human Tau in Oligodendrocytes of Transgenic Mice That Model Glial Tauopathies, J Neurosci., 25 (41): 9434-9443, Oct. 2005.

Jeong, H. et al., Brain Inflammation and Microglia: Facts and Misconceptions, Exp Neurobiol., 22(2): 59-67, Jun. 2013.

Monahan, Z. et al., Stress granules at the intersection of autophagy and ALS, Brain Res.1649(Pt B): 189-200, Oct. 15, 2016.

Ito, D. et al., RNA Binding Proteins and the Pathological Cascade in ALS/FTD Neurodegeneration, Sci Transl Med., 9(415): eeah5436, 2017.

Alberti, S. et al.,Granulostasis: Protein Quality Control of RNP Granules, Front. Mol. Neurosci., 10:84, Mar. 27, 2017, 14 pages.

(56) References Cited

OTHER PUBLICATIONS

Fog, C. et al., The heat shock protein amplifier arimoclomol improves refolding, maturation and lysosomal activity of glucocerebrosidase, EBioMedicine, https://doi.org/10.1016/j.ebiom.2018.11.037.

Matsumoto et al., Manual of Pharmacology, Mar. 20, 1989, p. 117-118.

English language translation of 2019/06/04 JPO Office Action for corresponding Japanese Patent Application 2017-533689 including an explanation of the relevance of Matsumoto et al., Manual of Pharmacology, dated Mar. 20, 1989, p. 117-118.

Machado, P. et al. (Jun. 13, 2013) "Safety and Tolerability of Arimoclomol in Patients with Sporadic Inclusion Body Myositis: A Randomised, Double-Blind, Placebo-Controlled, Phase IIA Proof-of-Concept Trial" Ann Rheum Dis, 72:A164, Abstract LB0002; doi: 10.1136/annrheumdrs-2013-eular.527, 1 page.

\* cited by examiner

ARIMOCLOMOL FORMULATION

REFERENCE TO RELATED APPLICATIONS

This application is a divisional of U.S. patent application Ser. No. 15/511,094, filed Mar. 14, 2017, now U.S. Pat. No. 10,709,700, issued on Jul. 14, 2020, which is a U.S. national phase application of PCT/DK2015/050275, filed Sep. 15, 2015, which claims priority from Denmark patent application No. PA 201470566, filed Sep. 15, 2014. The entire content of all of which is incorporated herein by reference.

FIELD OF THE INVENTION

The present invention relates to a pharmaceutical formulation providing for extended release of arimoclomol and accompanying reduced Cmax, reduced inhibition of OCT2 and/or reduced effect on serum creatinine levels.

BACKGROUND OF THE INVENTION

Arimoclomol is a heat shock protein amplifier currently under evaluation in the treatment of paediatric lysosomal storage disorders and amyotrophic lateral sclerosis (ALS).

The physical properties of arimoclomol make the drug somewhat difficult to handle. The drug substance is white in appearance, light and fluffy. Arimoclomol is hygroscopic i.e. it absorbs moisture (water molecules) from its surroundings. Arimoclomol has a relatively short plasma half-life (2-4 hours) and multiple daily dosing is currently required.

Arimoclomol is to date administered as powder-filled, coated gelatine capsules (arimoclomol capsules). The arimoclomol capsules are of immediate-release (IR) type.

Arimoclomol has been tested in healthy human volunteers and no maximum tolerated dose has been reached. A total of 261 subjects have been exposed to oral single ascending or repeated doses of arimoclomol ranging from 50 to 800 mg in seven concluded Phase I trials and two concluded Phase II trials, and is found to be safe and well-tolerated.

In the single- and multiple-dose Phase I studies, slight and reversible increases in serum creatinine levels were observed in a number of volunteers but these were not considered to be clinically significant (see e.g. Cudkowicz et al., Muscle & Nerve, July 2008, p. 837-844).

SUMMARY OF THE INVENTION

It is an aspect of the present invention to provide an extended-release formulation of arimoclomol.

By retarding the release of arimoclomol following the ingestion of an oral dose, the extended-release formulation elicits a relatively lower peak blood concentration (Cmax) of arimoclomol relative to the total exposure provided as expressed by the area under the curve (AUC). During the course of repeated oral administration, the extended-release formulation therefore reduces the peak-to-trough ratio of the arimoclomol blood concentration. This provides several advantages for clinical use compared to a conventional immediate-release oral formulation:

By supporting less frequent dosing, the extended-release formulation of arimoclomol will support higher treatment compliance in home-based care as well as regularity of scheduling in managed care situations.

By improving the physical flow characteristics, the extended-release formulation will be more amenable to presentation in sachets or pouches, which may be desirable for dosing by mixing with drinks or foodstuff, as well as aided by feeding tubes. This will present a marked improvement for the treatment of patients with dysphagia or other neuromuscular impairments.

In the event that some patients experience untoward effects of immediate-release oral dosing, the extended-release formulation may provide a treatment option that could support a relatively higher arimoclomol exposure whilst limiting untoward effects compared to an immediate-release formulation.

OCT2 is a renal organic cation transporter involved in creatinine secretion (see e.g. Lepist et al., Kidney International (2014) 86, 350-357). OCT2 (Organic cation transporter 2) is also known as Solute carrier family 22 member 2 and is expressed from SLC22A2 (UniProt S22A2_HUMAN).

It is shown herein that arimoclomol is an inhibitor of the renal uptake transporter OCT2—the half-maximal inhibition ($IC_{50}$) of arimoclomol was defined at 10 µM for OCT2. Thus, shortly after human oral dosing higher than 400 mg to there may be transient and reversible inhibitory activity of this transporter at Cmax.

To address the observed OCT2-inhibition and the slight and reversible increase in serum creatinine, an extended-release formulation of arimoclomol is provided.

The formulation potentially also has value for patients who receive additional medications, which medications per se affect serum creatinine levels, and/or which medications depend at least partly on OCT2 for clearance and excretion.

This formulation can be of further value for example for paediatric patients and patients presenting with increased basal levels of serum creatinine; including patients with kidney disease or decreased renal function, and patients with diabetes mellitus or hypertension.

The present formulations have an extended release to allow for reduced daily dosing. The present formulations are furthermore easy to swallow with acceptable organoleptic characteristics. Also, the present formulation provides for more efficient manufacturing, achieving a batch within the specifications and allowing for better standardisation.

It is an aspect of the present invention to provide a pharmaceutical formulation comprising an active pharmaceutical ingredient (API) selected from N-[2-hydroxy-3-(1-piperidinyl)-propoxy]-pyridine-1-oxide-3-carboximidoyl chloride, its stereoisomers and the acid addition salts thereof, wherein said formulation provides for extended release of said active pharmaceutical ingredient.

In one embodiment the present pharmaceutical formulations provide for a lower Cmax, a higher Tmax, a reduced inhibition of the OCT2 transporter, and/or a reduced effect on serum creatinine as compared these parameters following administration of an immediate-release formulation or bolus IV injection of the same active pharmaceutical ingredient.

DETAILED DESCRIPTION OF THE INVENTION

Figure 1:
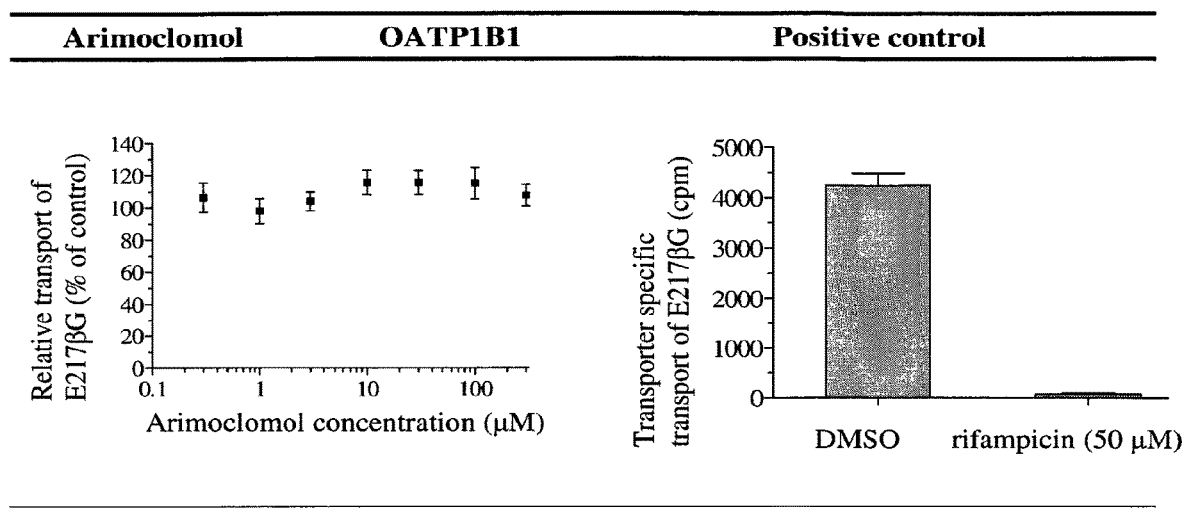
FIG. 1 Inhibition of OATP1B1-mediated probe substrate transport by arimoclomol in the uptake transporter inhibition assay.

The present invention provides for extended-release (ER) formulations of arimoclomol with improved pharmacokinetics, standardised manufacturing, and higher patient compliance. Extended release, sustained release, delayed release and controlled release are used interchangeably herein.

The present invention in one aspect provides a pharmaceutical formulation comprising an active pharmaceutical ingredient (API) selected from N-[2-hydroxy-3-(1-piperidinyl)-propoxy]-pyridine-1-oxide-3-carboximidoyl chloride (arimoclomol), its stereoisomers and the acid addition salts thereof, wherein said formulation provides for extended release of said active pharmaceutical ingredient.

The terms pharmaceutical formulation, pharmaceutically safe formulation and pharmaceutically acceptable formulation are used interchangeably herein.

In one embodiment said pharmaceutical formulation comprises said API in a pharmaceutically effective or pharmaceutically active amount.

In one embodiment said formulation comprises an inner matrix and at least one outer coating.

In another embodiment said formulation comprises extended-release granules. In one embodiment said extended-release granules are produced by hot melt extrusion (HME) and optionally size reduction.

In one embodiment the present pharmaceutical formulation reduces Cmax, increases Tmax, reduces inhibition of OCT2 and/or reduces effect on serum creatinine levels; as compared to an equivalent amount of N-[2-hydroxy-3-(1-piperidinyl)-propoxy]-pyridine-1-oxide-3-carboximidoyl chloride (arimoclomol), its stereoisomers and the acid addition salts thereof administered by an immediate release oral dosage form and/or by bolus IV injection.

Extended or controlled release technology is a mechanism used in formulations to dissolve slowly and release a drug over time. Extended-release formulations may be taken less frequently than immediate-release formulations, and they keep steadier levels of the drug in the bloodstream.

In one embodiment the term providing for extended release of an active pharmaceutical ingredient according to the invention means that the API is dissolved or released from the pharmaceutical formulation over time.

Extended-release drugs may be formulated so that the active ingredient is embedded in a matrix of insoluble substance(s) such that the dissolving drug must find its way out through the holes in the matrix. Some drugs are enclosed in polymer-based tablets with a laser-drilled hole on one side and a porous membrane on the other side. Stomach acids push through the porous membrane, thereby pushing the drug out through the laser-drilled hole. In time, the entire drug dose releases into the system while the polymer container remains intact, to be excreted later through normal digestion. In some formulations, the drug dissolves into the matrix, and the matrix physically swells to form a gel, allowing the drug to exit through the gel's outer surface. Micro-encapsulation also produces complex dissolution profiles; through coating an active pharmaceutical ingredient around an inert core, and layering it with insoluble substances to form a microsphere a more consistent and replicable dissolution rate is obtained—in a convenient format that may be mixed with other instant release pharmaceutical ingredients, e.g. into any two piece gelatin capsule.

A dosage form is a mixture of active drug components and non-drug components. The pharmaceutical formulation according to the present invention is in one embodiment a dosage form, such as an oral dosage form. In one embodiment, said dosage form is a solid dosage form, such as a tablet. In one embodiment, said dosage form is a granular dosage form, such as comprising extended-release granules.

In one embodiment said pharmaceutical formulation is orally available. In one embodiment said formulation is a solid dosage form. In one embodiment said formulation is an orally available solid dosage form.

A tablet is a pharmaceutical dosage form comprising a mixture of (an) active substance(s) and excipient(s), pressed or compacted into a solid dose. Tablets are simple and convenient to use. They provide an accurately measured dosage of the active ingredient(s) in a convenient portable package. Manufacturing processes and techniques can provide tablets special properties, for example, extended release or fast dissolving formulations. Tablets are easy to weigh out, and have high physical integrity.

Mini-tablets are tablets with a diameter ≤3 mm, and represent a new trend in solid dosage form design, with the main goal of overcoming some therapeutic obstacles such as impaired swallowing and polypharmacy therapy, and also offering some therapeutic benefits such as dose flexibility and combined release patterns.

In one embodiment a mini-tablet according to the invention is a tablet with a diameter less than or equal to (≤) 3 mm, such as ≤2.5 mm, for example ≤2 mm, such as ≤1.5 mm, for example about 1 mm. In one embodiment a mini-tablet according to the invention is a tablet with a diameter of 1 to 1.5 mm, such as 1.5 to 2 mm, for example 2 to 2.5 mm, such as 2.5 to 3 mm.

In one embodiment a micro-tablet according to the invention is a tablet with a diameter less than or equal to (≤) 1 mm, such as ≤0.9 mm, for example ≤0.8 mm, such as ≤0.7 mm, for example ≤0.6 mm, such as ≤0.5 mm, for example ≤0.4 mm, such as ≤0.3 mm, for example ≤0.3 mm, such as ≤0.1 mm. In one embodiment a mini-tablet according to the invention is a tablet with a diameter of 0.1 to 0.2 mm, such as 0.2 to 0.3 mm, for example 0.3 to 0.4 mm, such as 0.4 to 0.5 mm, such as 0.5 to 0.6 mm, for example 0.6 to 0.7 mm, such as 0.7 to 0.8 mm, for example 0.8 to 0.9 mm, such as 0.9 to ≤1 mm.

In the manufacture of pharmaceuticals, encapsulation refers to a range of dosage forms in a relatively stable shell known as a capsule, allowing them to, for example, be taken orally or be used as suppositories. There are two main types of capsules:

Hard-shelled capsules made in two halves: a lower-diameter "body" that is filled and then sealed using a higher-diameter "cape"; and soft-shelled capsules, primarily used for oils and for active ingredients that are dissolved or suspended in oil. Both types of capsules are made from aqueous solutions of gelling agents including animal protein mainly gelatin and plant polysaccharides or their derivatives like carrageenans and modified forms of starch and cellulose. Other ingredients can be added to the gelling agent solution like plasticizers such as glycerin and/or sorbitol to decrease the capsule's hardness, coloring agents, preservatives, disintegrants, lubricants and surface treatment.

The pharmaceutical formulation according to the present invention in one embodiment comprises an active pharmaceutical ingredient (API) as detailed herein elsewhere, as well as one or more excipients.

An excipient is a pharmacologically inactive (or chemically inactive) substance formulated with the active ingredient of a medication. Excipients are commonly used to bulk up formulations that contain potent active ingredients (thus often referred to as "bulking agents," "fillers," or "diluents"), to allow convenient and accurate dispensation of a drug substance when producing a dosage form.

In embodiment, the pharmaceutical formulation according to the present invention comprises one or more excipients. Said one or more excipients may act as a solid carrier, diluent, flavouring agent, solubilizer, lubricant, glidant, suspending agent, binder, filler, preservative, anti-adherent, wetting agent, tablet disintegrating agent, sorbent, and/or an encapsulating/coating material.

The present pharmaceutical formulation in one embodiment comprises at least one excipient in order to obtain a suitable formulation with the desired extended release characteristics.

In one embodiment, the pharmaceutical formulation according to the present invention comprises one or more release-controlling excipients.

Extended-Release Formulation

It is an aspect to provide a pharmaceutical formulation comprising
an active pharmaceutical ingredient (API) selected from N-[2-hydroxy-3-(1-piperidinyl)-propoxy]-pyridine-1-oxide-3-carboximidoyl chloride, its stereoisomers and the acid addition salts thereof, and
a release-controlling excipient,
wherein said formulation provides for extended release of said active pharmaceutical ingredient.

In one embodiment said pharmaceutical formulation is a dosage form, such as an oral dosage form (orally available dosage form).

In one embodiment the pharmaceutical formulation is an extended release dosage form of N-[2-hydroxy-3-(1-piperidinyl)-propoxy]-pyridine-1-oxide-3-carboximidoyl chloride, its stereoisomers and the acid addition salts thereof, comprising
a pharmaceutically effective amount of N-[2-hydroxy-3-(1-piperidinyl)-propoxy]-pyridine-1-oxide-3-carboximidoyl chloride, its stereoisomers and the acid addition salts thereof, and
a release-controlling excipient.

Cmax is a term used in pharmacokinetics to refer to the maximum (or peak) serum concentration that a drug achieves in a specified compartment or test area of the body after the drug has been administrated and prior to the administration of a second dose. Tmax is a term used in pharmacokinetics to describe the time at which the Cmax is observed.

In one embodiment the pharmaceutical formulation is capable of one or more of
reducing Cmax as compared to the Cmax for an equivalent amount of N-[2-hydroxy-3-(1-piperidinyl)-propoxy]-pyridine-1-oxide-3-carboximidoyl chloride, its stereoisomers and the acid addition salts thereof administered by an immediate release oral dosage form and/or by bolus IV injection,
reducing Cmax with 1 or 2 daily dosages as compared to the Cmax for an equivalent amount of N-[2-hydroxy-3-(1-piperidinyl)-propoxy]-pyridine-1-oxide-3-carboximidoyl chloride, its stereoisomers and the acid addition salts thereof administered by immediate release oral dosage forms and/or by bolus IV injections three times a day,
eliciting a relatively lower peak blood concentration (Cmax) of arimoclomol relative to the total exposure provided as expressed by the area under the curve (AUC),
reducing the peak-to-trough ratio of the arimoclomol blood (or serum) concentration,
maintaining arimoclomol exposure while reducing the peak plasma level (Cmax)
maintaining arimoclomol exposure and/or AUC with fewer administrations (such as once or twice a day), while reducing the peak plasma level (Cmax)
increasing Tmax as compared to the Tmax for an equivalent amount of N-[2-hydroxy-3-(1-piperidinyl)-propoxy]-pyridine-1-oxide-3-carboximidoyl chloride, its stereoisomers and the acid addition salts thereof administered by an immediate release oral dosage form and/or by bolus IV injection,
reducing inhibition of OCT2 as compared to the inhibition of OCT2 for an equivalent amount of N-[2-hydroxy-3-(1-piperidinyl)-propoxy]-pyridine-1-oxide-3-carboximidoyl chloride, its stereoisomers and the acid addition salts thereof administered by an immediate release oral dosage form and/or by bolus IV injection,
reducing the effect on serum creatinine levels as compared to the effect on serum creatinine levels for an equivalent amount of N-[2-hydroxy-3-(1-piperidinyl)-propoxy]-pyridine-1-oxide-3-carboximidoyl chloride, its stereoisomers and the acid addition salts thereof administered by an immediate release oral dosage form and/or by bolus IV injection, reducing the effect on renal creatinine clearance as compared to the effect on renal creatinine clearance for an equivalent amount of N-[2-hydroxy-3-(1-piperidinyl)-propoxy]-pyridine-1-oxide-3-carboximidoyl chloride, its stereoisomers and the acid addition salts thereof administered by an immediate release oral dosage form and/or by bolus IV injection, achieving a Cmax that is lower than the half-maximal inhibition (IC50) of the active pharmaceutical ingredient for OCT2.

In one embodiment the pharmaceutical formulation have an extended release to allow for reduced daily dosing, or reduced frequency of dosing. In preferred embodiment the formulation is administered once or twice a day, compared to the conventional IR formulation which is administered 3 times a day.

In one embodiment the pharmaceutical formulation is administered to achieve a an arimoclomol exposure or Cmax that prevents arimoclomol from i) inhibiting renal transporters, ii) inhibiting OCT2 and/or iii) inhibiting creatinine clearance.

The term 'a release-controlling excipient' implies the presence of at least one, or one or more, release-controlling excipients.

A release-controlling excipient according to the present invention is an excipient or agent which provides for extended release of an API selected from N-[2-hydroxy-3-(1-piperidinyl)-propoxy]-pyridine-1-oxide-3-carboximidoyl chloride, its stereoisomers and the acid addition salts thereof.

A release-controlling excipient according to the present invention in one embodiment controls the release rate of an API selected from N-[2-hydroxy-3-(1-piperidinyl)-propoxy]-pyridine-1-oxide-3-carboximidoyl chloride, its stereoisomers and the acid addition salts thereof from a pharmaceutical formulation.

The release-controlling excipient according to the present invention in one embodiment controls the release rate of an API selected from N-[2-hydroxy-3-(1-piperidinyl)-propoxy]-pyridine-1-oxide-3-carboximidoyl chloride, its stereoisomers and the acid addition salts thereof, to reduce Cmax,
reduce inhibition of OCT2,
reduce effect on serum creatinine levels, and/or
increase Tmax, as compared to an equivalent amount of N-[2-hydroxy-3-(1-piperidinyl)-propoxy]-pyridine-1-oxide-3-carboximidoyl chloride, its stereoisomers and the acid addition salts thereof administered by an immediate release oral dosage form and/or by bolus IV injection.

Also provided is a method of administering an amount of an API selected from N-[2-hydroxy-3-(1-piperidinyl)-propoxy]-pyridine-1-oxide-3-carboximidoyl chloride, its stereoisomers and the acid addition salts thereof to a patient in need thereof by extended release such that the maximum serum concentration after administration of N-[2-hydroxy-3-(1-piperidinyl)-propoxy]-pyridine-1-oxide-3-carboximidoyl chloride, its stereoisomers and the acid addition salts thereof, (Cmax) is reduced as compared to the Cmax of an equivalent amount thereof administered by an immediate release oral dosage form and/or by bolus IV injection, the time for the serum concentration to reach its maximum after administration of N-[2-hydroxy-3-(1-piperidinyl)-propoxy]-pyridine-1-oxide-3-carboximidoyl chloride, its stereoisomers and the acid addition salts thereof, (Tmax), is increased as compared to Tmax for an equivalent amount thereof administered by an immediate release oral dosage form and/or by bolus IV injection, the inhibition of OCT2 after administration of N-[2-hydroxy-3-(1-piperidinyl)-propoxy]-pyridine-1-oxide-3-carboximidoyl chloride, its stereoisomers and the acid addition salts thereof, is reduced as compared to the inhibition of OCT2 for an equivalent amount thereof administered by an immediate release oral dosage form and/or by bolus IV injection, the effect on serum creatinine levels after administration of N-[2-hydroxy-3-(1-piperidinyl)-propoxy]-pyridine-1-oxide-3-carboximidoyl chloride, its stereoisomers and the acid addition salts thereof, is reduced as compared to the effect on serum creatinine levels for an equivalent amount thereof administered by an immediate release oral dosage form and/or by bolus IV injection.

In one embodiment the effect on serum creatinine levels of N-[2-hydroxy-3-(1-piperidinyl)-propoxy]-pyridine-1-oxide-3-carboximidoyl chloride (arimoclomol), its stereoisomers and the acid addition salts thereof is a slight increase in serum creatinine levels.

In one embodiment the pharmaceutical formulation provides for a lower Cmax of the API as compared to an immediate-release formulation of the API.

In one embodiment the pharmaceutical formulation provides for a higher Tmax of the API as compared to an immediate-release formulation of the API.

In one embodiment the pharmaceutical formulation provides for a reduced inhibition of the OCT2 transporter by the API (arimoclomol), as compared to an immediate-release formulation of the API.

In one embodiment the pharmaceutical formulation of the present invention reduces or avoids the arimoclomol-induced inhibition of OCT2; which reduced OCT2 inhibition in one embodiment reduces the risk of adversely affecting the clearance, excretion and/or circulating half-life of additional medications, especially medications which are substrates for the OCT2 transporter.

In one embodiment the pharmaceutical formulation provides for a reduced effect on serum creatinine by the API, as compared to an immediate-release formulation of the API.

In one embodiment the pharmaceutical formulation provides for a Cmax of less than 15 µM, for example less than 10 µM, such as less than 9 µM, for example less than 8 µM, such as less than 7 µM, for example less than 6 µM, such as less than 5 µM, for example less than 4 µM, such as less than 3 µM, for example less than 2 µM, such as less than 1 µM.

In one embodiment the pharmaceutical formulation provides for a Cmax of 1 to 2 µM, for example 2 to 3 µM, such as 3 to 4 µM, for example 4 to 5 µM, such as 5 to 6 µM, for example 6 to 7 µM, such as 7 to 8 µM, for example 8 to 9 µM, such as 9 to 10 µM, for example 10 to 11 µM, such as 11 to 12 µM, for example 12 to 13 µM, such as 13 to 14 µM, for example 14 to 15 µM.

In a preferred embodiment the pharmaceutical formulation provides for a Cmax of less than or equal to 10 µM.

In a preferred embodiment the pharmaceutical formulation provides for a Cmax of less than or equal to 10 µM, achieved with less frequent daily dosing, such as achieved by once daily or twice daily dosing.

In one embodiment Cmax is reduced by a factor of at least 10%, such as a factor of at least 20%, such as a factor of at least 30%, such as a factor of at least 40%, such as a factor of at least 50%, such as a factor of at least 60%, such as a factor of at least 70%, such as a factor of at least 80%, such as a factor of at least 90%, such as a factor of at least 100%.

In one embodiment Cmax is reduced by a factor of 10 to 20%, such as a factor of 20 to 30%, such as a factor of 30 to 40%, such as a factor of 40 to 50%, such as a factor of 50 to 60%, such as a factor of 60 to 70%, such as a factor of 70 to 80%, such as a factor of 80 to 90%, such as a factor of 90 to 100%.

In one embodiment Tmax is increased by a factor of at least 10%, such as a factor of at least 20%, such as a factor of at least 30%, such as a factor of at least 40%, such as a factor of at least 50%, such as a factor of at least 60%, such as a factor of at least 70%, such as a factor of at least 80%, such as a factor of at least 90%, such as a factor of at least 100%, such as a factor of at least 125%, such as a factor of at least 150%, such as a factor of at least 175%, such as a factor of at least 200%, such as a factor of at least 250%.

In one embodiment Tmax is increased by a factor of 10 to 20%, such as a factor of 20 to 30%, such as a factor of 30 to 40%, such as a factor of 40 to 50%, such as a factor of 50 to 60%, such as a factor of 60 to 70%, such as a factor of 70 to 80%, such as a factor of 80 to 90%, such as a factor of 90 to 100%, such as a factor of 100 to 125%, such as a factor of 125 to 150%, such as a factor of 150 to 175%, such as a factor of 175 to 200%, such as a factor of 200 to 225%, such as a factor of 225 to 250%.

In one embodiment the inhibition of OCT2 is reduced by a factor of at least 10%, such as a factor of at least 20%, such as a factor of at least 30%, such as a factor of at least 40%, such as a factor of at least 50%, such as a factor of at least 60%, such as a factor of at least 70%, such as a factor of at least 80%, such as a factor of at least 90%, such as a factor of at least 100%.

In one embodiment the inhibition of OCT2 is reduced by a factor of 10 to 20%, such as a factor of 20 to 30%, such as a factor of 30 to 40%, such as a factor of 40 to 50%, such as a factor of 50 to 60%, such as a factor of 60 to 70%, such as a factor of 70 to 80%, such as a factor of 80 to 90%, such as a factor of 90 to 100%.

The pharmaceutical formulation in one embodiment has a dissolution rate of 85% of the API released within 3 to 5 hours (medium), and in another embodiment of 85% API released after at least (≥) 6 hours, such as after at least 7, 8, 9 or 10 hours (slow).

The dissolution rate describes how fast the compound is released from the formulation into solution. The rate of dissolution can be expressed by the Noyes-Whitney Equation or the Nernst and Brunner equation.

In one embodiment the pharmaceutical formulation provides for a dissolution rate of 10 to 90% of the API released at 3 to 5 hours, such as 10 to 20%, 20 to 30, 30 to 40, 40 to 50, 50 to 60, 60 to 70, 70 to 75, 75 to 80, 80 to 85 or 85 to 90% of the API released within 3 to 5 hours, such as within 3 hours, within 4 hours, or within 5 hours.

In one embodiment the pharmaceutical formulation provides for a dissolution rate of 10 to 90% of the API released within 6 hours, such as 10 to 20%, 20 to 30, 30 to 40, 40 to 50, 50 to 60, 60 to 70, 70 to 75, 75 to 80, 80 to 85 or 85 to 90% of the API released within ≥6 hours, such as within ≥7 hours, ≥8 hours, ≥9 hours, ≥10 hours, ≥11 hours, ≥12 hours, ≥13 hours, ≥14 hours, ≥15 hours, ≥16 hours, ≥17 hours, ≥18 hours.

Tablets and Spheres

The present invention in one aspect provides a pharmaceutical formulation comprising an active pharmaceutical ingredient selected from N-[2-hydroxy-3-(1-piperidinyl)-propoxy]-pyridine-1-oxide-3-carboximidoyl chloride (arimoclomol), its stereoisomers and the acid addition salts thereof, wherein said formulation comprises an inner matrix and at least one outer coating, wherein said formulation provides for extended release of said active pharmaceutical ingredient.

In one embodiment said formulation is selected from the group consisting of a tablet, a mini-tablet, a micro-tablet, a coated tablet, a coated mini-tablet, a coated micro-tablet, a sphere and a coated sphere.

In one embodiment the pharmaceutical formulation of the invention is used as a single-unit oral dosage form (also known as non-divided formulation). In another embodiment the pharmaceutical formulation of the invention is used as a multiple-unit oral dosage form (also known as divided formulation). A multiple-unit oral dosage form is a distinct drug product packaged together, in the present context for example mini-tablets within a capsule.

In one embodiment the inner matrix of the formulation comprises the active pharmaceutical ingredient. In these embodiments the formulation may be selected from a coated tablet, a coated mini-tablet and a coated micro-tablet.

In one embodiment the formulation is selected from a coated tablet, a coated mini-tablet and a coated micro-tablet, wherein the inner matrix (or the tablet) comprises the API, and wherein the outer coating does not comprise the API.

In one embodiment the outer coating of the formulation comprises the active pharmaceutical ingredient. In these embodiments the formulation may be a coated sphere (drug-loaded sphere).

In one embodiment said formulation is a coated sphere, wherein the inner matrix (sphere substrate) does not comprise the API, and the outer coating comprises the API.

In one embodiment the outer coating of the coated sphere comprises one or more individual layers, wherein the innermost layer immediately surrounding the sphere comprises the API.

In one embodiment the pharmaceutical formulation of the present invention is contained within a capsule, such as to provide a multiple-unit oral dosage form, such as a capsule comprising two or more formulation units or tablets/mini-tablets/spheres according to the invention. In one embodiment the capsule comprises or consists of gelatin. In one embodiment the capsule is a hard-shelled capsule, such as hard-capsule gelatin. In a further embodiment the capsule further comprises an outer coating.

In one embodiment the multiple-unit oral dosage form of the invention is a capsule comprising two or more formulation units according to the present invention, such as comprising 2 to 3, 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, 19 to 20, 20 to 21, 21 to 22, 22 to 23, 23 to 24, 24 to 25, 25 to 26, 26 to 27, 27 to 28, 28 to 29, 29 to 30, 30 to 35, 35 to 40, 40 to 45, 45 to 50, 50 to 55, 55 to 60, 60 to 65, 65 to 70, 70 to 75, 75 to 80, 80 to 85, 85 to 90, 90 to 95, 95 to 100 formulation units.

In one embodiment a formulation unit is selected from the group consisting of a coated mini-tablet, a coated micro-tablet and a coated sphere.

The number of formulation units within the capsule depends on the amount or concentration of API in each unit, and the individual characteristics of the patient to which the pharmaceutical formulation is to be administered, as the skilled person will acknowledge.

Oral Dosage Form—Tablet

In one embodiment the pharmaceutical formulation according to the invention comprises a matrix constituent, such as an inner matrix comprising the API, and optionally an outer coating. In one embodiment the inner matrix is a tablet, a mini-tablet or a micro-tablet, which tablet is optionally coated.

In one embodiment the pharmaceutical formulation according to the invention comprises at least one type of hydroxypropylmethylcellulose (HPMC) also known as hypromellose. HPMC is used as an excipient in oral tablet and capsule formulations, where, depending on the grade, it functions as a controlled release agent or release-controlling excipient to delay the release of a medicinal compound into the digestive tract. It is also used as a binder and as a component of tablet coatings.

In one embodiment the inner matrix of the present formulation comprises the API and one or more release-controlling excipients. In one embodiment the inner matrix further comprises one or more additional excipients such as fillers, binders and lubricants.

Release controlling excipients as used herein may be any release controlling excipient known to the skilled person. Release controlling excipients in one embodiment is an excipient selected from the group consisting of hydroxypropylmethylcellulose (HPMC), ethylcellulose (EC), methylcellulose, hydroxypropyl cellulose, hypromellose acetate succinate, hypromellose phthalate, cellulose acetate, glycerin monostearate, glyceryl monooleate, glyceryl palmitate, glyceryl behenate, hydrogenated vegetable oil, guar gum, polyvinyl alcohol, alginates, xanthan gum, carnauba wax, yellow wax, white wax, zein, carregeenan, carbomers and agar.

In one embodiment, the inner matrix further comprises a filler, such as a filler selected from the group consisting of calcium carbonate, calcium phosphates, calcium sulfate, cellulose, cellulose acetate, compressible sugar, dextrate, dextrin, dextrose, ethylcellulose, fructose, isomalt, lactitol, lactose, mannitol, magnesium carbonate, magnesium oxide, maltodextrin, microcrystalline cellulose (MCC), polydextrose, sodium alginate, sorbitol, talc and xylitol.

In one embodiment, the inner matrix further comprises a binder, such as a binder selected from the group consisting of acacia, alginic acid, carbomers, carboxymethylcellulose sodium, carrageenan, cellulose acetate phthalate, chitosan, copovidone, dextrate, dextrin, dextrose, ethylcellulose, gelatin, guar gum, hydroyethyl cellulose, hydroxyethylmethyl cellulose, hydroxypropyl cellulose, hydroxypropyl starch, hypromellose, methylcellulose, poloxamer, polydextrose, polyethylene oxide, povidone, sodium alginate, sucrose, starch, pregelatinized starch and maltodextrin.

In one embodiment, the inner matrix further comprises a lubricant, such as a lubricant selected from the group consisting of calcium stearate, glycerin monostearate, glyceryl behenate, glyceryl palmitostearate, hydrogenated castor oil, hydrogenated vegetable oil, magnesium lauryl sulfate, magnesium stearate, medium chain triglyceride, palmitic acid, polyethylene glycol, sodium lauryl sulfate, stearic acid, talc, silica and zinc stearate.

Any other excipients suitable for the purpose of the present invention and known to the skilled person are considered encompassed by the present invention.

Different grades of HPMC have different characteristics with respect to e.g. viscosity. Thus, different HPMCs will have different impacts on the release rates of the embedded API. Also, the amount of HPMC in the formulation, the hardness or degree of compression of the formulation into a tablet, as well as any potential coatings, will potentially impact the release rates of the API. The release rates may be determined by evaluating the dissolution profiles of the produced batches. In vitro drug dissolution data generated from dissolution testing experiments can be related to in vivo pharmacokinetic data by means of in vitro-in vivo correlations (IVIVC).

In one embodiment, the inner matrix comprises one or more excipients selected from the group consisting of hydroxypropylmethylcellulose (HPMC), starch, ethylcellulose (EC), microcrystalline cellulose (MCC), silica, magnesium stearate and stearic acid. In one embodiment, the inner matrix comprises at least one HPMC.

Chemically HPMC is mixed alkyl-hydroxyalkyl cellulose ether containing methoxyl and hydroxypropyl groups. HPMC is manufactured by the Dow Chemical Company under the trademark of Methocel. Methocel used for ER matrix applications utilizes two types of chemical substituent groups signified by either 'E' or 'K' designations. Methocel polymers are also graded based on their viscosity (in cps) of a 2% weight/volume aqueous solution at 20° C. Typical HPMC grades utilized for ER formulations range in viscosity from 50 to 100,000 cps at 20° C. and include Methocel E50 Premium LV, K100 Premium LV CR, K4M Premium CR, K15M Premium CR, K100M Premium CR, E4M Premium CR and E10M Premium CR.

In one embodiment the HPMC is a HPMC having a grade providing for a viscosity of 50 to 100,000 cps at 20° C. In one embodiment the HPMC is a high-viscosity grade HPMC or an ultra-high-viscosity grade HPMC. In one embodiment the HPMC is a HPMC allowing (or providing) for extended release.

In one embodiment the HPMC is selected from the group consisting of Methocel E50 Premium LV, K100 Premium LV CR, K4M Premium CR, K15M Premium CR, K100M Premium CR, E4M Premium CR, E10M Premium CR, K200M, E5 and E50.

The release-controlling excipient, such as HPMC, of the inner matrix is in one embodiment present in an amount of 20 to 50% w/w, such as 20 to 25% w/w, for example 25 to 30% w/w, such as 30 to 35% w/w, for example 35 to 40% w/w, such as 40 to 45% w/w, for example 45 to 50% w/w. In a particular embodiment, the release-controlling excipient such as HPMC is present in an amount of about 30% w/w, for example 35% w/w, such as about 40% w/w.

In one embodiment, the matrix comprises two or more release-controlling excipients, such as three or more release-controlling excipients.

In one embodiment, the inner matrix comprises one or more different types (viscosity-grades) of HPMC, such as 1, 2, 3, 4 or 5 types of HPMC. In one embodiment the inner matrix comprises a combination of HPMC polymers.

In one embodiment the inner matrix comprises a combination of HPMC with ionic, non-ionic and/or water-insoluble polymers.

In one embodiment the inner matrix comprises a combination of HPMC with one or more ionic polymers selected from the group consisting of sodium carboxymethylcellulose (na CMC), sodium alginate, polymers of acrylic acid or carbomers (carbopol 934, 940, 974P NF), enteric polymers such as polyvinyl acetate phthalate (PVAP), methacrylic acid copolymers (Eudragit L100 L 30D 55, S and FS 30 D), hypromellose acetate succinate (AQOAT HPMCAS) and xanthan gum.

In one embodiment the inner matrix comprises a combination of HPMC with one or more non-ionic polymers selected from the group consisting of HPC (hydroxypropyl cellulose) and PEO (POLYOX, Dow Chemical Company) in various molecular weight grades (from 100,000 to 7,000,000 da).

In one embodiment the inner matrix comprises a combination of HPMC with one or more water-insoluble polymers selected from the group consisting of ethylcellulose (e.g. ETHOCEL or Surrelease), cellulose acetate, methycrylic acid copolymers (e.g. Eudragit NE 30D), ammonio-methacrylate copolymers (e.g. Eudragit RL 100 or PO RS100) and polyvinyl acetate.

In one particular embodiment, HPMC is mixed with microcrystalline cellulose (MCC) to achieve a MCC/HPMC matrix. The second excipient, such as MCC, is in one embodiment present in an amount of 10 to 50% w/w, such as 10 to 15% w/w, for example 15 to 20% w/w, such as 20 to 25% w/w, for example 25 to 30% w/w, such as 30 to 35% w/w, for example 35 to 40% w/w, such as 40 to 45% w/w, for example 45 to 50% w/w MCC. The MCC is in a particular embodiment Avicel PH 101 or Avicel PH 102.

Microcrystalline cellulose is commercially available in different particle sizes and moisture grades which have different properties and applications. Avicel PH 101 has a nominal mean particle size of 50 microns while Avicel PH 102 has a nominal mean particle size of 100 microns. Both have a moisture content of <=5%

In one embodiment, the inner matrix further comprises starch, such as comprises starch in an amount of 5 to 30% w/w, such as 5 to 10% w/w, for example 10 to 15% w/w, such as 15 to 20% w/w, for example 20 to 25% w/w, such as 25 to 30% w/w starch. In a particular embodiment, starch is present in an amount of about 5% w/w, for example 10% w/w, such as about 15% w/w, for example 20% w/w. The starch is in a particular embodiment StarCap 1500.

In one embodiment, the inner matrix further comprises ethylcellulose (EC), suc as comprises EC in an amount of 5 to 30% w/w, such as 5 to 10% w/w, for example 10 to 15% w/w, such as 15 to 20% w/w, for example 20 to 25% w/w, such as 25 to 30% w/w EC. In a particular embodiment, EC is present in an amount of about 5% w/w, for example 10% w/w, such as about 15% w/w, for example 20% w/w. The EC is in a particular embodiment Ethocel Standard 7 Premium.

In one embodiment, the inner matrix further comprises silica, such as colloidal silica, wherein the silica in one embodiment is present in an amount of 0.05 to 1% w/w, such as 0.05 to 0.1, for example 0.1 to 0.2, such as 0.2 to 0.3, for example 0.3 to 0.4, such as 0.4 to 0.5, for example 0.5 to 0.6, such as 0.6 to 0.7, for example 0.7 to 0.8, such as 0.8 to 0.9, for example 0.9 to 1.0% w/w. In a particular embodiment, silica is present in an amount of about 0.2% w/w.

In one embodiment, the inner matrix further comprises magnesium stearate, wherein the magnesium stearate in one embodiment is present in an amount of 0.1 to 5% w/w, such as 0.1 to 0.5, for example 0.5 to 1.0, such as 1 to 2, for example 2 to 3, such as 3 to 4, for example 4 to 5% w/w. In a particular embodiment, magnesium stearate is present in an amount of about 1% w/w. The magnesium stearate is in a particular embodiment Ligamed MF-2-V.

In one embodiment, the inner matrix further comprises stearic acid, wherein the stearic acid in one embodiment is present in an amount of from 0.1 to 10% w/w, such as 0.1 to 0.5, for example 0.5 to 1.0, such as 1 to 2, for example 2 to 3, such as 3 to 4, for example 4 to 5, such as 5 to 6, for example 6 to 7, such as 7 to 8, for example 8 to 9, such as 9 to 10% w/w. In a particular embodiment, stearic acid is present in an amount of about 2% w/w.

In one embodiment the inner matrix is compressed to form a tablet with hardness of 10 to 50 kp (kilopond), such as 10 to 15 kp, for example 15 to 20 kp, such as 20 to 25 kp, for example 25 to 30 kp, such as 30 to 35 kp, for example 35 to 40 kp, such as 40 to 50 kp.

In one embodiment the inner matrix is compressed to form a tablet with a hardness of 15 to 80N (Newton), such as 15 to 20N, for example 20 to 25N, such as 25 to 30N, for example 30 to 35N, such as 35 to 40N, for example 40 to 45N, such as 45 to 50N, for example 50 to 55, such as 55 to 60N, for example 60 to 70N, such as 70 to 80N.

Coated Tablet

In one embodiment the pharmaceutical formulation according to the invention comprises a matrix constituent, such as an inner matrix comprising the API, and an outer coating. In one embodiment the outer coating does not comprise the active pharmaceutical ingredient.

In one embodiment the pharmaceutical formulation is a coated tablet, a coated mini-tablet or a coated micro-tablet.

The outer coating preferably aids in the extended release of the API comprised in the inner matrix. In one embodiment the outer coating is release-retardant.

When reference is made to 'outer coating' this may apply to one or more individual layers of the outer coating. In one embodiment the outer coating comprises one or more individual layers of coating.

In one embodiment the outer coating comprises one or more excipients. In one embodiment the outer coating comprises aqueous based ethylcellulose (EC) dispersion, such as Surrelease™. In one embodiment the outer coating comprises solvent based EC. In one embodiment the outer coating comprises aqueous based polymethacrylate based dispersion, such as Eudragit NE30D™. In one embodiment the outer coating comprises a film-forming excipient.

In one embodiment the formulation is coated until a certain gain in weight (w/w) is achieved. In one embodiment the formulation is coated to a 5% w/w weight gain, such as a 10% w/w weight gain, for example a 15% w/w weight gain, such as a 20% w/w weight gain, for example a 25% w/w weight gain, such as a 30% w/w weight gain, for example a 35% w/w weight gain, such as a 40% w/w weight gain. In one embodiment the formulation is coated to a weight gain of 5 to 40% w/w, such as 10 to 15% w/w, for example 15 to 20% w/w, such as 20 to 25% w/w, for example 25 to 30% w/w, such as 30 to 35% w/w, for example 35 to 40% w/w.

In one embodiment there is provided a pharmaceutical formulation comprising
  a. an inner matrix comprising an active pharmaceutical ingredient (API) selected from N-[2-hydroxy-3-(1-piperidinyl)-propoxy]-pyridine-1-oxide-3-carboximidoyl chloride, its stereoisomers and the acid addition salts thereof,
     wherein said matrix comprises at least one release-controlling excipient and optionally one or more additional excipients, and
  b. optionally an outer coating,
     wherein said formulation provides for extended release of said active pharmaceutical ingredient.

In one embodiment the inner matrix comprises 5 to 40% w/w of N-[2-hydroxy-3-(1-piperidinyl)-propoxy]-pyridine-1-oxide-3-carboximidoyl chloride, its stereoisomers and the acid addition salts thereof, such as 5 to 10, for example 10 to 15, such as 15 to 20, for example 20 to 25, such as 25 to 30, for example 30 to 35, such as 35 to 40% w/w.

In one embodiment the outer coating further comprises an outer seal coating. The outer seal coating is applied as the outermost layer.

Oral Dosage Form—Coated Sphere

The pharmaceutical formulation according to the invention in one embodiment comprises a matrix constituent, such as an inner matrix or sphere substrate, and an outer coating comprising one or more individual layers.

In one embodiment the present formulation is a coated sphere, wherein said coated sphere comprises a sphere substrate and an outer coating comprising one or more individual layers.

The outer coating of the coated sphere in one embodiment comprises one or more individual layers, such as two or more layers, such as three or more layers, such as four or more layers, such as five or more layers. In one embodiment the outer coating comprises 1 to 2, such as 2 to 3, for example 3 to 4, such as 4 to 5, for example 5 to 6 layers.

In one embodiment the inner matrix or sphere substrate does not comprise the active pharmaceutical ingredient. In one embodiment the outer coating comprises the active pharmaceutical ingredient. In one embodiment the innermost layer of the outer coating comprising two or more layers comprises the active pharmaceutical ingredient.

In one embodiment the API is deposited or coated on the surface of said inner matrix or sphere substrate to provide a drug layer, and said API-coated sphere is further coated with one or more additional layers.

Figure 13:
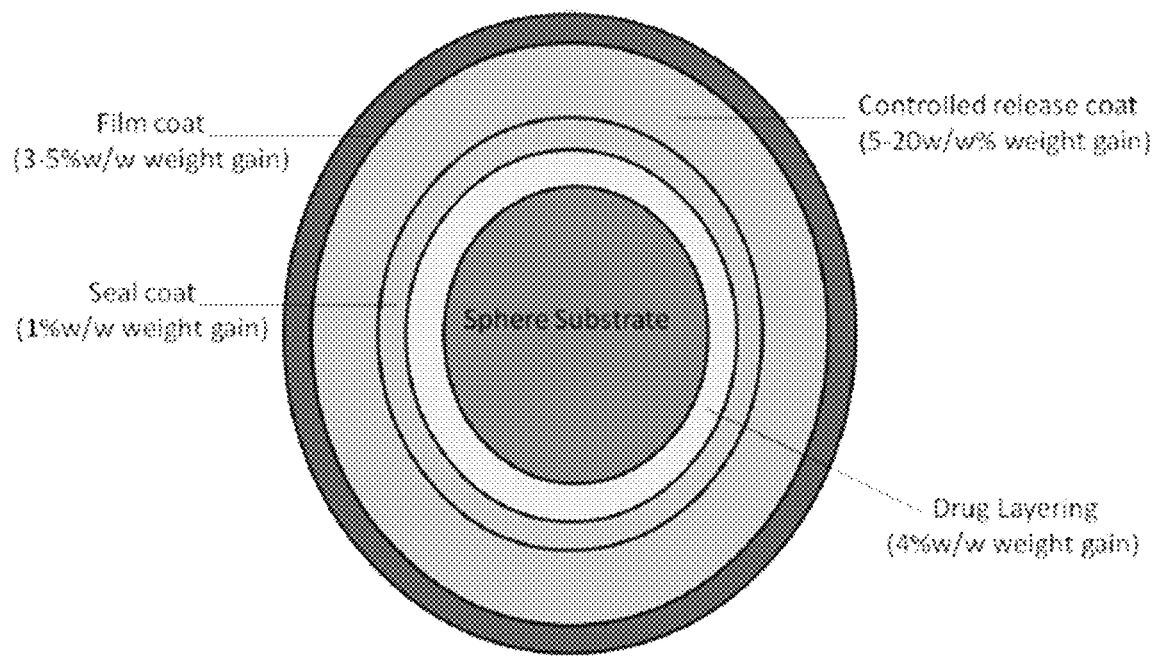
FIG. 13 Schematic overview of sphere composition.

In one embodiment the formulation of the invention comprises (from the inside and out): 1) a sphere substrate (or multiparticulate core), 2) a drug layer comprising the active pharmaceutical ingredient, 3) optionally a seal coat, 4) a controlled release coat, and 5) optionally a film coat. This is illustrated in FIG. 13.

In one embodiment the coated sphere comprises: 1) a sphere substrate, 2) a drug layer to 1 to 10% w/w weight gain, 3) optionally a seal coat to 0.1 to 5% w/w weight gain, 4) a controlled release coat to 5 to 20% w/w weight gain, and 5) optionally a film coat to 1 to 10% w/w weight gain.

In one embodiment the drug layer is applied to 1 to 10% w/w weight gain, such as 1 to 2, for example 2 to 3, such as 3 to 4, for example 4 to 5, such as 5 to 6, for example 6 to 7, such as 7 to 8, for example 8 to 9, such as 9 to 10% w/w weight gain. In one embodiment the drug layer is applied to about 1% w/w weight gain, such as 2, for example 3, such as 4, for example 5, such as 6, for example 7, such as 8, for example 9, such as about 10% w/w weight gain.

In one embodiment the seal coat is applied to 0.1 to 5% w/w weight gain, such as 0.1 to 0.5, for example 0.5 to 1, such as 1 to 2, for example 2 to 3, such as 3 to 4, for example 4 to 5% w/w weight gain. In one embodiment the seal coat is applied to about 0.1% w/w weight gain, such as 0.5, for example 1, such as 2, for example 3, such as 4, for example 5% w/w weight gain.

In one embodiment the controlled release coat is applied to 5 to 20% w/w weight gain, such as 5 to 6, for example 6 to 7, such as 7 to 8, for example 8 to 9, such as 9 to 10, for example 10 to 11, such as 11 to 12, for example 12 to 13, such as 13 to 14, for example 14 to 15, such as 15 to 16, for example 16 to 17, such as 17 to 18, for example 18 to 19, such as 19 to 20% w/w weight gain. In one embodiment the controlled release coat is applied to about 5% w/w weight gain, such as 6, for example 7, such as 8, for example 9, such as 10, for example 11, such as 12, for example 13, such as about 14, for example 15, such as 16, for example 17, such as 18, for example 19, such as about 20% w/w weight gain.

In one embodiment the film coat is applied to 1 to 10% w/w weight gain, such as 1 to 2, for example 2 to 3, such as 3 to 4, for example 4 to 5, such as 5 to 6, for example 6 to 7, such as 7 to 8, for example 8 to 9, such as 9 to 10% w/w weight gain. In one embodiment the film coat is applied to about 1% w/w weight gain, such as 2, for example 3, such as 4, for example 5, such as 6, for example 7, such as 8, for example 9, such as about 10% w/w weight gain.

In one embodiment the coated sphere comprises: 1) a sphere substrate, 2) a drug layer to 4% w/w weight gain, 3) a seal coat to 1% w/w weight gain, 4) a controlled release coat to 5 to 20% w/w weight gain, and 5) a film coat to 3 to 5% w/w weight gain.

In one embodiment the sphere substrate comprises or consists of sugar, such as a soluble sugar sphere, e.g. Suglets™.

In one embodiment the sphere substrate comprises or consists of an MCC sphere, such as an insoluble microcrystalline cellulose sphere, e.g. Vivapur™.

In one embodiment the sugar spheres are 1000/1180 μm in size.

In one embodiment the MCC spheres are 710-1000 μm in size.

In one embodiment the drug layer comprises the API and an excipient, such as HPMC. The HPMC may be any grade HPMC as appropriate, such as those detailed herein elsewhere. In one embodiment the HPMC in the drug layer is Methocel E6.

In one embodiment the seal coat and/or the film coat is a PVA-based film coat, such as Opadry 200 white.

In one embodiment the controlled release coat comprises or consists of aqueous or non-aqueous based ethyl cellulose (EC), such as Surrelease E-7-19040™. In another embodiment the controlled release coat comprises or consists of aqueous based polyacrylate based dispersion, such as Eudragit E30D™.

In one embodiment the controlled release coat is applied to a 5 to 30% w/w weight gain, such as 5 to 10, for example 10 to 15, such as 15 to 20, for example 20 to 25, such as 25 to 30% w/w weight gain. In one embodiment the controlled release coat is applied to about 5% w/w weight gain, such as about 10% w/w weight gain, for example about 15% w/w weight gain, such as about 20% w/w weight gain, for example about 25% w/w weight gain, such as about 30% w/w weight gain.

Extended-Release Granules (Hot Melt Extrusion Granules)

In one embodiment there is provided a pharmaceutical formulation comprising
  an active pharmaceutical ingredient (API) selected from
    N-[2-hydroxy-3-(1-piperidinyl)-propoxy]-pyridine-1-oxide-3-carboximidoyl chloride, its stereoisomers and the acid addition salts thereof, and
  a release-controlling excipient,
wherein said formulation provides for extended release of said active pharmaceutical ingredient,
wherein said formulation is in the form of extended-release granules.

In one embodiment the pharmaceutical formulation of the present invention are extended-release granules comprising N-[2-hydroxy-3-(1-piperidinyl)-propoxy]-pyridine-1-oxide-3-carboximidoyl chloride, its stereoisomers and the acid addition salts thereof, and a release-controlling excipient.

In one embodiment said extended-release granules are produced by hot melt extrusion (HME).

In one embodiment there is provided a pharmaceutical formulation comprising extended-release granules comprising
  an active pharmaceutical ingredient (API) selected from
    N-[2-hydroxy-3-(1-piperidinyl)-propoxy]-pyridine-1-oxide-3-carboximidoyl chloride, its stereoisomers and the acid addition salts thereof, and
  a release-controlling excipient, wherein said formulation is obtainable by hot melt extrusion.

In one embodiment the release-controlling excipient is a HME excipient (or HME polymer).

In one embodiment extended-release granules are produced by, or obtainable by, hot melt extrusion comprising the steps of
a. mixing an API selected from N-[2-hydroxy-3-(1-piperidinyl)-propoxy]-pyridine-1-oxide-3-carboximidoyl chloride, its stereoisomers and the acid addition salts thereof, and a HME excipient;
b. heating and extruding said API and HME excipient to provide an extrudate comprising said API and HME excipient;
c. subjecting said extrudate to size reduction such as by milling and optionally size fractionation such as by sieving.

In one embodiment there is provided method for producing a pharmaceutical formulation comprising extended-release granules of N-[2-hydroxy-3-(1-piperidinyl)-propoxy]-pyridine-1-oxide-3-carboximidoyl chloride, its stereoisomers and the acid addition salts thereof, said method comprising the steps of
i) providing an API selected from N-[2-hydroxy-3-(1-piperidinyl)-propoxy]-pyridine-1-oxide-3-carboximidoyl chloride, its stereoisomers and the acid addition salts thereof, and a HME excipient, wherein said HME excipient has a melting point of 65-75° C., such as about 70° C.,
ii) mixing said API and HME excipient,
iii) subjecting the API and HME excipient to a melt temperature of 65-75° C., such as 65-70° C.,
iv) extruding said API and HME excipient at a melt pressure of 0-10 bar, such as 0-8 bar, to obtain an extrudate comprising said API and HME excipient,
v) preferably size reducing such as by milling said extrudate comprising the API and HME excipient, and
vi) optionally size fractionating such as by sieving said size reduced extrudate.

The hot-melt extrusion (HME) technology is becoming more prominent in the pharmaceutical industry. Of particular interest is the use of HME to disperse active pharmaceutical ingredients in a matrix at the molecular level, thus forming solid solutions. The technology itself can be described as a process in which a material melts or softens under elevated temperature and pressure and is forced through an orifice by screws. Appropriate thermoplastic behaviour is a prerequisite of any polymer to be used in hot-melt extrusion. The number of such polymers approved for pharmaceutical use is limited to date.

Polymers for HME must exhibit appropriate thermoplastic characteristics to enable the HME process, and they must be thermally stable at extrusion temperatures. The polymeric components used in the extrusion process may function as drug-release controlling excipients. In extruded drug-delivery systems, the polymer serves as a matrix. Polymers with a high solubilization capacity are particularly suitable because they can dissolve large quantities of drugs.

In one embodiment the HME excipient of the present invention is selected from the group consisting of a hot melt lipid excipient, a lipid excipient, a lipid matrix for extended release and a hot-melt coating agent for prolonged-release drug formulations.

In one embodiment the HME excipient is glycerol behenate or glycerol dibehenate. In one embodiment the HME excipient is a blend of different esters of behenic acid with glycerol. In one embodiment the HME excipient is Compritol®888 ATO. Compritol®888 and glycerol behenate has a melting point of about 70° C.

A conventional extrusion temperature is usually 100-200° C. However the API of the present invention, arimoclomol, is not stable at these temperatures. Thus, the HME excipient of the present invention preferably has a melting point which allows HME while maintaining stability of arimoclomol.

In one embodiment the HME excipient of the present invention has a melting point of about 70° C. In one embodiment the HME excipient of the present invention has a melting point of about 65, 66, 67, 68, 69, 70, 71, 72, 73, 74 or 75° C. In one embodiment the HME excipient of the present invention has a melting point of 50-55° C., such as 55-60° C., such as 60-65° C., such as 65-70° C., such as 70-75° C. In one embodiment the HME excipient of the present invention has a melting point of less than 80° C., such as less than 75° C., such as equal to or less than 70° C.

In one embodiment the extrusion temperature or melt temperature of the hot melt extrusion process is about 50-55° C., such as 55-60° C., such as 60-65° C., such as 65-70° C., such as 70-75° C. In one embodiment the extrusion temperature is 60-61° C., such as 61-62° C., such as 62-63° C., such as 63-64° C., such as 64-65° C., such as 65-66° C., such as 66-67° C., such as 67-68° C., such as 68-69° C., such as 69-70° C., such as 70-71° C. In one embodiment the extrusion temperature is 67-69° C. In one embodiment the extrusion temperature is less than 80° C., such as less than 75° C., such as equal to or less than 70° C.

The hot melt extrusion process employs pressure. In one embodiment the extrusion pressure or melt pressure is 0-10 bar. In one embodiment the extrusion pressure is 0-1 bar, such as 1-2 bar, such as 2-3 bar, such as 3-4 bar, such as 4-5 bar, such as 5-6 bar, such as 6-7 bar, such as 7-8 bar, such as 8-9 bar, such as 9-10 bar.

In one embodiment the instrument torque is 5-20%, such as 5-6%, 6-7%, 7-8%, 8-9%, 9-10%, 10-11%, 11-12%, 12-13%, 13-14%, 14-15%, 15-16%, 16-17%, 17-18%, 18-19%, such as 19-20%.

Strands or extrudates produced via hot melt extrusion may be milled. In one embodiment the hot melt extrudate comprising API and HME excipient is subject to a further step of size reduction such as by milling. In one embodiment the hot melt extrudate is cooled, or allowed to cool, such as to room temperature, prior to size reduction.

In one embodiment the size reduced or milled hot melt extrudate comprising API and HME excipient is subject to a further step of size fractionation such as by sieving. In this way powders of different particle sizes can be separated.

The steps of size reduction such as by milling and optionally size fractionation by sieving results in extended-release granules (or micro-granules).

Sieve fractions may be individually collected to obtain sieve fractions with specific particle sizes. 'Particle size' as used herein can equally refer to 'mean particle size'.

In one embodiment the particle size of the extended-release granules is 500-710 µM, 710-1000 µM or more than 1000 µM.

In one embodiment the particle size of the extended-release granules is 500-750 µM, such as 750-1000 µM, such as more than 1000 µM, such as 1000-1250 µM, such as 1250-1500 µM, such as 1500-1750 µM, such as 1750-2000 µM, such as 2000-2500 µM, such as 2500-3000 µM.

In one embodiment the extended-release granules consist of the API and the HME excipient. In one embodiment the extended-release granules consist of 33 wt % API and 67 wt % HME excipient. In one embodiment the extended-release granules consist of 50 wt % API and 50 wt % HME excipient. In one embodiment the extended-release granules consist of 67 wt % API and 33 wt % HME excipient.

The extended-release granules support high drug content. In one embodiment the extended-release granules comprise approx. 33, 50 or 66 wt % API such as arimoclomol. In one embodiment the extended-release granules comprise 15-75 wt % API, such as 15-20, 20-25, 25-30, 30-35, 35-40, 40-45, 45-50, 50-55, 55-60, 60-65 or 65-70, 70-75 wt % API such as arimoclomol. In a particular embodiment the extended-release granules comprise 25 to 75 wt % API, such as 30 to 65 wt % API, such as 25 to 50 wt % API, such as 30 to 50 wt % API.

In one embodiment the extended-release granules comprise 20-60 wt % API, such as 25-50 wt % API, and have a particle size of more than 710 µM, such as more than 1000 µM.

In one embodiment the extended-release granules comprise about 33 wt % API, such as 25-40 wt % API, and have a particle size of more than 1000 µM. In one embodiment the extended-release granules comprise about 33 wt % API, such as 25-40 wt % API, and have a particle size of 710-1000 µM. In one embodiment the extended-release granules comprise about 33 wt % API, such as 25-40 wt % API, and have a particle size of 500-710 µM.

In one embodiment the extended-release granules comprise about 50 wt % API, such as 40-55 or 40-60 wt % API, and have a particle size of more than 1000 µM. In one embodiment the extended-release granules comprise about 50 wt % API, such as 40-55 or 40-60 wt % API, and have a particle size of 710-1000 µM. In one embodiment the extended-release granules comprise about 50 wt % API, such as 40-55 or 40-60 wt % API, and have a particle size of 500-710 µM.

In one embodiment the extended-release granules comprise about 66 wt % API, such as 55-70 wt % API, and have a particle size of more than 1000 µM.

In one embodiment the extended-release granules of the present invention are contained within a capsule, such as to provide a multiple-unit oral dosage form, such as a capsule comprising extended-release granules according to the invention. In one embodiment the capsule comprises or consists of gelatin. In one embodiment the capsule is a hard-shelled capsule, such as hard-capsule gelatin. In a further embodiment the capsule further comprises an outer coating.

In one embodiment the extended-release granules of the present invention are contained within a pouch or sachet.

Extended-release granules are readily mixable in liquids of in food stuffs for oral ingestion or by feeding tube.

In one embodiment the extended-release granules of the present invention are compressed to form a tablet, mini-tablet or micro-tablet.

Active Pharmaceutical Ingredient

The active pharmaceutical ingredient (API) comprised in the present formulations is selected from N-[2-hydroxy-3-(1-piperidinyl)-propoxy]-pyridine-1-oxide-3-carboximidoyl chloride (arimoclomol), its stereoisomers and the acid addition salts thereof. Arimoclomol is further described in e.g. WO 00/50403.

It is an aspect of the invention to provide a formulation comprising N-[2-hydroxy-3-(1-piperidinyl)-propoxy]-pyridine-1-oxide-3-carboximidoyl chloride (arimoclomol), its optically active (+) or (−) enantiomer, a mixture of the enantiomers of any ratio, and the racemic compound, furthermore, the acid addition salts formed from any of the above compounds with mineral or organic acids constitute objects of the present invention. All possible geometrical isomer forms of N-[2-hydroxy-3-(1-piperidinyl)-propoxy]-pyridine-1-oxide-3-carboximidoyl chloride belong to the scope of the invention. The term "the stereoisomers of N-[2-hydroxy-3-(1-piperidinyl)-propoxy]-pyridine-1-oxide-3-carboximidoyl chloride" refers to all possible optical and geometrical isomers of the compound.

If desired, the N-[2-hydroxy-3-(1-piperidinyl)-propoxy]-pyridine-1-oxide-3-carboximidoyl chloride or one of its optically active enantiomers can be transformed into an acid addition salt with a mineral or organic acid, by known methods.

In one embodiment the active pharmaceutical ingredient is the racemate of N-[2-hydroxy-3-(1-piperidinyl)-propoxy]-pyridine-1-oxide-3-carboximidoyl chloride.

In one embodiment the active pharmaceutical ingredient is an optically active stereoisomer of N-[2-hydroxy-3-(1-piperidinyl)-propoxy]-pyridine-1-oxide-3-carboximidoyl chloride.

In one embodiment the active pharmaceutical ingredient is an enantiomer of N-[2-hydroxy-3-(1-piperidinyl)-propoxy]-pyridine-1-oxide-3-carboximidoyl chloride.

In one embodiment the active pharmaceutical ingredient is selected from the group consisting of (+)-R—N-[2-hydroxy-3-(1-piperidinyl)-propoxy]-pyridine-1-oxide-3-carboximidoyl chloride and (−)-(S)—N-[2-hydroxy-3-(1-piperidinyl)-propoxy]-pyridine-1-oxide-3-carboximidoyl chloride.

In one embodiment the active pharmaceutical ingredient is an acid addition salt of N-[2-hydroxy-3-(1-piperidinyl)-propoxy]-pyridine-1-oxide-3-carboximidoyl chloride.

In one embodiment the active pharmaceutical ingredient is selected from the group consisting of N-[2-hydroxy-3-(1-piperidinyl)-propoxy]-pyridine-1-oxide-3-carboximidoyl chloride citrate, and N-[2-hydroxy-3-(1-piperidinyl)-propoxy]-pyridine-1-oxide-3-carboximidoyl chloride maleate.

In one embodiment the active pharmaceutical ingredient is selected from the group consisting of (+)-R—N-[2-hydroxy-3-(1-piperidinyl)-propoxy]-pyridine-1-oxide-3-carboximidoyl chloride citrate; (−)-S—N-[2-hydroxy-3-(1-piperidinyl)-propoxy]-pyridine-1-oxide-3-carboximidoyl chloride citrate; (+)-R—N-[2-hydroxy-3-(1-piperidinyl)-propoxy]-pyridine-1-oxide-3-carboximidoyl chloride maleate; and (−)-S—N-[2-hydroxy-3-(1-piperidinyl)-propoxy]-pyridine-1-oxide-3-carboximidoyl chloride maleate.

Administration and Dosage

According to the present invention, the active pharmaceutical ingredient (API) is administered to individuals in need of treatment in pharmaceutically effective doses. A therapeutically effective amount of an API according to the present invention is an amount sufficient to cure, prevent, reduce the risk of, alleviate or partially arrest the clinical manifestations of a given disease or condition and its complications. The amount that is effective for a particular therapeutic purpose will depend on the severity and the sort of the disease as well as on the weight and general state of the subject.

The pharmaceutical formulation according to the present invention is in one embodiment administered 1 to 3 times per day, such as once a day, such as twice per day, for example 3 times per day. Preferably, the pharmaceutical formulation is administered once a day, or twice a day.

Administration in one embodiment occurs for a limited time, such as 1 or 2 days to 7 days, for example 7 days to 14 days, such as 14 days to a month, for example from a month to several months (2, 3, 4, 5, 6, 7, 8, 9, 10, 11, 12 months); or administration is in one embodiment chronic, the treatment may be chronic from the onset of diagnosis, such as throughout the lifetime of the individual or as long as the individual will benefit from administration i.e. when the disease is present or while having an increased risk of developing a disease.

The administration of the pharmaceutical formulation according to the present invention is in one embodiment administered to an individual at various time points of treatment. The treatment may be done over one continued period, or in intervals with periods in between wherein the administration is stopped, decreased or altered. Such treatment periods or non-treatment periods may vary in length, and is in one embodiment 1 day to 60 days, such as 1 to 3 days, 3 to 6 days, 6 to 8 days, 8 to 14 days, 14 to 21 days, 21 to 30 days, 30 to 42 days, 42 to 49 days or 49 to 60 days.

The pharmaceutical composition according to the present invention in one embodiment comprises the API in an amount of 0.1 to 100 mg per dosage; such as about 0.1, 0.5, 1, 2, 3, 4, 5, 6, 7, 8, 9, 10, 15, 20, 25, 50 or 100 mg of API per dosage. Dosage may refer to dosage form, tablet or capsule.

In a further embodiment, the API is present in the formulation in an amount of 0.1 to 0.5 mg per dosage, such as 0.5 to 1 mg, for example 1 to 2 mg, such as 2 to 3 mg, for example 3 to 4 mg, such as 4 to 5 mg, for example 5 to 7.5 mg, such as 7.5 to 10 mg, for example 10 to 15 mg, such as 15 to 20 mg, for example 20 to 30 mg, such as 30 to 40 mg, for example 40 to 50 mg, such as 50 to 60 mg per dosage, for example 60 to 70 mg, such as 70 to 80 mg, for example 80 to 90 mg, such as 90 to 100 mg API per dosage.

In a particular embodiment, the amount of API per dosage is about 10 mg, such as about 15 mg, such as about 20 mg per dosage.

In a further embodiment, the API is present in one dosage form or formulation unit—such as individual tablet and sphreres, or a collection of tablets or sphere, or a composition of HME granules, in a total amount of 5-1000 mg per dosage, such as 5-10, 10-25, 25-50, 50-75, 75-100, 100-150, 150-200, 200-250, 250-300, 300-400, 400-500, 500-600, 600-700, 700-800, 800-900, 900-1000 mg API per dosage.

The target dosage for the API is in one embodiment within a range of 0.1 to 100 mg/kg bodyweight, such as 0.1 to 0.5 mg/kg, for example 0.5 to 1.0 mg/kg, such as 1 to 2 mg/kg, for example 2 to 5 mg/kg, such as 5 to 10 mg/kg, for example 10 to 15 mg/kg, such as 15 to 20 mg/kg, for example 20 to 30 mg/kg, such as 30 to 40 mg/kg, for example 40 to 50 mg/kg, such as 50 to 75 mg/kg, for example 75 to 100 mg/kg bodyweight.

In a particular embodiment the dose range is about 15 to 50 mg, and the target dose is about 1 mg/kg.

Target Population

The pharmaceutical formulation according to the present invention can be administered to any individual in need of treatment. An individual in need of treatment is any individual that will, or is likely to, benefit from treatment with the active pharmaceutical ingredient according to the present invention.

It is also an aspect of the present invention to provide a pharmaceutical formulation comprising an active pharmaceutical ingredient selected from N-[2-hydroxy-3-(1-piperidinyl)-propoxy]-pyridine-1-oxide-3-carboximidoyl chloride, its stereoisomers and the acid addition salts thereof, wherein said formulation provides for extended release of said active pharmaceutical ingredient, for administration to an individual selected from the group consisting of paediatric patients; patients presenting with increased serum creatinine; and patients under treatment with an active pharmaceutical ingredient different from the active pharmaceutical ingredient according to the present invention In one embodiment a paediatric patient comprises infants, children, and adolescents ranging from birth up to 18 years of age. In one embodiment a paediatric patient is 0 to 1 years, such as 1 to 2, for example 2 to 3, such as 3 to 4, for example 4 to 5, such as 5 to 6, for example 6 to 7, such as 7 to 8, for example 8 to 9, such as 9 to 10, for example 9 to 10, such as 10 to 11, for example 11 to 12, such as 12 to 13, for example 13 to 14, such as 14 to 15, for example 15 to 16, such as 16 to 17, for example 17 to 18 years of age. In a particular embodiment a paediatric patient according to the present invention is 5 to 15 years of age.

In one embodiment a patient presenting with increased serum creatinine according to the present invention is a patient having increased basal levels of serum creatinine, such as increased levels as compared to the levels that would be present in the serum in the same patient had that patient not suffered from the condition that causes the creatinine levels to rise. Thus an increased creatinine level in one patient may correspond to a serum concentration of creatinine that in another individual is considered 'normal', 'not increased' or that individual's basal level.

Increased serum creatinine can be a marker of disease as its levels are frequently correlated with disease states. Thus, a patient having one or more medical conditions prior to receiving treatment with the pharmaceutical formulation of the present invention for a given further condition could benefit from the present invention.

In one embodiment a patient presenting with increased serum creatinine is a patient with kidney disease (nephropathy) including non-inflammatory nephropathy (nephrosis) and inflammatory nephropathy (nephritis); and/or a patient with decreased renal function; including the stages renal insufficiency, renal failure and uremia.

In one embodiment a patient with kidney disease is a patient having a condition selected from the group consisting of IgA nephropathy (include deposition of the IgA antibodies in the glomerulus), focal segmental glomerulosclerosis, drug and toxin-induced chronic tubulointerstitial nephritis (e.g. analgesics, chemotherapy agents), xanthine oxidase deficiency, polycystic kidney disease, acute kidney injury (AKI), chronic kidney disease (CKD), glomerulonephritis, renal artery stenosis, ischemic nephropathy, hemolytic-uremic syndrome, vasculitis, obstructive kidney disease (kidney stones and disease of the prostate), long-term exposure to lead or its salts; nephropathy caused by chronic conditions including systemic lupus erythematosus, diabetes mellitus and hypertension, which lead to lupus nephritis, diabetic nephropathy and hypertensive nephropathy, respectively; and chronic kidney disease of unknown origin (CKDu) such as Mesoamerican Nephropathy (MeN; aka. 'creatinina').

In one embodiment a patient presenting with increased serum creatinine is a patient with diabetes mellitus, including diabetes mellitus type I and diabetes mellitus type II.

In one embodiment a patient presenting with increased serum creatinine according to the present invention is a patient with hypertension, such as a hypertensive patient having a blood pressure of at or above 140/90 mmHg.

In one embodiment a patient under treatment with an active pharmaceutical ingredient different from the active pharmaceutical ingredient according to the present invention is a patient that receives one or more further active pharmaceutical ingredients for the treatment or management of a given condition. Said given condition can be a condition that is different from the condition that the pharmaceutical formulation of the present invention is effective in.

In one embodiment the at least two or more active pharmaceutical ingredients that a patient under treatment with an active pharmaceutical ingredient different from the active pharmaceutical ingredient according to the present invention comprises i) N-[2-hydroxy-3-(1-piperidinyl)-propoxy]-pyridine-1-oxide-3-carboximidoyl chloride, its stereoisomers and the acid addition salts thereof, and ii) a compound that interacts with N-[2-hydroxy-3-(1-piperidinyl)-propoxy]-pyridine-1-oxide-3-carboximidoyl chloride, its stereoisomers and the acid addition salts thereof OR a compound that increases serum creatinine.

In one embodiment the pharmaceutical formulation of the present invention avoids or reduces the arimoclomol-induced increase in serum creatinine and thus reduces the risk of contraindications in patients who receive additional medications.

Medical Use

It is an aspect to provide a pharmaceutical formulation according to the present invention for use as a medicament.

It is an aspect of the present invention to provide a pharmaceutical formulation according to the present invention for use in a method of treating paediatric patients, patients presenting with increased serum creatinine; and patients under treatment with an active pharmaceutical ingredient different from the active pharmaceutical ingredient according to the present invention.

It is an aspect of the present invention to provide use of a pharmaceutical formulation according to the present invention for the manufacture of a medicament for treatment of paediatric patients, patients presenting with increased serum creatinine; and patients under treatment with an active pharmaceutical ingredient different from the active pharmaceutical ingredient according to the present invention.

It is an aspect of the present invention to provide a method for treating paediatric patients, patients presenting with increased serum creatinine; and patients under treatment with an active pharmaceutical ingredient different from the active pharmaceutical ingredient according to the present invention, said method comprising the step of administering a pharmaceutical formulation according to the present invention.

It is an aspect of the present invention to provide a pharmaceutical formulation according to the present invention for use in a method of treating a paediatric disease.

It is an aspect of the present invention to provide a pharmaceutical formulation according to the present invention for use in a method of treating a lysosomal storage disease (LSD).

It is an aspect of the present invention to provide the use of a pharmaceutical formulation according to the present invention for the manufacture of a medicament for treating a lysosomal storage disease (LSD).

It is an aspect of the present invention to provide a method of treating a lysosomal storage disease (LSD) comprising administering a patient in need thereof a pharmaceutical formulation according to the present invention.

Lysosomal storage diseases are a group of approximately 40 rare inherited metabolic disorders that result from defects in lysosomal function as a consequence of deficiency of a single enzyme required for the metabolism of lipids, glycoproteins or mucopolysaccharides. Although each disorder results from different gene mutations that translate into a deficiency in enzyme activity, they all share a common biochemical characteristic—all lysosomal disorders originate from an abnormal accumulation of substances inside the lysosome.

It is an aspect of the present invention to provide a pharmaceutical formulation according to the present invention for use in a method of treating a lysosomal storage disease selected from the group consisting of lipid storage disorders (or lipidosis) including sphingolipidoses, gangliosidoses and leukodystrophies; mucopolysaccharidoses, glycoprotein storage disorders (or glycoproteinosis) and mucolipidoses.

In one embodiment the lysosomal storage disorder is selected from the group consisting of Niemann-Pick disease, Farber disease, Krabbe disease, Fabry disease, Gaucher disease, Sialidosis (Mucolipidosis type I), Metachromatic leukodystrophy (late infantile, juvenile, and adult forms) and saposin-deficiency.

In one embodiment the Niemann-Pick disease is selected from the group consisting of Niemann-Pick disease type A, Niemann-Pick disease type B, Niemann-Pick disease type C and Niemann-Pick disease type D.

In one embodiment the Gaucher disease is selected from the group consisting of Gaucher disease type I (nonneuropathic type), type II (acute infantile neuropathic Gaucher's disease) and type III (chronic neuropathic form).

It is an aspect of the present invention to provide a pharmaceutical formulation according to the present invention for use in a method of treating amyotrophic lateral sclerosis (ALS).

It is an aspect of the present invention to provide the use of a pharmaceutical formulation according to the present invention for the manufacture of a medicament for treating amyotrophic lateral sclerosis (ALS).

It is an aspect of the present invention to provide a method of treating amyotrophic lateral sclerosis (ALS) comprising administering a patient in need thereof a pharmaceutical formulation according to the present invention.

Items of the Invention:

1. A pharmaceutical formulation comprising an active pharmaceutical ingredient selected from N-[2-hydroxy-3-(1-piperidinyl)-propoxy]-pyridine-1-oxide-3-carboximidoyl chloride, its stereoisomers and the acid addition salts thereof, wherein said formulation comprises an inner matrix and at least one outer coating, wherein said formulation provides for extended release of said active pharmaceutical ingredient.

2. The pharmaceutical formulation according to any of the preceding items, wherein said formulation is a solid dosage form, such as an orally available solid dosage form.

3. The pharmaceutical formulation according to any of the preceding items, wherein said inner matrix comprises the active pharmaceutical ingredient.

4. The pharmaceutical formulation according to any of the preceding items, wherein said inner matrix is selected from the group consisting of a tablet, a mini-tablet and a micro-tablet.

5. The pharmaceutical formulation according to any of the preceding items, wherein said formulation is selected from the group consisting of a coated tablet, a coated mini-tablet and a coated micro-tablet.

6. The pharmaceutical formulation according to any of the preceding items, wherein said outer coating does not comprise the active pharmaceutical ingredient.

7. The pharmaceutical formulation according to any of the preceding items, wherein said inner matrix and/or said outer coating each comprises one or more excipients, such as one or more release-controlling excipients.

8. The pharmaceutical formulation according to any of the preceding items, wherein said release-controlling excipient is selected from the group consisting of hydroxypropylmethylcellulose (HPMC), ethylcellulose (EC), methylcellulose, hydroxypropyl cellulose, hypromellose acetate succinate, hypromellose phthalate, cellulose acetate, glycerin monostearate, glyceryl monooleate, glyceryl palmitate, glyceryl behenate, hydrogenated vegetable oil, guar gum, polyvinyl alcohol, alginates, xanthan gum, carnauba wax, yellow wax, white wax, zein, carregeenan, carbomers and agar.

9. The pharmaceutical formulation according to any of the preceding items, wherein said coating comprises a film-forming excipient.

10. The pharmaceutical formulation according to any of the preceding items, wherein said inner matrix comprises at least one hydroxypropylmethylcellulose (HPMC).

11. The pharmaceutical formulation according to any of the preceding items, wherein said HPMC is a HPMC having a grade providing for a viscosity of 50 to 100,000 cps, a high-viscosity grade HPMC or an ultra-high-viscosity grade HPMC.

12. The pharmaceutical formulation according to any of the preceding items, wherein said HPMC is selected from the group consisting of Methocel E50 Premium LV, K100 Premium LV CR, K4M Premium CR, K15M Premium CR, K100M Premium CR, E4M Premium CR, E10M Premium CR, K200M, E5 and E50.

13. The pharmaceutical formulation according to any of the preceding items, wherein said release-controlling excipient is present in an amount of 20 to 50% w/w, such as 20 to 25% w/w, for example 25 to 30% w/w, such as 30 to 35% w/w, for example 35 to 40% w/w, such as 40 to 45% w/w, for example 45 to 50% w/w.

14. The pharmaceutical formulation according to any of the preceding items, wherein said inner matrix comprises one or more ionic, non-ionic and/or water-insoluble polymers.

15. The pharmaceutical formulation according to any of the preceding items, wherein said ionic polymer is selected from the group consisting of sodium carboxy-methylcellulose (na CMC), sodium alginate, polymers of acrylic acid or carbomers (carbopol 934, 940, 974P NF), enteric polymers such as polyvinyl acetate phthalate (PVAP), methacrylic acid copolymers (Eudragit L100 L 30D 55, S and FS 30 D), hypromellose acetate succinate (AQOAT HPMCAS) and xanthan gum.

16. The pharmaceutical formulation according to any of the preceding items, wherein said non-ionic polymer is selected from the group consisting of HPC (hydroxypropyl cellulose) and PEO (POLYOX, Dow Chemical Company) in various molecular weight grades (from 100,000 to 7,000,000 da).

17. The pharmaceutical formulation according to any of the preceding items, wherein said water-insoluble polymer is selected from the group consisting of ethylcellulose (e.g. ETHOCEL or Surrelease), cellulose acetate, methycrylic acid copolymers (e.g. Eudragit NE 30D), ammonio-methacrylate copolymers (e.g. Eudragit RL 100 or PO RS100) and polyvinyl acetate.

18. The pharmaceutical formulation according to any of the preceding items, wherein said inner matrix comprises one or more further excipients such as one or more fillers, binders and/or lubricants.

19. The pharmaceutical formulation according to any of the preceding items, wherein said inner matrix comprises one or more fillers, such as one or more fillers selected from the group consisting of calcium carbonate, calcium phosphates, calcium sulfate, cellulose, cellulose acetate, compressible sugar, dextrate, dextrin, dextrose, ethylcellulose, fructose, isomalt, lactitol, lactose, mannitol, magnesium carbonate, magnesium oxide, maltodextrin, microcrystalline cellulose (MCC), polydextrose, sodium alginate, sorbitol, talc and xylitol.

20. The pharmaceutical formulation according to any of the preceding items, wherein said inner matrix comprises one or more binders, such as one or more binders selected from the group consisting of acacia, alginic acid, carbomers, carboxymethylcellulose sodium, carrageenan, cellulose acetate phthalate, chitosan, copovidone, dextrate, dextrin, dextrose, ethylcellulose, gelatin, guar gum, hydroyethyl cellulose, hydroxyethylmethyl cellulose, hydroxypropyl cellulose, hydroxypropyl starch, hypromellose, methylcellulose, poloxamer, polydextrose, polyethylene oxide, povidone, sodium alginate, sucrose, starch, pregelatinized starch and maltodextrin.

21. The pharmaceutical formulation according to any of the preceding items, wherein said inner matrix comprises one or more lubricants, such as one or more lubricants selected from the group consisting of calcium stearate, glycerin monostearate, glyceryl behenate, glyceryl palmitostearate, hydrogenated castor oil, hydrogenated vegetable oil, magnesium lauryl sulfate, magnesium stearate, medium chain triglyceride, palmitic acid, polyethylene glycol, sodium lauryl sulfate, stearic acid, talc, silica and zinc stearate.

22. The pharmaceutical formulation according to any of the preceding items, wherein said inner matrix comprises one or more of the excipients hydroxypropylmethylcellulose (HPMC), starch, ethylcellulose (EC), microcrystalline cellulose (MCC), silica, magnesium stearate and stearic acid.

23. The pharmaceutical formulation according to any of the preceding items, wherein said inner matrix further comprises microcrystalline cellulose (MCC), such as Avicel PH 101 or Avicel PH 102.

24. The pharmaceutical formulation according to any of the preceding items, wherein said second excipient, such as MCC, is present in an amount of 10 to 50% w/w, such as 10 to 15% w/w, for example 15 to 20% w/w, such as 20 to 25% w/w, for example 25 to 30% w/w, such as 30 to 35% w/w, for example 35 to 40% w/w, such as 40 to 45% w/w, for example 45 to 50% w/w.

25. The pharmaceutical formulation according to any of the preceding items, wherein said inner matrix further comprises starch, such as an amount of 5 to 30% w/w, such as 5 to 10% w/w, for example 10 to 15% w/w, such as 15 to 20% w/w, for example 20 to 25% w/w, such as 25 to 30% w/w starch.

26. The pharmaceutical formulation according to any of the preceding items, wherein said inner matrix further comprises ethylcellulose (EC), such as in an amount of 5 to 30% w/w, such as 5 to 10% w/w, for example 10 to 15% w/w, such as 15 to 20% w/w, for example 20 to 25% w/w, such as 25 to 30% w/w.

27. The pharmaceutical formulation according to any of the preceding items, wherein said inner matrix further comprises silica, such as colloidal silica, such as in an amount of 0.05 to 1% w/w, such as 0.05 to 0.1, for example 0.1 to 0.2, such as 0.2 to 0.3, for example 0.3 to 0.4, such as 0.4 to 0.5, for example 0.5 to 0.6, such as 0.6 to 0.7, for example 0.7 to 0.8, such as 0.8 to 0.9, for example 0.9 to 1.0% w/w.

28. The pharmaceutical formulation according to any of the preceding items, wherein said inner matrix further comprises magnesium stearate, such as in an amount of 0.1 to 5% w/w, such as 0.1 to 0.5, for example 0.5 to 1.0, such as 1 to 2, for example 2 to 3, such as 3 to 4, for example 4 to 5% w/w.

29. The pharmaceutical formulation according to any of the preceding items, wherein said inner matrix further comprises stearic acid, such as in an amount of 0.1 to 10% w/w, such as 0.1 to 0.5, for example 0.5 to 1.0, such as 1 to 2, for example 2 to 3, such as 3 to 4, for example 4 to 5, such as 4 to 5, for example 5 to 6, such as 5 to 6, for example 6 to 7, such as 7 to 8, for example 8 to 9, such as 9 to 10% w/w.

30. The pharmaceutical formulation according to any of the preceding items, wherein said inner matrix is compressed to form a tablet, such as a tablet with a hardness of 10 to 50 kp (kilopond), such as 10 to 15 kp, for example 15 to 20 kp, such as 20 to 25 kp, for example 25 to 30 kp, such as 30 to 35 kp, for example 35 to 40 kp, such as 40 to 50 kp.

31. The pharmaceutical formulation according to any of the preceding items, wherein said outer coating comprises one or more layers of coating.

32. The pharmaceutical formulation according to any of the preceding items, wherein said outer coating comprises one or more excipients.

33. The pharmaceutical formulation according to any of the preceding items, wherein said outer coating comprises or consists of aqueous based ethylcellulose (EC), solvent based EC or aqueous based polymethacrylate.

34. The pharmaceutical formulation according to any of the preceding items, wherein said formulation is coated to a 5% w/w weight gain, such as a 10% w/w weight gain, for example a 15% w/w weight gain, such as a 20% w/w weight gain, for example a 25% w/w weight gain, such as a 30% w/w weight gain, for example a 35% w/w weight gain, such as a 40% w/w weight gain.

35. The pharmaceutical formulation according to any of the preceding items, wherein said formulation is coated to a weight gain of 5 to 40% w/w, such as 10 to 15% w/w, for example 15 to 20% w/w, such as 20 to 25% w/w, for example 25 to 30% w/w, such as 30 to 35% w/w, for example 35 to 40% w/w.

36. The pharmaceutical formulation according to any of the preceding items, wherein said outer coating further comprises an outer seal coating.

37. The pharmaceutical formulation according to any of the preceding items, wherein said formulation comprises or consists of:
   i) an inner matrix comprising or consisting of
      a. 5-40% N-[2-hydroxy-3-(1-piperidinyl)-propoxy]-pyridine-1-oxide-3-carboximidoyl chloride (arimoclomol), its stereoisomers and the acid addition salts thereof, such as 5 to 10, for example 10 to 15, such as 15 to 20, for example 20 to 25, such as 25 to 30, for example 30 to 35, such as 35 to 40% w/w;
      b. 20-50% HPMC, such as 20 to 25% w/w, for example 25 to 30% w/w, such as 30 to 35% w/w, for example 35 to 40% w/w, such as 40 to 45% w/w, for example 45 to 50% w/w HPMC;
      c. 10-50% MCC, for example 10 to 50% w/w, such as 10 to 15% w/w, for example 15 to 20% w/w, such as 20 to 25% w/w, for example 25 to 30% w/w, such as 30 to 35% w/w, for example 35 to 40% w/w, such as 40 to 45% w/w, for example 45 to 50% w/w MCC;
      d. 5-30% starch, such as 5 to 10% w/w, for example 10 to 15% w/w, such as 15 to 20% w/w, for example 20 to 25% w/w, such as 25 to 30% w/w starch;
      e. 0.05-1% silica, such as 0.05 to 0.1, for example 0.1 to 0.2, such as 0.2 to 0.3, for example 0.3 to 0.4, such as 0.4 to 0.5, for example 0.5 to 0.6, such as 0.6 to 0.7, for example 0.7 to 0.8, such as 0.8 to 0.9, for example 0.9 to 1.0% w/w silica;
      f. 0.1-5% magnesium stearate, such as 0.1 to 0.5, for example 0.5 to 1.0, such as 1 to 2, for example 2 to 3, such as 3 to 4, for example 4 to 5% w/w magnesium stearate;
      g. 0.1-10% stearic acid, such as 0.1 to 0.5, for example 0.5 to 1.0, such as 1 to 2, for example 2 to 3, such as 3 to 4, for example 4 to 5, such as 5 to 6, for example 6 to 7, such as 7 to 8, for example 8 to 9, such as 9 to 10% w/w stearic acid; and
      h. Optionally 5-30% (EC), such as 5 to 10% w/w, for example 10 to 15% w/w, such as 15 to 20% w/w, for example 20 to 25% w/w, such as 25 to 30% w/w EC; and
   ii) optionally an outer coating comprising or consisting of
      a. an aqueous based ethylcellulose (EC), a solvent based EC and/or an aqueous based polymethacrylate, applied to a weight gain of 5 to 40% w/w, such as 10 to 15% w/w, for example 15 to 20% w/w, such as 20 to 25% w/w, for example 25 to 30% w/w, such as 30 to 35% w/w, for example 35 to 40% w/w; and
      b. optionally an outer seal coating.

38. The pharmaceutical formulation according to any of the preceding items, wherein said formulation comprises or consists of:
   i) an inner matrix comprising or consisting of
      a. 5-40% N-[2-hydroxy-3-(1-piperidinyl)-propoxy]-pyridine-1-oxide-3-carboximidoyl chloride (arimoclomol), its stereoisomers and the acid addition salts thereof,
      b. 20-50% HPMC,
      c. 10-50% MCC,
      d. 5-30% starch,
      e. 0.05-1% silica,
      f. 0.1-5% magnesium stearate, and
      g. 0.1-10% stearic acid, and
   ii) an outer coating comprising or consisting of
      a. an aqueous based ethylcellulose (EC), a solvent based EC and/or an aqueous based polymethacrylate, applied to a weight gain of 5 to 25% w/w; and
      b. optionally an outer seal coating.

39. The pharmaceutical formulation according to any of the preceding items, wherein said outer coating comprises the active pharmaceutical ingredient.

40. The pharmaceutical formulation according to any of the preceding items, wherein said formulation comprises an inner matrix or sphere substrate, and an outer coating comprising one or more individual layers.

41. The pharmaceutical formulation according to any of the preceding items, wherein said outer coating comprising two or more layers, such as three or more layers, such as four or more layers, such as five or more layers.

42. The pharmaceutical formulation according to any of the preceding items, wherein said formulation is a coated sphere, such as a coated sphere comprising a sphere substrate and an outer coating comprising one or more individual layers.

43. The pharmaceutical formulation according to any of the preceding items, wherein the first or innermost layer of the outer coating comprises the active pharmaceutical ingredient.

44. The pharmaceutical formulation according to any of the preceding items comprising 1) a sphere substrate, 2) a drug layer comprising the active pharmaceutical ingredient, 3) optionally a seal coat, 4) a controlled release coat, and 5) optionally a film coat.

45. The pharmaceutical formulation according to any of the preceding items comprising 1) a sphere substrate, 2) a drug layer to 1 to 10% w/w weight gain, 3) optionally a seal coat to 0.1 to 5% w/w weight gain, 4) a controlled release coat to 5 to 20% w/w weight gain, and 5) optionally a film coat to 1 to 10% w/w weight gain.

46. The pharmaceutical formulation according to any of the preceding items comprising 1) a sphere substrate, 2) a drug layer to 4% w/w weight gain, 3) a seal coat to 1% w/w weight gain, 4) a controlled release coat to 5 to 20% w/w weight gain, and 5) a film coat to 3 to 5% w/w weight gain.

47. The pharmaceutical formulation according to any of the preceding items, wherein said inner matrix or sphere substrate comprises or consists of sugar, such as a soluble sugar sphere.

48. The pharmaceutical formulation according to any of the preceding items, wherein said inner matrix or sphere substrate comprises or consists of microcrystalline cellulose (MCC), such as an insoluble microcrystalline cellulose sphere.

49. The pharmaceutical formulation according to any of the preceding items, wherein said drug layer comprises the active pharmaceutical ingredient and an excipient, such as HPMC.

50. The pharmaceutical formulation according to any of the preceding items, wherein said drug layer is applied to 1 to 10% w/w weight gain, such as 1 to 2, for example 2 to 3, such as 3 to 4, for example 4 to 5, such as 5 to 6, for example 6 to 7, such as 7 to 8, for example 8 to 9, such as 9 to 10% w/w weight gain.

51. The pharmaceutical formulation according to any of the preceding items, wherein said controlled release coat comprises or consists of aqueous or non-aqueous based ethyl cellulose (EC) or an aqueous based polyacrylate based dispersion.

52. The pharmaceutical formulation according to any of the preceding items, wherein said controlled release coat is applied to a 5 to 30% w/w weight gain, such as 5 to 10, for example 10 to 15, such as 15 to 20, for example 20 to 25, such as 25 to 30% w/w weight gain.

53. The pharmaceutical formulation according to any of the preceding items, wherein said film coat is applied to 1 to 10% w/w weight gain, such as 1 to 2, for example 2 to 3, such as 3 to 4, for example 4 to 5, such as 5 to 6, for example 6 to 7, such as 7 to 8, for example 8 to 9, such as 9 to 10% w/w weight gain. In one embodiment the film coat is applied to about 1% w/w weight gain, such as 2, for example 3, such as 4, for example 5, such as 6, for example 7, such as 8, for example 9, such as about 10% w/w weight gain.

54. The pharmaceutical formulation according to any of the preceding items, wherein said seal coat is applied to 0.1 to 5% w/w weight gain, such as 0.1 to 0.5, for example 0.5 to 1, such as 1 to 2, for example 2 to 3, such as 3 to 4, for example 4 to 5% w/w weight gain.

55. The pharmaceutical formulation according to any of the preceding items comprising or consisting of:
  a. a sphere substrate having 50 to 90% w/w sugar or MCC, such as 50 to 55% w/w, for example 55 to 60% w/w, such as 60 to 65% w/w, for example 65 to 70% w/w, such as 70 to 75% w/w, for example 75 to 80% w/w, such as 80 to 85% w/w, for example 85 to 90% w/w sugar or MCC;
  b. a drug layer having 1 to 10% w/w N-[2-hydroxy-3-(1-piperidinyl)-propoxy]-pyridine-1-oxide-3-carboximidoyl chloride (arimoclomol), its stereoisomers and the acid addition salts thereof, such as 1 to 2, for example 2 to 3, such as 3 to 4, for example 4 to 5, such as 5 to 6, for example 6 to 7, such as 7 to 8, for example 8 to 9, such as 9 to 10% w/w; and having 1 to 10% w/w HPMC, such as Methocel E6, such as 1 to 2, for example 2 to 3, such as 3 to 4, for example 4 to 5, such as 5 to 6, for example 6 to 7, such as 7 to 8, for example 8 to 9, such as 9 to 10% w/w HPMC;
  c. a seal coat having 0.1 to 5% w/w PVA-based film coat, such as 0.1 to 0.5, for example 0.5 to 1, such as 1 to 2, for example 2 to 3, such as 3 to 4, for example 4 to 5% w/w;
  d. a controlled release coat having 5 to 30% w/w EC or polyacrylate, such as 5 to 10, for example 10 to 15, such as 15 to 20, for example 20 to 25, such as 25 to 30% w/w EC or polyacrylate; and
  e. optionally a film coat having 1 to 10% w/w PVA-based film coat, such as 1 to 2, for example 2 to 3, such as 3 to 4, for example 4 to 5, such as 5 to 6, for example 6 to 7, such as 7 to 8, for example 8 to 9, such as 9 to 10% w/w PVA-based film coat.

56. The pharmaceutical formulation according to any of the preceding items comprising or consisting of:
  a. a sphere substrate having 67% w/w sugar or MCC,
  b. a drug layer having 4% w/w N-[2-hydroxy-3-(1-piperidinyl)-propoxy]-pyridine-1-oxide-3-carboximidoyl chloride (arimoclomol), its stereoisomers and the acid addition salts thereof, and having 5% w/w HPMC, such as Methocel E6,
  c. a seal coat having 1% w/w PVA-based film coat,
  d. a controlled release coat having 5 to 20% w/w EC or polyacrylate, and
  e. optionally a film coat having 3% w/w PVA-based film coat.

57. The pharmaceutical formulation according to any of the preceding items, wherein said formulation is a single-unit oral dosage form.

58. The pharmaceutical formulation according to any of the preceding items, wherein said formulation is a multiple-unit oral dosage form.

59. The pharmaceutical formulation according to any of the preceding items, wherein said formulation is contained within a capsule, such as a hard shell capsule, such as a capsule comprising gelatin, such as a hard-shelled capsule further comprising an outer coating.

60. The pharmaceutical formulation according to any of the preceding items, wherein said formulation is multiple-unit oral dosage, said dosage form comprising a capsule comprising two or more formulation units of any of the preceding items.

61. The pharmaceutical formulation according to any of the preceding items, wherein said formulation unit is selected from the group consisting of a coated mini-tablet, a coated micro-tablet and a coated sphere.

62. The pharmaceutical formulation according to any of the preceding items, wherein said active pharmaceutical ingredient is the racemate of N-[2-hydroxy-3-(1-piperidinyl)-propoxy]-pyridine-1-oxide-3-carboximidoyl chloride.

63. The pharmaceutical formulation according to any of the preceding items, wherein said active pharmaceutical ingredient is an optically active stereoisomer of N-[2-hydroxy-3-(1-piperidinyl)-propoxy]-pyridine-1-oxide-3-carboximidoyl chloride.

64. The pharmaceutical formulation according to any of the preceding items, wherein said active pharmaceutical ingredient is an enantiomer of N-[2-hydroxy-3-(1-piperidinyl)-propoxy]-pyridine-1-oxide-3-carboximidoyl chloride.

65. The pharmaceutical formulation according to any of the preceding items, wherein said active pharmaceutical ingredient is selected from the group consisting of (+)-R—N-[2-hydroxy-3-(1-piperidinyl)-propoxy]-pyridine-1-oxide-3-carboximidoyl chloride, and (−)-(S)—N-[2-hydroxy-3-(1-piperidinyl)-propoxy]-pyridine-1-oxide-3-carboximidoyl chloride.

66. The pharmaceutical formulation according to any of the preceding items, wherein said active pharmaceutical ingredient is an acid addition salt of N-[2-hydroxy-3-(1-piperidinyl)-propoxy]-pyridine-1-oxide-3-carboximidoyl chloride.

67. The pharmaceutical formulation according to any of the preceding items, wherein said active pharmaceutical ingredient is selected from the group consisting of N-[2-hydroxy-3-(1-piperidinyl)-propoxy]-pyridine-1-oxide-3-carboximidoyl chloride citrate, and N-[2-hydroxy-3-(1-piperidinyl)-propoxy]-pyridine-1-oxide-3-carboximidoyl chloride maleate.

68. The pharmaceutical formulation according to any of the preceding items, wherein said active pharmaceutical ingredient is selected from the group consisting of (+)-R—N-[2-hydroxy-3-(1-piperidinyl)-propoxy]-pyridine-1-oxide-3-carboximidoyl chloride citrate; (−)-S—N-[2-hydroxy-3-(1-piperidinyl)-propoxy]-pyridine-1-oxide-3-carboximidoyl chloride citrate; (+)-R—N-[2-hydroxy-3-(1-piperidinyl)-propoxy]-pyridine-1-oxide-3-carboximidoyl chloride maleate; and (−)-S—N-[2-hydroxy-3-(1-piperidinyl)-propoxy]-pyridine-1-oxide-3-carboximidoyl chloride maleate.

69. The pharmaceutical formulation according to any of the preceding items, wherein said formulation comprises said active pharmaceutical ingredient in an amount of 0.1 mg to 100 mg, for example 0.1 to 0.5 mg, such as 0.5 to 1 mg, for example 1 to 2 mg, such as 2 to 3 mg, for example 3 to 4 mg, such as 4 to 5 mg, for example 5 to 7.5 mg, such as 7.5 to 10 mg, for example 10 to 15 mg, such as 15 to 20 mg, for example 20 to 30 mg, such as 30 to 40 mg, for example 40 to 50 mg, such as 50 to 60 mg per dosage, for example 60 to 70 mg, such as 70 to 80 mg, for example 80 to 90 mg, such as 90 to 100 mg.

70. The pharmaceutical formulation according to any of the preceding items, wherein said formulation comprises one or more further active pharmaceutical ingredients.

71. The pharmaceutical formulation according to any of the preceding items, wherein said active pharmaceutical ingredient is to be administered in a dosage of 0.1 to 100 mg/kg bodyweight, such as 0.1 to 0.5 mg/kg, for example 0.5 to 1.0 mg/kg, such as 1 to 2 mg/kg, for example 2 to 5 mg/kg, such as 5 to 10 mg/kg, for example 10 to 15 mg/kg, such as 15 to 20 mg/kg, for example 20 to 30 mg/kg, such as 30 to 40 mg/kg, for example 40 to 50 mg/kg, such as 50 to 75 mg/kg, for example 75 to 100 mg/kg bodyweight.

72. The pharmaceutical formulation according to any of the preceding items, wherein said formulation has a dissolution rate of 85% of the active pharmaceutical ingredient released within 3 to 5 hours (medium).

73. The pharmaceutical formulation according to any of the preceding items, wherein said formulation has a dissolution rate of 85% active pharmaceutical ingredient released after a 6 hours (slow).

74. The pharmaceutical formulation according to any of the preceding items, wherein said formulation provides for a dissolution rate of 10 to 90% of the API released at 3 to 5 hours, such as 10 to 20, 20 to 30, 30 to 40, 40 to 50, 50 to 60, 60 to 70, 70 to 75, 75 to 80, 80 to 85 or 85 to 90% of the active pharmaceutical ingredient released within 3 to 5 hours, such as within 3 hrs, within 4 hrs, or within 5 hrs.

75. The pharmaceutical formulation according to any of the preceding items, wherein said formulation provides for a dissolution rate of 10 to 90% of the API released within 6 hours, such as 10 to 20, for example 20 to 30, such as 30 to 40, for example 40 to 50, such as 50 to 60, for example 60 to 70, such as 70 to 75, for example 75 to 80, such as 80 to 85, for example 85 to 90% of the active pharmaceutical ingredient released within ≥6 hours, such as within a ≥7 hours, ≥8 hours, ≥9 hours, ≥10 hours, ≥11 hours, ≥12 hours, ≥13 hours, ≥14 hours, ≥15 hours, ≥16 hours, ≥17 hours, ≥18 hours.

76. The pharmaceutical formulation according to any of the preceding items, wherein said formulation provides for a lower Cmax of the active pharmaceutical ingredient as compared to an immediate-release formulation of the active pharmaceutical ingredient.

77. The pharmaceutical formulation according to any of the preceding items, wherein said formulation provides for a reduced inhibition of the OCT2 transporter by the active pharmaceutical ingredient, as compared to an immediate-release formulation of the active pharmaceutical ingredient.

78. The pharmaceutical formulation according to any of the preceding items, wherein said formulation provides for a reduced effect on serum creatinine by the active pharmaceutical ingredient, as compared to an immediate-release formulation of the active pharmaceutical ingredient.

79. The pharmaceutical formulation according to any of the preceding items, wherein said formulation provides for a Cmax of less than 20 µM, such as less than 15 µM, for example less than 10 µM, such as less than 9 µM, for example less than 8 µM, such as less than 7 µM, for example less than 6 µM, such as less than 5 µM, for example less than 4 µM, such as less than 3 µM, for example less than 2 µM, such as less than 1 µM.

80. The pharmaceutical formulation according to any of the preceding items, wherein said formulation provides for a Cmax of 1 to 2 µM, for example 2 to 3 µM, such as 3 to 4 µM, for example 4 to 5 µM, such as 5 to 6 µM, for example 6 to 7 µM, such as 7 to 8 µM, for example 8 to 9 µM, such as 9 to 10 µM, for example 10 to 11 µM, such as 11 to 12 µM, for example 12 to 13 µM, such as 13 to 14 µM, for example 14 to 15 µM, such as 15 to 16 µM, for example 16 to 17 µM, such as 17 to 18 µM, for example 18 to 19 µM, such as 19 to 20 µM.

81. The pharmaceutical formulation according to any of the preceding items, wherein said formulation is to be administered once daily.

82. The pharmaceutical formulation according to any of the preceding items, wherein said formulation is to be administered in combination with one or more further active pharmaceutical ingredients, separately, sequentially or simultaneously.

83. The pharmaceutical formulation according to any of the preceding items, for administration to an individual selected from the group consisting of paediatric patients; patients presenting with increased serum creatinine; and patients under treatment with an active pharmaceutical ingredient different from the active pharmaceutical ingredient according to the present invention.
84. The pharmaceutical formulation according to any of the preceding items, for administration to a patient having a disease selected from a kidney disease (nephropathy) including non-inflammatory nephropathy (nephrosis) and inflammatory nephropathy (nephritis); diabetes mellitus type I and diabetes mellitus type II and hypertension.
85. The pharmaceutical formulation according to any of the preceding items for use as a medicament.
86. The pharmaceutical formulation according to any of the preceding items for use in a method of treating paediatric patients, patients presenting with increased serum creatinine; and patients under treatment with an active pharmaceutical ingredient different from the active pharmaceutical ingredient of said pharmaceutical formulation.
87. The pharmaceutical formulation according to any of the preceding items for use in a method of treating a disease selected from the group consisting of a paediatric disease; a lysosomal storage disease (LSD); a LSD selected from the group consisting of lipid storage disorders (or lipidosis) including sphingolipidoses, gangliosidoses and leukodystrophies; mucopolysaccharidoses, glycoprotein storage disorders (or glycoproteinosis) and mucolipidoses; and amyotrophic lateral sclerosis (ALS).

EXAMPLES

Example 1: In Vitro Interaction Studies of Arimoclomol with the Human OATP1B1, OATP1B3, OCT2, OAT1 and OAT3 Uptake Transporters The purpose of this study was to provide data on the interaction of arimoclomol with the human SLC (uptake) transporters: OATP1B1 (OATP2, OATP-C), OATP1B3 (OATP8), OAT1, OAT3, and OCT2 (Table 1).

TABLE 1

Test article (TA) and transporter assays

| Test article | Transporter | Assay | Applied concentrations ($\mu M$) |
|---|---|---|---|
| Arimoclomol | OATP1B1 | Uptake transporter inhibition assay | 0.3, 1, 3, 10, 30, 100, 300 |
| | OATP1B3 | | |
| | OAT1 | Uptake transporter inhibition and substrate assay | 0.3, 1, 3, 10, 30, 100, 300 (inhibition); 1 and 10 (substrate) |
| | OAT3 | | |
| | OCT2 | | |

Summary of the Results
Arimoclomol was soluble up to 300 $\mu M$ in the assay buffer used for the assays.
Uptake Transporter Inhibition Assays
Arimoclomol inhibited the OCT2-mediated probe substrate accumulation at the applied concentrations (in a dose-dependent manner) with a maximum inhibition of 98.36 (FIG. 5). The calculated IC50 was 9.72 $\mu M$. Arimoclomol did not influence the OATP1B1-, OATP1B3-, OAT1- and OAT3-mediated probe substrate accumulation at the applied concentrations (FIG. 1, FIG. 2, FIG. 3 and FIG. 4).
Uptake Transporter Substrate Assays
No relevant fold accumulation of arimoclomol (fold accumulations were <2) into the cells was observed at the applied concentrations (1 and 10 $\mu M$) and time points (2 and 20 min) in the OAT1 (FIG. 6), OAT3 (FIG. 7) and OCT2 (FIG. 8) substrate feasibility experiments. The highest fold accumulations of arimoclomol were 0.77 for OAT1 (1 $\mu M$ and 2 min), 0.86 for OAT3 (1 $\mu M$, after both 2 and 20 min) and 1.28 for OCT2 (1 $\mu M$ and 20 min; Table 6Table). The positive control experiments confirmed the function of the transporter in the applied cells.

TABLE 2

Summary of the obtained results

| Transporter | $IC_{50}$ ($\mu M$) | Maximum inhibition (% of control) | Substrate |
|---|---|---|---|
| OATP1B1 UP | NA | NIO | NT |
| OATP1B3 UP | NA | NIO | NT |
| OAT1 UP | NA | NIO | NIO |
| OAT3 UP | NA | NIO | NIO |
| OCT2 UP | 9.72 | 98.36 | NIO |

NA: Not applicable
NIO: No interaction observed
NT: Not tested

According to the data arimoclomol is an inhibitor of the OCT2 transporter.
According to the data arimoclomol is not an inhibitor of the OATP1B1, OATP1B3, OAT1 and OAT3 transporters.
According to the data arimoclomol is not a substrate of the OATP1B1, OATP1B3, OAT1, OAT3 and OCT2 transporters.
Materials and Methods
Test Articles, Stock Solutions, Chemicals and Instruments
Test article arimoclomol 313.7799 g/mol was stored at RT. Solubility is 14 g/100 mL at 25° C. (water) and 0.4 g/100 mL at 25° C. (methanol). Stock solutions (1, 10 and 30 mM) were prepared in water. Serial dilutions (7-step, special) were prepared in DMSO, and used as the test solutions in the different assays (100-fold dilution in Uptake assays). The dilution factor in substrate experiments was 1000-fold. The solvent concentration in the assay buffer did not exceed 1.1% (v/v) in the rest of the assays.
Instruments used for detection include a Thermo Scientific Dionex UltiMate 3000 series UHPLC (Thermo Scientific, San Jose, Calif.) with a Thermo Scientific TSQ Quantum Access Max triple quadrupole MS; a MicroBeta2 liquid scintillation counter (Perkin Elmer, Waltham Mass.) and a BMG Labtech FluoStar Omega multifunctional microplate reader (BMG Labtech, Offenburg, Germany).
Kinetic Solubility Assessment in the Assay Buffers
The aqueous solubility of the TA was determined by spectrophotometric measurements in combination with optical microscopy evaluation (5 and 10× magnification). Colourless compounds do not absorb light in the visible range (400-700 nm), therefore, when TA solutions are measured with a spectrophotometer, background corrected absorbance values higher than blank absorbance values in this wavelength range indicate the presence of light scattering, possibly caused by precipitated particles. The timeframe of the solubility assessment covered the incubation time of the corresponding in vitro experiment.
Experimental Method for Solubility Testing
A stock solution and dilution series (5-step, 2-fold dilution series) of TA were prepared in water. Stock solutions were mixed with the appropriate assay buffers in a 96-wells plate and incubated for 10 minutes at 37° C. before the solutions were evaluated at 500 nm. The measured absorbance values for buffer solutions are typically between 0.010 and 0.030. Therefore, to be considered soluble at a given concentration, the background corrected absorbance of the TA solution must be less than 0.030 absorbance units ($\Delta A = A_{solution} - A_{blank} < 0.030$). The background corrected absorbance value for each solution was determined.

Uptake Transporter Inhibition and Substrate Assays

Uptake experiments were performed using CHO, MDCKII, or HEK293 cells stably expressing the respective uptake transporters. Parameters of the uptake transporter assays are presented in Table 3. Control cell lines, cell culturing as well as plating information are summarized in Table 4.

TABLE 3

Parameters of uptake transporter assays

| Transporter | Applying assay protocol | Incubation time (min) | Probe substrate | Reference inhibitor |
|---|---|---|---|---|
| human OATP1B1 | UPT-HEK293-OATP1B1-E217βG | 3 | E217βG (0.058 μM) | Rifampicin (50 μM) |
| human OATP1B3 | UPT-CHO-OATP1B3-Fluo3 | 10 | Fluo-3 (10 μM) | Fluvastatin (30 μM) |
| human OAT1 | UPT-CHO-OAT1-Tenofovir | 10 | Tenofovir (5 μM) | Probenecid (200 μM) |
| human OAT3 | UPT-MDCKII-OAT3-E3S | 3 | E3S (1 μM) | Probenecid (200 μM) |
| human OCT2 | UPT-CHO-OCT2-Metf | 10 | Metformin (10 μM) | Verapamil (100 μM) |

TABLE 4

Parameters of control cell lines, cell culturing, and plating for uptake transporter assays

| Transporter | Control cell line | Cell number/well* | Culturing medium | Special treatment | Incubation prior to the assay | Buffer |
|---|---|---|---|---|---|---|
| human OATP1B1 | Mock-transfected HEK293 FT | 1 × 105 | DMEM 4.5 g/L glucose | Poly-D-lysine coated plate | 24 h | HK (pH 7.4) |
| human OATP1B3 | Parental CHO-K1 | 1 × 105 | DMEM-F12 | 5 mM Na+ butyrate induction | 24 h | HK (pH 7.4) |
| human OAT1 | Parental CHO-K1 | 1 × 105 | DMEM-F12 | — | 24 h | HK (pH 7.4) |
| human OAT3 | Parental MDCKII | 1 × 105 | DMEM 4.5 g/L glucose | 20 min, 5 mM glutaric acid incubation | 24 h | HK (pH 7.4) |
| human OCT2 | Parental CHO-K1 | 1 × 105 | DMEM-F12 | — | 24 h | HK (pH 7.4) |

*Cell densities refer to 96-wells plate format. In case of 24-wells plates the number of cells plated was 2 × 105 for all transporters Experimental Method for Uptake Transporter Inhibition Experiments Cells were cultured at 37±1° C. in an atmosphere of 95:5 air:$CO_2$ and were plated onto standard 96-well tissue culture plates at the cell number described in table 4.

Before the experiment, the medium was removed and the cells were washed twice with 100 μl of HK buffer at pH 7.4 (prepared from Sigma chemicals, Sigma-Aldrich, St Louis, Mo.). Uptake experiments were carried out at 37±1° C. in 50 μl of HK buffer (pH 7.4) containing the probe substrate and the TA or vehicle control (water).

After the experiment, cells were washed twice with ice cold, 100 μl of HK buffer and lysed with 50 μl of 0.1 M NaOH (1 mM CaCl2) in 5% SDS in the case of OATP1B3). Fluo-3 transport (OATP1B3) was determined by measuring fluorescence using 485 nm and 520 nm as the excitation and emission wavelengths, respectively. Radiolabelled probe substrate transport was determined by measuring an aliquot (35 μl) from each well for liquid scintillation counting.

Uptake of the probe substrate in control cells provided background activity values for all data points. Incubation without TA or reference inhibitor (solvent only) provided 100% activity values. A reference inhibitor served as positive control for inhibition.

Experimental Method for Uptake Transporter Substrate Experiments

Cells were cultured at 37±1° C. in an atmosphere of 95:5 air:CO2 as described in Table 4 and were plated onto standard 24-well tissue culture plates at 2×105 cells/well. The uptake of the TA was determined using cells overexpressing the respective uptake transporter and control cells, at two incubation time points (2 and 20 min) and at two concentrations (1 and 10 μM) of TA to determine whether or not the TA was actively taken up into the cells. In order to confirm the interaction, the transporter-specific uptake of the TA was determined in the presence of a known inhibitor of the respective transporter.

Before the experiment, the medium was removed and the cells were washed twice with 300 μl of HK buffer (pH 7.4) (prepared from Sigma chemicals). Cellular uptake of TA into the cells was measured by adding 300 μl of HK buffer containing TA and incubating them at 37±1° C. Reactions were quenched by removing the HK buffer containing the TA and the cells were washed twice with 300 μl of HK buffer. Cells were lysed by adding 300 μl of MeOH:$H_2O$ (2:1) and incubated for 20 minutes at 4±1° C. The amount of TA in the cell lysate was determined by LC-MS/MS. The amount of protein in each well was quantified using the BCA kit for protein determination (Sigma-Aldrich, St Louis, Mo., USA). Uptake of the probe substrate in control cells provided background activity values for all data points. Incubation without reference inhibitor (solvent only) provided 100% activity values. A reference inhibitor served as positive control for inhibition.

Calculation of Relative Activities

The amount of translocated probe substrate was determined for each well in cpm or RFU. Relative activities were calculated from the equation:

$$\text{Activity \%} = \frac{A-B}{C-D} \times 100$$

A: amount of translocated substrate in the presence of TA in transfected cells
B: amount of translocated substrate in the presence of TA in control cells
C: amount of translocated substrate in the presence of solvent in transfected cells
D: amount of translocated substrate in the presence of solvent in control cells Calculation of Fold Accumulation Values The fold accumulation value was defined as the ratio of uptake of TA or probe substrate into transfected and control cells:

$$\text{Fold accumulation} = \frac{UPT_{TRP}}{UPT_{CTL}}$$

$UPT_{TRP}$: accumulated amount of TA or probe substrate in transfected cells normalized by protein content [pmol/mg protein]
$UPT_{CTL}$: accumulated amount of TA or probe substrate in control cells normalized by protein content [pmol/mg protein]

If the fold accumulation is >2 and can be inhibited by a known inhibitor of the transporter, the TA can be considered to be a substrate of the respective transporter.

Data Processing and Statistics

Microsoft Excel 2010 (Microsoft Corporation, Redmond, Wash.) was used for basic data processing and GraphPad Prism 5.0 (GraphPad Software Inc., San Diego, Calif.) was used for curve fitting and determination of reaction parameters.

In uptake transporter inhibition assays, the $IC_{50}$ (µM) was calculated, where applicable. $IC_{50}$ was defined as the concentration of TA required to inhibit maximal activity by 50%. $IC_{50}$ values were derived from a four parametric logistic equation (log(inhibitor) vs. response—variable slope); the curve was fitted to the relative activity vs. TA concentration plot using non-linear regression. Top (maximal response) and Bottom (maximally inhibited response) values were not constrained to constant values of 100 and 0, respectively, unless it is noted otherwise.

Figure 2:
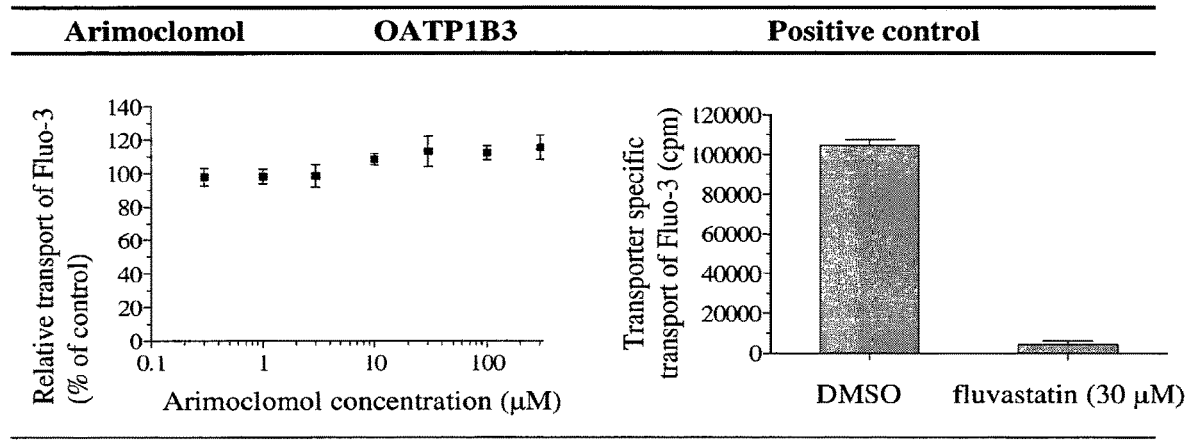
FIG. 2 Inhibition of OATP1B3-mediated probe substrate transport by arimoclomol in the uptake transporter inhibition assay.
Figure 3:
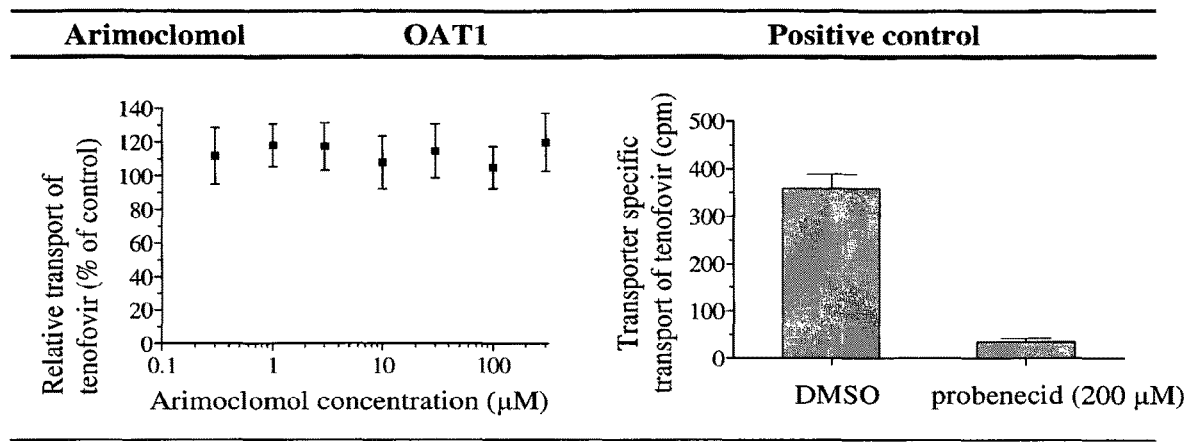
FIG. 3 Inhibition of OAT1-mediated probe substrate transport by arimoclomol in the uptake transporter inhibition assay.
Figure 4:
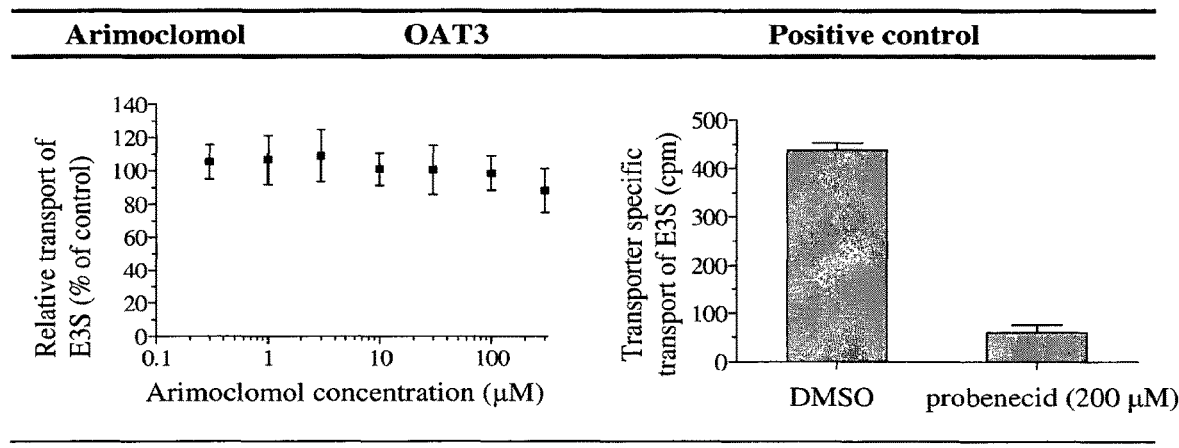
FIG. 4 Inhibition of OAT3-mediated probe substrate transport by arimoclomol in the uptake transporter inhibition assay.
Figure 5:
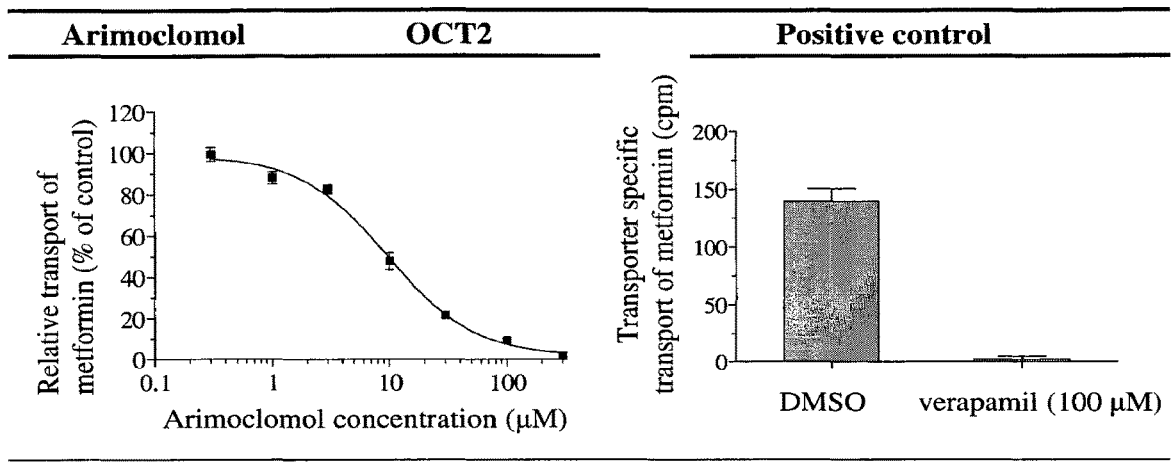
FIG. 5 Inhibition of OCT2-mediated probe substrate transport by arimoclomol in the uptake transporter inhibition assay.
Figure 6:
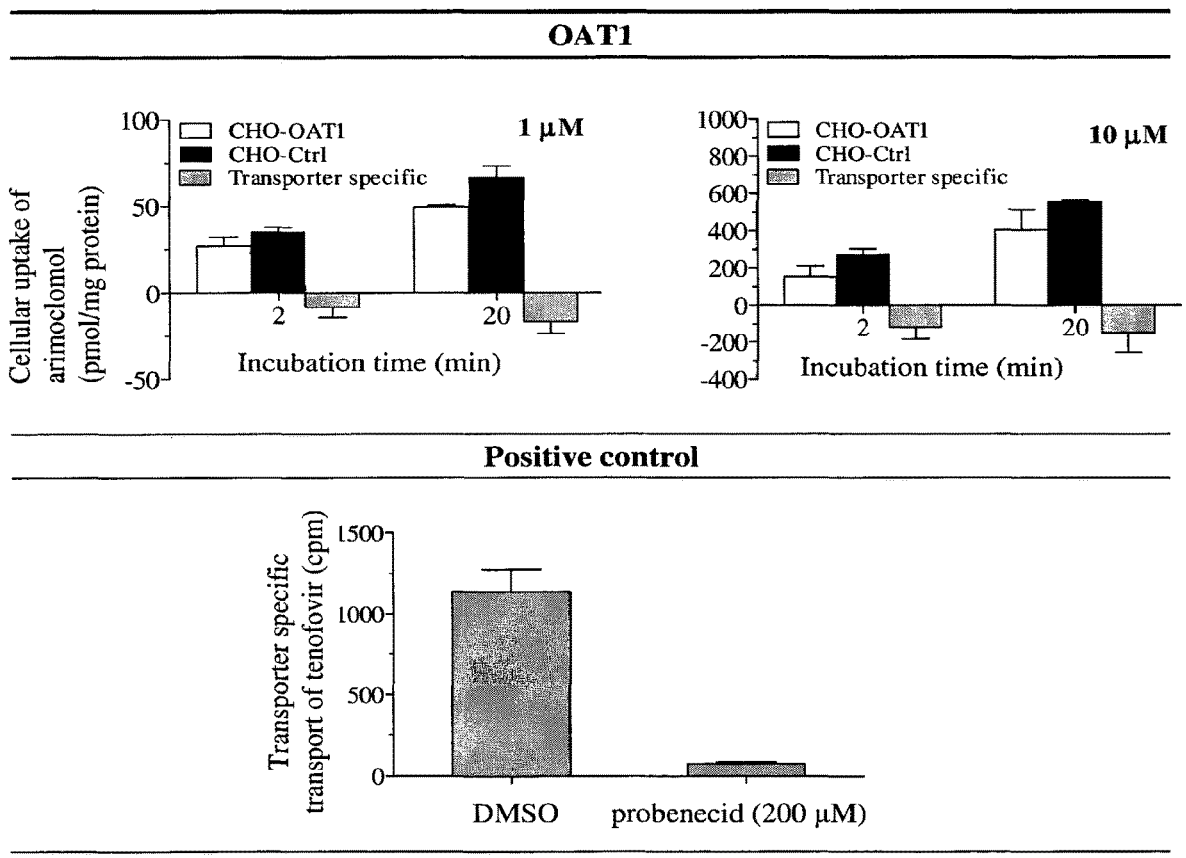
FIG. 6 Accumulation of arimoclomol in OAT1-expressing and CHO control cells in the uptake transporter substrate feasibility assay.
Figure 7:
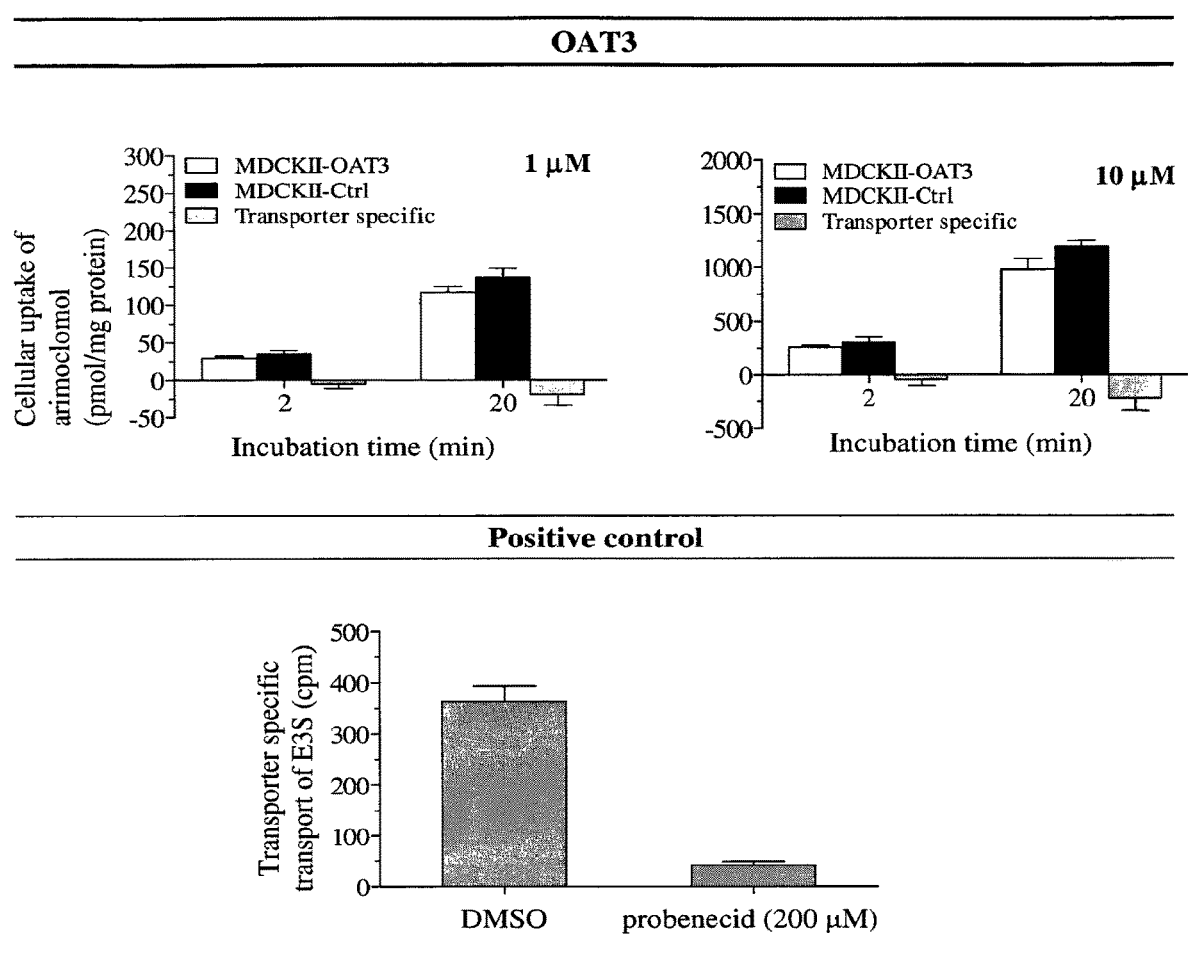
FIG. 7 Accumulation of arimoclomol in OAT3-expressing and MDCKII control cells in the uptake transporter substrate feasibility assay.
Figure 8:
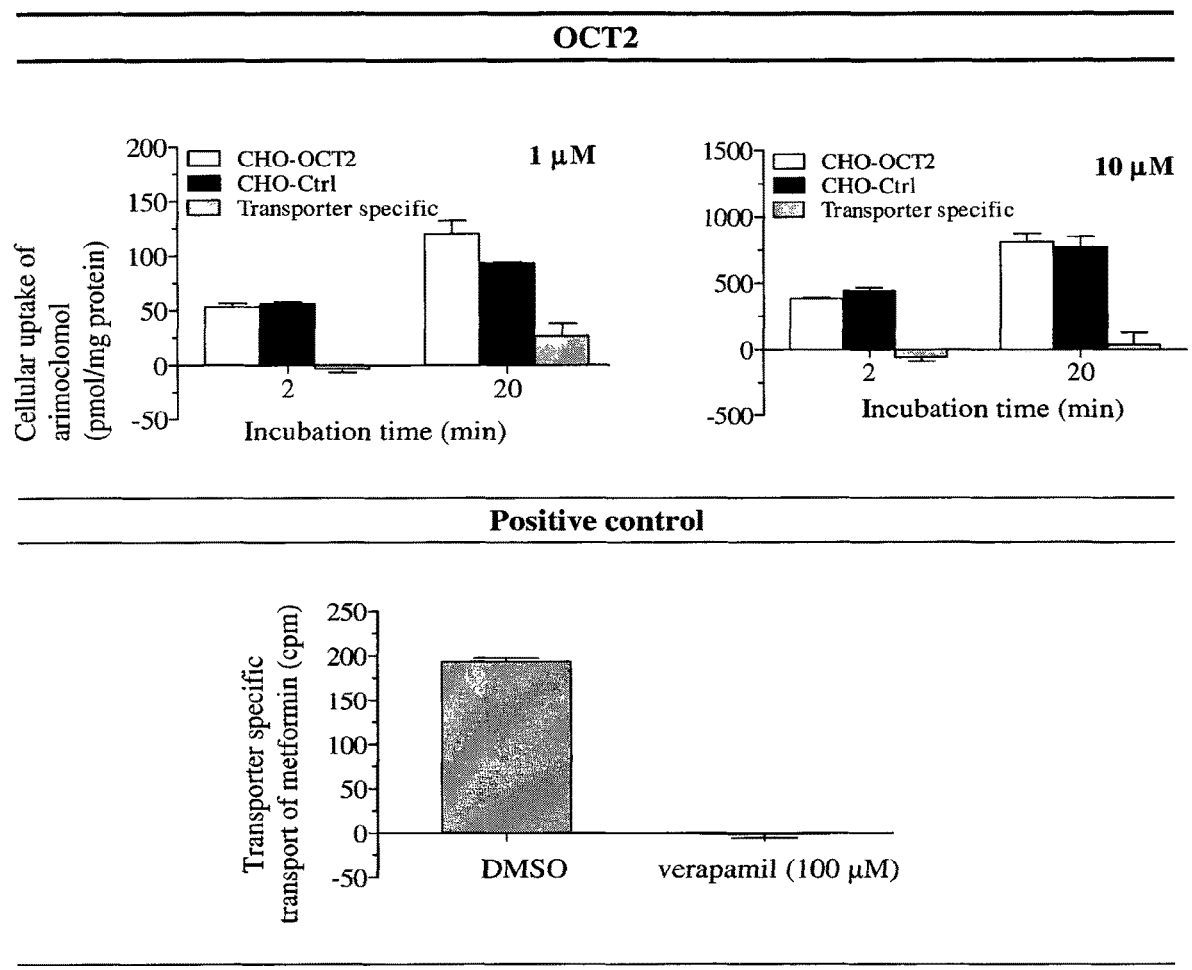
FIG. 8 Accumulation of arimoclomol in OCT2-expressing and CHO control cells in the uptake transporter substrate feasibility assay.

Results
Results of Uptake Transporter Assays
1) Results of uptake transporter inhibition assays—see FIG. 1 (OATP1B1), FIG. 2 (OATP1B3), FIG. 3 (OAT1), FIG. 4 (OAT3), FIG. 5 (OCT2).
2) Results of uptake transporter substrate assays—see FIG. 6 (OAT1), FIG. 7 (OAT3), FIG. 8 (OCT2).

TABLE 5

Calculated reaction parameters from uptake transporter inhibition assays

| Test article | Transporter | IC50 (µM) | maximum inhibition (% of control) |
|---|---|---|---|
| Arimoclomol | OATP1B1 | NA | NIO |
|  | OATP1B3 | NA | NIO |
|  | OAT1 | NA | NIO |
|  | OAT3 | NA | NIO |
|  | OCT2 | 9.72 | 98.36 |

NA: Not applicable
NIO: No interaction observed

TABLE 6

Calculated reaction parameters from uptake transporter substrate feasibility assays with arimoclomol

| Transporter | Conditions (µM/min) | Fold accumulation |
|---|---|---|
| OAT1 | 1/2 | 0.77 |
|  | 1/20 | 0.75 |
|  | 10/2 | 0.56 |
|  | 10/20 | 0.73 |
| OAT3 | 1/2 | 0.86 |
|  | 1/20 | 0.86 |
|  | 10/2 | 0.85 |
|  | 10/20 | 0.82 |
| OCT2 | 1/2 | 0.95 |
|  | 1/20 | 1.28 |
|  | 10/2 | 0.87 |
|  | 10/20 | 1.05 |

Example 2: Development, Manufacture, Release Testing and Stability Studies of a Controlled Release Formulation Containing Arimoclomol The aim of this study is to develop an oral dosage format for arimoclomol that is easy to swallow with acceptable organoleptic characteristics and has an extended release.

Alternative approaches were evaluated to provide controlled-release of the drug substance in a multi particulate format, including Mini-Tablets comprising as dissolution retardants with and without a coating, and drug loaded beads or spheres coated with a controlled release layer.

The drug substance (arimoclomol) is white in appearance and is light and fluffy. It exhibits poor flow properties and is 'sticky'. The bulk density of 0.214 g/cm3, and Carr's Index value of 44.4% was determined suggesting very poor flow. A tapped density of 0.386 g/cm3 was determined following 250 taps.

Mini-Tablets

A total of nine formulation blends were investigated summarised as follows:

HPMC mini-tablets: Blends 1, 2 and 3 contain various ratios of HPMC and starch in the matrix HPMC/EC mini-tablets: Blends 4 and 5 contain various ratios of HPMC, starch and EC in the matrix Waxy matrix: A total of 4 blends were prepared containing a waxy base (Glycerol Dibenhenate or Glycerol Distearate at a concentration of 30% w/w or 40% w/w). Mini-Tablets were not successfully produced when employing a waxy base.

TABLE 7

Dissolution testing throughout was carried out using these parameters:

| | |
|---|---|
| Dissolution Apparatus | USP 2 |
| Paddle Speed | 100 rpm |
| Dissolution Volume | 1000 mL |
| Dissolution Media | USP pH 6.8 phosphate buffer or 0.1M HCl |
| Dissolution Temperature | 37° C. |
| Sample Volume | 5 mL |

HPMC and HPMC/EC Mini-Tablets

HPMC was included in the Mini-Tablet matrix to investigate its ability to delay the release of the drug substance from the Mini-Tablets and therefore act as a controlled release matrix per se. All blends flowed easily into the tablet hopper and were successfully compressed into 2 mm Mini-Tablets, suggestive of suitable flow. No visible signs of capping or lamination were observed.

TABLE 8

Mini-Tablet Weight and Hardness Determination:

| Blend | HPMC/Starch Ratio | Weight (mg) | Hardness (kp) |
|---|---|---|---|
| 1 | 35% w/w HPMC/ 20% w/w starch | 7.68 (RSD 8.92%) | 1.85 (31.36%)* |
| 2 | 40% w/w HPMC/ 15% w/w starch | 7.44 (RSD 16.29%) | 2.34 (49.80%) |
| 3 | 35% w/w HPMC/ 5% w/w starch | 7.06 (RSD 9.04%) | 1.66 (55.47%) |

TABLE 9

Arimoclomol Content of HPMC Mini-Tablet Matrices:

| Blend | HPMC/Starch Ratio | Arimoclomol Content (% w/w) | Target content (% w/w) | % of Theoretical |
|---|---|---|---|---|
| 1 | 35% w/w HPMC/ 20% w/w starch | 16.6 | 18.75 | 88.5 |
| 2 | 40% w/w HPMC/ 15% w/w starch | 16.9 | 18.75 | 80.1 |
| 3 | 35% w/w HPMC/ 5% w/w starch | 15.6 | 18.75 | 83.2 |

Data are weight equivalent to n = 10 Mini Tabs

TABLE 10

Percentage* Arimoclomol dose dissolved:

| Time (minutes) | Percentage Arimicolomol Dissolved Blend | | | | | |
|---|---|---|---|---|---|---|
| | 1 | 1 | 2 | 2 | 3 | 3 |
| 0 | 0 | 0 | 0 | 0 | 0 | 0 |
| 30 | 87.3 | 83.8 | 76.6 | 74.9 | 84.2 | 92.9 |
| 60 | 101.3 | 102.4 | 97.5 | 90.5 | 97.3 | 98.5 |
| 90 | 107.0 | 108.3 | 105.2 | 96.1 | 100.8 | 99.2 |
| 120 | 106.2 | 107.7 | 105.3 | 94.7 | 99.3 | 97.4 |
| 150 | 106.8 | 107.7 | 105.0 | 94.9 | 99.2 | 97.6 |
| 180 | 106.1 | 107.6 | 106.1 | 96.0 | 39.8 | 97.6 |
| 240 | 106.3 | 109.0 | 112.6 | 96.0 | 98.7 | 96.6 |

*Percentage dissolved is based on the uncoated assay value for the blend and not the theoretical content of the blend.

There is no appreciable difference in dissolution profiles observed for HPMC Mini-Tablet blends and the HPMC matrix per se is not working as a controlled release matrix as no signs of delayed release have been observed.

Two blends were prepared containing 5% w/w or 10% w/w ethyl cellulose in Mini-Tablet matrix manipulating the concentration of starch within the matrix. Both blends flowed easily into the tablet hopper and were successfully compressed into 2 mm Mini-Tablets and no visible signs of capping or lamination were observed.

TABLE 11

Mini-Tablet Weight and Hardness Determination of HPMC/EC blends:

| Blend | Ethyl Cellulose (EC)/ Starch Ratio | Weight (mg) | Hardness (kp) |
|---|---|---|---|
| 4 | 5% w/w EC/15% w/w starch | 7.91 (RSD 6.95%) | 2.34 (51.87%) |
| 5 | 10% w/w EC/20% w/w starch | 8.01 (RSD 3.53%) | 2.02 (37.44%) |

TABLE 12

Arimoclomol Content of HPMC/EC Mini-Tablet Matrices:

| Blend | Ethyl Cellulose (EC)/ Starch Ratio | Average Content (% w/w) | % of Theoretical |
|---|---|---|---|
| 4 | 5% w/w EC/15% w/w starch | 18.2 | 97.1 |
| 5 | 10% w/w EC/20% w/w starch | 18.1 | 96.5 |

Data are weight equivalent to n = 10 Mini Tabs

Table 13—Percentage Arimoclomol Dose Dissolved:

TABLE 13

Percentage Arimoclomol dose dissolved:

| Time (minutes) | *Percentage Arimiclomol Dissolved Blend | | | |
|---|---|---|---|---|
| | 4 | | 5 | |
| 0 | 0 | 0 | 0 | 0 |
| 38 | 79.9 | 79.0 | 78.5 | 76.5 |
| 60 | 99.0 | 101.5 | 95.6 | 97.0 |
| 90 | 103.9 | 107.1 | 99.2 | 102.5 |
| 120 | 103.3 | 106.9 | 99.0 | 102.3 |
| 150 | 103.7 | 107.9 | 99.2 | 102.3 |
| 180 | 104.1 | 107.2 | 99.5 | 103.0 |
| 240 | 103.3 | 106.4 | 98.3 | 102.1 |

*Percentage dissolved is based on the uncoated assay value for the blend and not the theoretical content of the blend There is no appreciable difference in dissolution profiles observed for HPMC/EC Mini-Tablet blends with no appreciable change in the release profile following the inclusion of EC independent of concentration.

Coated HPMC and HPMC/EC Mini-Tablets

The dissolution profiles of Blend 1 to Blend 4 were shown to be comparable; therefore coating trials were initially completed on Blend 1. The following coating approaches were adopted:

Use of aqueous based EC dispersion (Surelease™) to 5%, 10% and 20% weight gain

Use of solvent based EC coating to 5%, 10% and 20% weight gain

Use of aqueous based Polymethacrylate based dispersion (Eudragit NE30D™) to 5%, 10% and 20% weight gain.

Mini-Tablets were hand-painted with the appropriate controlled release coating to the desired weight gain. A two stage approach was adopted, therefore based on the dissolution data obtained the HPMC/EC blends (Blend 1-4) were pooled and coated using aqueous based EC dispersion (Surelease™) following seal coating to 5%, 10% and 20% weight gain. Following coating, the Mini-Tablets were subject to dissolution analysis.

TABLE 14

Percentage of Arimoclomol dose dissolved (based on uncoated Assay) with aqueous based Ethyl Cellulose coat (n = 1):

| Time | Percentage Arimicolomol Dissolved % w/w CR Coat | | |
|---|---|---|---|
| (minutes) | 5 | 10 | 20 |
| 0 | 0 | 0 | 3 |
| 30 | 13.9 | 3.8 | −4.4 |
| 60 | 32.4 | 11.7 | −4.1 |
| 90 | 48.8 | 20.2 | −2.3 |
| 120 | 60.5 | 28.0 | 0.3 |
| 150 | 76.8 | 45.0 | 9.6 |
| 180 | 84.9 | 60.2 | 21.5 |
| 240 | 91.2 | 82.4 | 46.0 |
| 300 | 95.3 | 93.7 | 62.8 |
| 360 | 95.2 | 97.9 | 73.6 |

Figure 9:
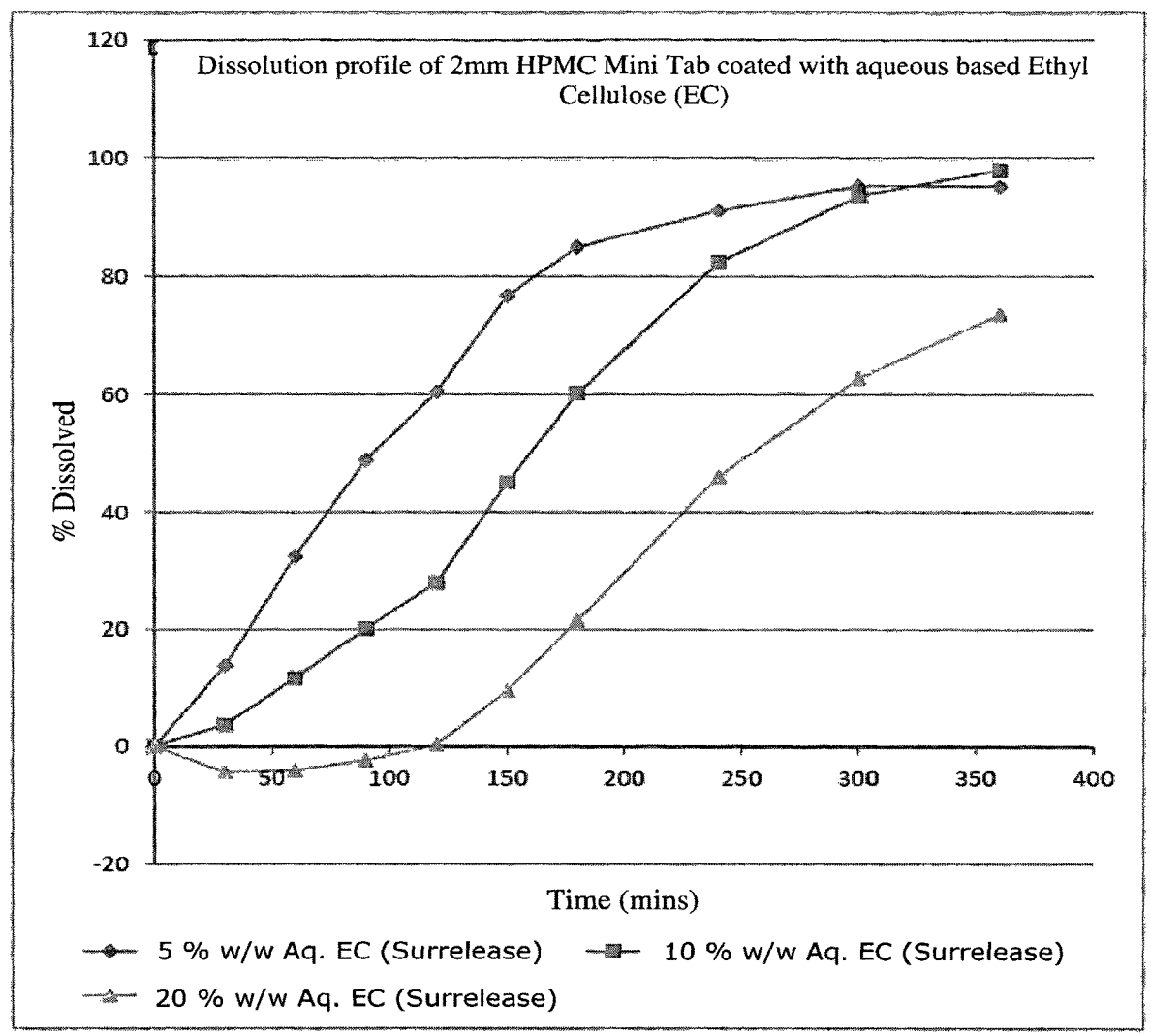
FIG. 9. Dissolution Profile of Mini-Tablets (Blend 1) following coating with aqueous based Ethyl cellulose dispersion (Surelease™) to 5%, 10% and 20% weight gain.

The dissolution profiles are illustrated in FIG. 9.

TABLE 15

Percentage of Arimoclomol dose dissolved (based on uncoated Assay) with solvent based Ethyl Cellulose coat (n = 1):

| Time | Percentage Arimicolomol Dissolved % w/w CR Coat | | |
|---|---|---|---|
| Minutes | 5 | 10 | 20 |
| 0 | 0 | 0 | 0 |
| 30 | 9.0 | 7.2 | 2.5 |
| 60 | 21.8 | 17.4 | 8.6 |
| 90 | 34.0 | 27.5 | 15.6 |
| 120 | 46.0 | 36.8 | 23.1 |
| 150 | 67.1 | 55.3 | 39.1 |
| 180 | 82.2 | 69.5 | 54.2 |
| 240 | 99.6 | 91.3 | 79.0 |
| 300 | 105.1 | 102.7 | 91.4 |
| 360 | 106.5 | 107.9 | 96.9 |

Figure 10:
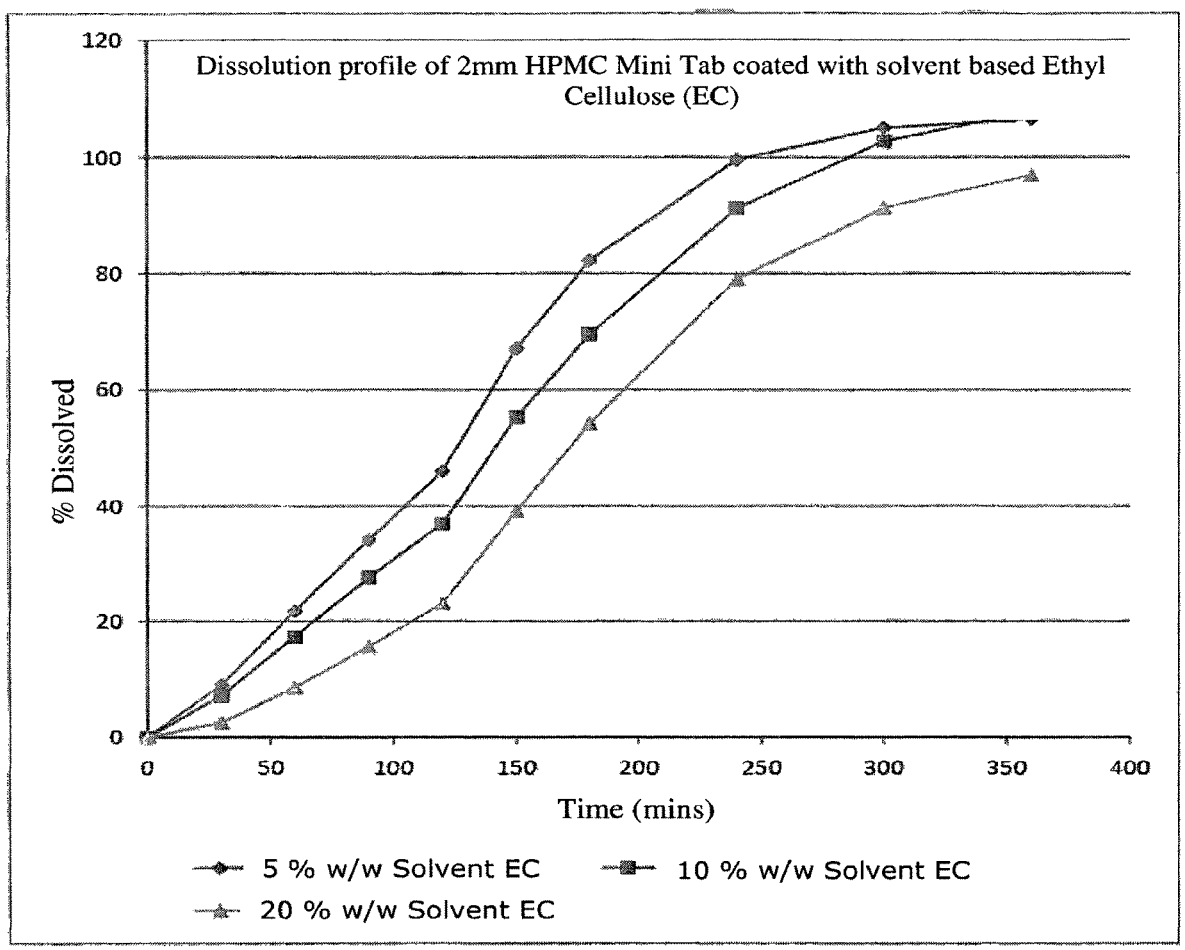
FIG. 10 Dissolution Profile of Mini-Tablets (Blend 1) following coating with solvent based EC dispersion (Surelease™) to 5%, 10% and 20% weight gain.
Figure 11:
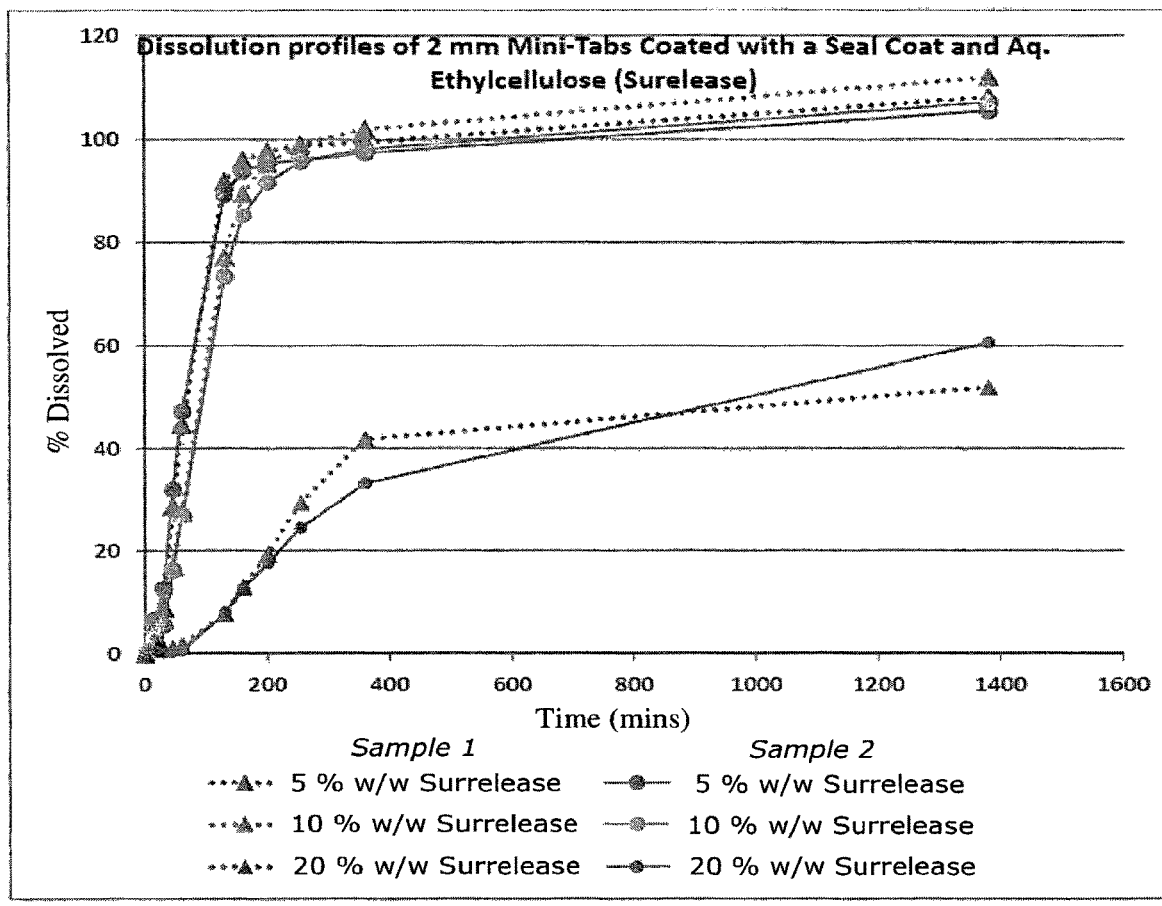
FIG. 11 Dissolution Profile of Mini-Tablets following coating with HPMC seal coat and aqueous based Ethyl cellulose dispersion (Surelease™) to 5%, 10% and 20% weight gain.
Figure 12:
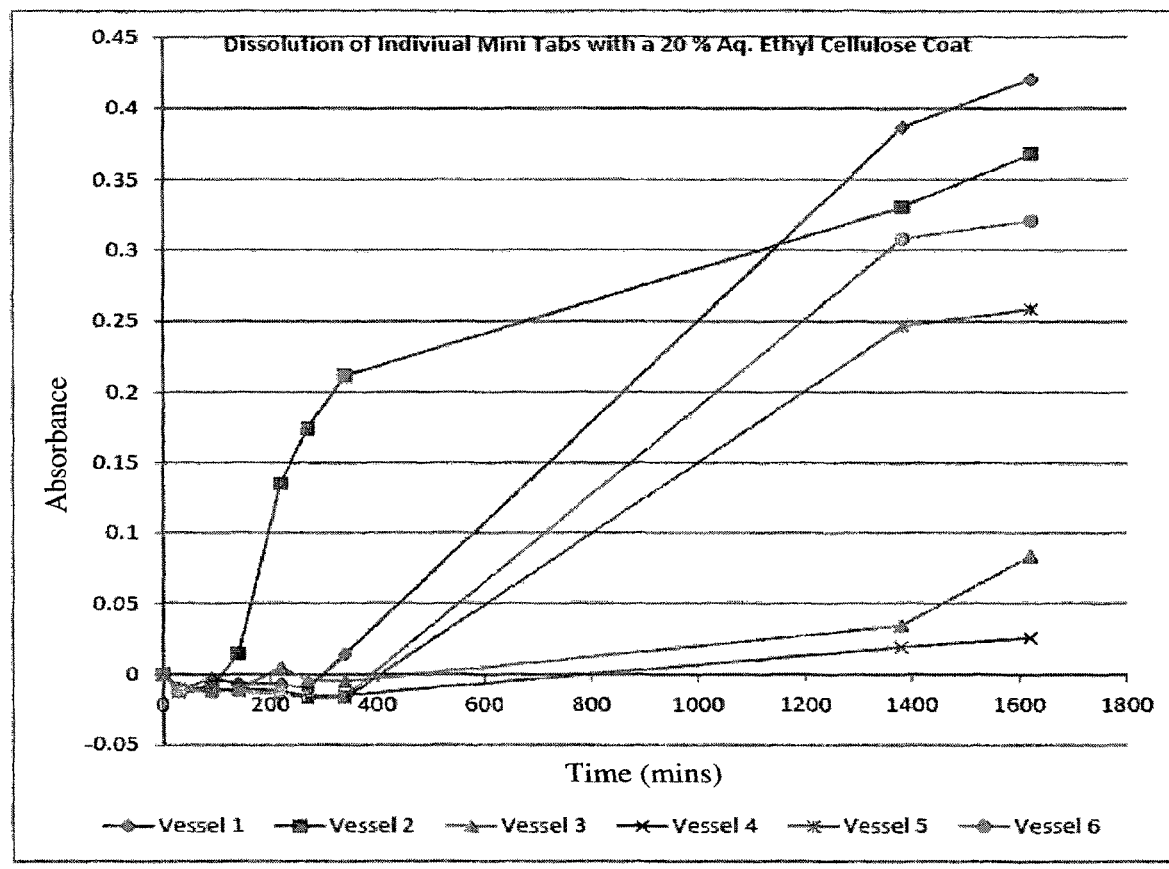
FIG. 12 Dissolution Profile of Individual Mini-Tablets following coating with HPMC seal coat and aqueous based Ethyl cellulose dispersion (Surelease™) to 20% weight gain.

The dissolution profiles are illustrated in FIG. 10.

The coating of HPMC Mini-Tablets with EC resulted in the controlled release of drug from the matrix, with greater delay observed with increased weight gain. This is independent of the composition of the coating solution/dispersion, i.e. aqueous or solvent based. An EC coated layer to 5% w/w weight gain resulted in 13.9% drug released after 30 minutes for aqueous based coating compared to 9% drug release for solvent based coating. Approximately 85% of drug was released at 3 hours, following coating with 5% w/w weight gain, 84.9% drug release was observed for the aqueous EC based coating compared to 82.2% for the solvent based EC coating.

A greater delay in release was observed following coating to a 10% w/w weight gain. At 3 hours, 60.2% and 69.5% drug release was observed for the 10% w/w weight gain EC aqueous and solvent based coating respectively. Coating to 20% w/w weight gain resulted in variable data between aqueous and solvent based coating. 73.6% of drug was released after 6 hours for aqueous based EC coating, a value of 96.9% was observed for solvent based coating. The variation in the dissolution profiles may be attributed to the variation in the integrity of the coating layer, any cracks or fractures within the layer will enable the release of the drug from the Mini-Tablet matrix.

The coating of Mini-Tablets with Polymethacrylate based dispersion (Eudragit NE30D) was not successful, Mini-Tablets were produced that were soft following coating and subsequently disintegrated.

Coating Mini-Tablets by Automated Glatt Process. Based on the hand-painted data and the un-coated HPMC/EC Mini-Tablet dissolution data blends Blend 4 and Blend 5 was pooled to provide sufficient Mini-Tablets to enable coating using the Mini-Glatt fitted with the micro-kit. Prior to the coating with aqueous based EC dispersion (Surelease™) a seal coat was applied. This was to prevent the swelling of the Mini-Tablet matrix during the coating process. The seal coat (20% w/w HPMC) was coated to 5% weight gain. Following the seal coat the controlled release coat (Surelease™) was applied to 5%, 10% and 20% weight gain. The resultant Mini-Tablets were subject to dissolution testing according to the parameters in table 7 illustrates the dissolution profile of the Mini-Tablets following seal and controlled release coat.

Coated Mini-Tablet Dissolution Results. The coating of HPMC/EC Mini-Tablets with EC resulted in the controlled release of drug from the matrix, with greater delay observed with increased weight gain. At 60 minutes 46.0% of drug was released following coating to 5% w/w weight gain compared to 27.1% and 1.1% following coating to 10% to 20% weight gain. Data are average of n=2 analyses.

TABLE 16

Percentage of Arimoclomol dose dissolved (based on uncoated Assay):

| Time | Percentage Arimicolomol Dissolved % w/w CR Coat | | | | | |
|---|---|---|---|---|---|---|
| Minutes | 5 | 5 | 10 | 10 | 20 | 20 |
| 0 | 0 | 0 | 0 | 0 | 0 | 0 |
| 15 | 4.9 | 6.6 | 3.5 | 3 | 2.5 | 0.8 |
| 30 | 8.8 | 12.5 | 6.7 | 5.4 | 0.9 | 0.3 |
| 45 | 28.6 | 32 | 16.8 | 16.2 | 1.1 | 0.4 |
| 60 | 44.7 | 47.2 | 27.4 | 26.8 | 1.6 | 0.6 |
| 130 | 91.9 | 89.3 | 77.1 | 73.4 | 7.8 | 7.9 |
| 160 | 96 | 93.9 | 89.5 | 85.3 | 12.9 | 12.6 |
| 200 | 97.7 | 95.4 | 95.4 | 31.7 | 19.4 | 17.6 |
| 255 | 98.8 | 96 | 99 | 95.7 | 29.4 | 24.4 |
| 360 | 99.5 | 97.5 | 102 | 98.2 | 41.8 | 33.2 |
| 1380 | 108.2 | 105.5 | 112 | 107.2 | 51.9 | 60.6 |

Following coating to 5% weight gain, 95% of drug was released at 3 hours and is comparable to the data obtained following hand-coating. Comparable data are obtained following coating to 10% weight gain, with 93.6% of drug released at 200 minutes. Coating to 20% weight gain did not result in the total release of drug over 23 hours, with 56.3% of drug released. Although coating to 20% weight gain appears to retard the delay in drug release the individual Mini-Tablets within the dissolution bath exhibit differing behaviours. A total of 10 Mini-Tablets were analysed, for 5 of the Mini-Tablets the coating layer was penetrated by the dissolution media resulting in the HPMC matrix swelling and splitting the EC coat and releasing the drug. In contrast the coat of the remaining Mini-Tablets was not penetrated and tablet core swelling and coat rupture had not occurred and no drug release was observed. Based on the data a modified dissolution test was completed in 250 mL of dissolution media, analysing n=1 Mini-Tablets per dissolution vessel, n=6 samples total all other dissolution parameters remained as defined in table 7.

Results Summary—Coated Mini-tablets. Based on the data obtained the following conclusions may be inferred for coated Mini-Tablets: The coating of Mini-Tablets using aqueous based EC dispersion (Surelease™) resulted in the retardation of drug release, increasing with an increase coating weight gain up to 10% weight gain. The coating of Mini-Tablets using aqueous based Polymethacrylate based dispersion (Eudragit NE30D™) was not successful following hand-painting. The coating of Mini-Tablets using a seal coat prior to aqueous based EC dispersion (Surelease™) resulted in the retardation of drug release, increasing with an increase coating weight gain. No visible signs of Mini-Tablet matrix swelling were observed following the coating of Mini-Tablets with a seal coat prior to coating with aqueous based EC dispersion (Surelease™). The mean dissolution data show uniform drug dissolution, and the profile is reliant on the integrity of the coating.

Coated Spheres

The aim was to produce coated spheres using two different cores (sugar and micro crystalline cellulose) and different coating materials (aqueous ethylcelulose, solvent based ethylcellulose and aqueous polyacrylate dispersion) with a range of dissolution profiles. Two types of spheres were considered as a drug layering substrate; soluble sugar spheres (Suglets™) and insoluble microcrystalline cellulose spheres (Vivapur™).

Sugar spheres, 1000/1180 µm in size were employed to complete the bulk of the sphere formulation development work, with the following investigations completed:
Coating of sugar spheres using non aqueous and aqueous based ethyl cellulose controlled release coating (Experiment Six);
Coating of sugar spheres using aqueous based Polyacrylate based dispersion (Eudragit E30D™) coating (Experiment Eight).

The sugar sphere data were assessed and based on the data microcrystalline cellulose spheres (710-1000 µm size) were coated using the approach that offered controlled release. This rational was adopted since the sphere is the substrate to allow drug layering and so as such has no impact on the controlled release characteristics of the drug. Therefore, microcrystalline cellulose spheres were coated using aqueous based ethyl cellulose controlled release coating only.

The sphere coating process adopted was the same for both sphere variants and all controlled release coating solutions/dispersions. It is multistage process (cf. FIG. 13). The sphere composition adopted for all formulations to achieve a drug loading of 4% w/w (10 mg per dose) is described in the table below. The controlled release coat was applied at 5% w/w layering initially, following which a sample was removed, and coating to 20% w/w weight gain was completed to a final product composition of 100% w/w. The final concentration in mg/unit is slightly lower as the film coat was not applied.

The following coating solutions/dispersions were prepared prior to the coating process:
Drug Layering Solution: 100 g solution was prepared containing 4% w/w drug and 5% w/w HPMC.
Seal Coat: 100 g dispersion was prepared containing between 3% w/w and 5% w/w coating solids as per manufacturer instructions.
Controlled Release Solution: 100 g solution was prepared containing 15% w/w coating solids (Surelease E-7-19040™), by adding 60 g of Surelease™ to 100 g with water.
Film Coat: Prepared as per seal coat.

TABLE 17

| Sphere Coating Stage | Raw Material | Concentration % w/w | Concentration mg/unit |
|---|---|---|---|
| Drug Layering | Arimoclomol | 4% w/w | 10 mg/250 mg |
| | HPMC [Methocel E6 ™] | 5% w/w | 12.5 mg/250 mg |
| Multi-particulate core | Sugar or MCC sphere | 67% w/w | 167.5 mg/250 mg |
| Seal Coat | PVA-based film coat [Opadry 200 while] | 1% w/w | 2.5 mg/250 mg |
| Controlled release coat | Ethyl cellulose/Polyacrylate [Surelease E-7-19040 ™] | 5% w/w 10% w/w 20% w/w | 12.5 mg/250 mg 25.0 mg/250 mg 50.0 mg/250 mg |
| Film Coat | PVA-based film coat [Opadry 200 white ™] | 3% w/w | 12.5 ng/250 mg |

Spheres were bottom spray coated using Mini-Glatt fitted with the Micro-Kit and Wurster Column using a 0.5 µm spray nozzle. The spheres were warmed for 10 minutes, prior to the addition of the drug layering solution to achieve a 14% w/w weight gain with a 50° C. –60° C. inlet air temperature, 0.55 bar inlet air pressure, 0.72 bar atomising air pressure and coating fluid delivery rate initially 0.42 g/min increasing to 0.94 g/min once sufficient coat was applied. Following which a seal coat was applied to achieve a 1% w/w weight gain adopting the aforementioned parameters at a comparable rate. The controlled release coat was applied to a 5% w/w weight gain, adopting the same coating parameters, a sample of spheres were removed and additional coating solution was applied to achieve a 10% w/w and 20% w/w weight gain. The final film coat was applied to spheres with 20% w/w weight gain controlled release coat adopting the same parameters described only.

Evaluation of Coated Beads: Ethyl Cellulose Based Approach. A commercially available aqueous dispersion of EC (Surelease™ E-7-19040) was used for trials rather than a solvent based approach. EC was applied to achieve a weight gain range of 5% w/w, 10% w/w and 20% w/w adopting the method described. This coating approach was adopted for sugar and MCC spheres, however, coating to 20% w/w weight gain was not completed using MCC spheres due to limited availability.

Figure 14:
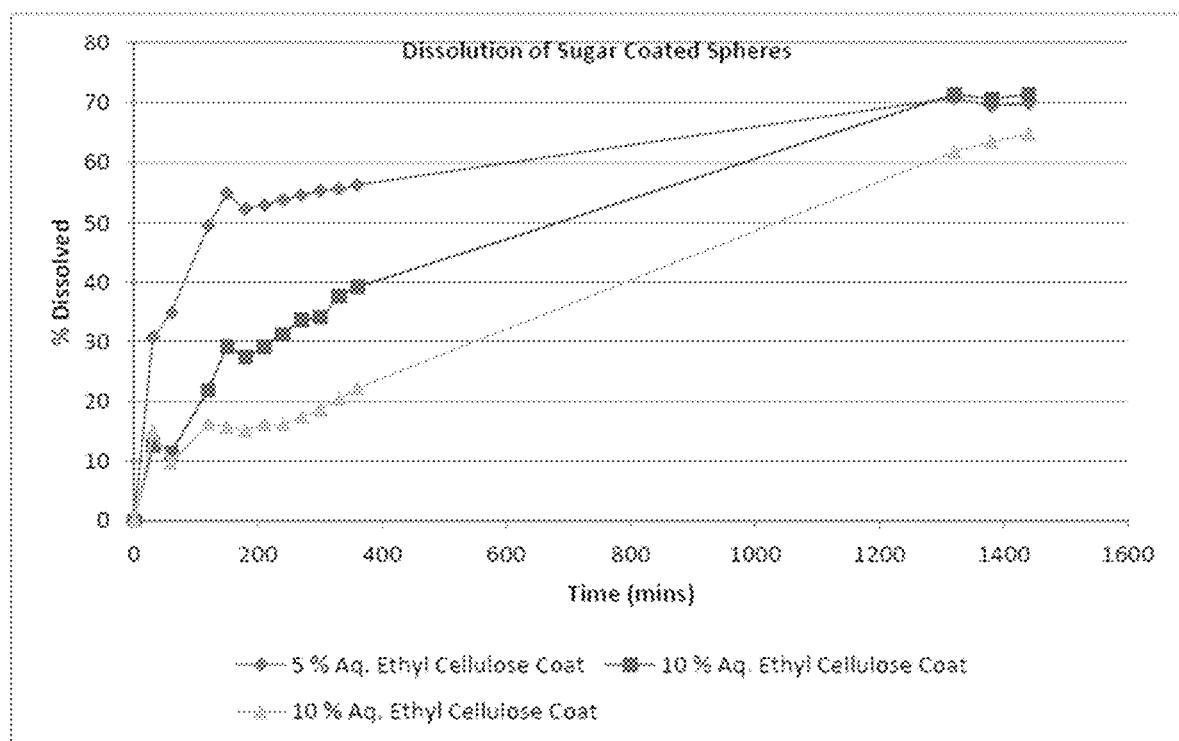
FIG. 14 Dissolution Profile of Sugar Spheres Coated with Ethyl Cellulose to 5% w/w, 10% w/w and 20% w/w Weight Gain in pH 6.8 Buffer.
Figure 15:
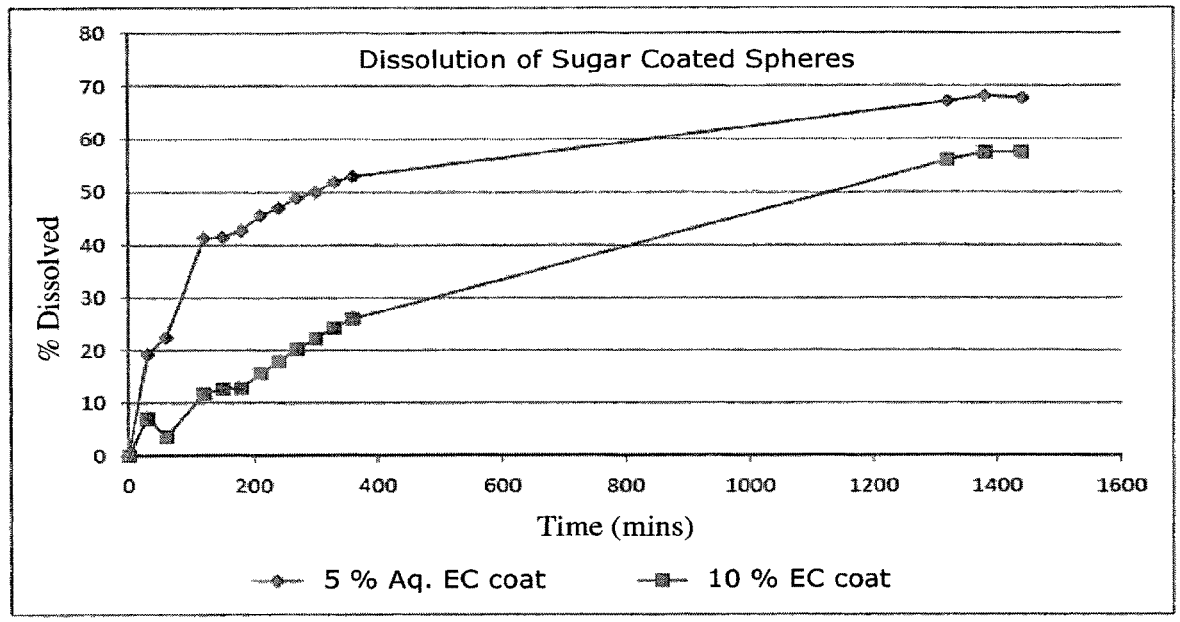
FIG. 15 Dissolution Profile of Sugar Spheres Coated with Ethyl Cellulose to 5% w/w, 10% w/w Weight Gain in 0.1M HCl Buffer.

Dissolution testing of the sugar spheres shows delayed release following the application of EC controlled release coating, with greater delay observed with increasing coating concentration (FIG. 14). This was independent on the dissolution media employed. Following coating to 5% w/w weight gain after 4 hours 53.7% of drug was released when adopting pH 6.8 buffer compared to 46.9% released when employing 0.1 M HCl (FIGS. 14 and 15).

TABLE 18

Percentage Arimoclomol Dose Dissolved (based on uncoated Assay) in pH 6.8 phosphate Buffer:

| Time | Percentage Arimicolomol Dissolved % w/w CR Coat | | |
|---|---|---|---|
| Minutes | 5 | 10 | 20 |
| 0 | 0 | 0 | 0 |
| 30 | 30.7 | 12.6 | 15 |
| 60 | 34.9 | 11.4 | 9.7 |
| 120 | 49.4 | 21.9 | 16.4 |
| 150 | 54.9 | 29.2 | 15.7 |
| 180 | 52.3 | 27.4 | 15.2 |
| 210 | 53.0 | 29.1 | 16.2 |
| 240 | 53.8 | 31.3 | 16.1 |

TABLE 18-continued

Percentage Arimoclomol Dose Dissolved (based on uncoated Assay) in pH 6.8 phosphate Buffer:

| Time | Percentage Arimicolomol Dissolved % w/w CR Coat | | |
|---|---|---|---|
| Minutes | 5 | 10 | 20 |
| 270 | 54.6 | 33.7 | 17.3 |
| 300 | 55.3 | 34.1 | 18.6 |
| 330 | 55.6 | 37.6 | 20.4 |
| 360 | 56.3 | 39.2 | 22.2 |
| 1320 | 70.8 | 71.4 | 61.8 |
| 1380 | 69.5 | 70.6 | 63.5 |
| 1440 | 69.8 | 71.4 | 64.8 |

Comparable data were obtained following coating to 10% w/w weight gain. There is no evidence of dose dumping when employing 0.1 M HCl, and based on the data obtained pH 6.8 dissolution media are to be employed for all subsequent testing. See FIG. 15.

TABLE 19

Percentage Arimoclomol Dose Dissolved (based on uncoated Assay) in 0.1M HCl:

| Time | Perecentage Arimicolomol Dissolved % w/w CR Coat | |
|---|---|---|
| Minutes | 5 | 10 |
| 0 | 0 | 0 |
| 30 | 19.3 | 7.1 |
| 60 | 22.4 | 3.6 |
| 120 | 41.3 | 11.7 |
| 150 | 41.5 | 12.7 |
| 180 | 42.7 | 12.8 |
| 210 | 45.6 | 15.6 |
| 240 | 47.0 | 17.9 |
| 270 | 48.9 | 20.2 |
| 300 | 50.0 | 22.2 |
| 330 | 51.9 | 24.3 |
| 360 | 53.0 | 26.0 |
| 1320 | 67.1 | 56.0 |
| 1380 | 68.1 | 57.5 |
| 1440 | 67.7 | 57.6 |

Delayed release of drug from the MCC spheres is also observed (FIG. 16) with greater delay with increasing thickness of controlled release coating applied between 5% w/w and 10% w/w. Following coating to 5% w/w weight gain, 56.4% drug was released after 4½ hours, with 100.4% of drug released following 23 hours. In contrast 33.5% of drug was released after 4½ hours, with 82.5% drug released observed following 23 hours (FIG. 15).

TABLE 20

Percentage Arimoclomol Dose Dissolved (based on uncoated Assay) in pH 6.8 phosphate buffer for MCC spheres:

| Time | Percentage Arimicolomol Dissolved % w/w CR Coat | | | | | |
|---|---|---|---|---|---|---|
| Minutes | 5 | 5 | 5 | 10 | 10 | 10 |
| 0 | 0 | 0 | 0 | 0 | 0 | 0 |
| 30 | 16.1 | 9.3 | 11.0 | 1.9 | 1.5 | 2.8 |
| 90 | 36.4 | 28.7 | 30.6 | 13.8 | 13.0 | 14.2 |
| 140 | 43.4 | 37.8 | 38.8 | 17.9 | 19.9 | 20.3 |
| 220 | 54.1 | 49.7 | 50.6 | 25.5 | 30.5 | 31.4 |
| 270 | 58.6 | 54.7 | 55.8 | 29.7 | 36.1 | 34.6 |
| 340 | 61.9 | 59.4 | 59.8 | 34.4 | 40.8 | 39.3 |

TABLE 20-continued

Percentage Arimoclomol Dose Dissolved (based on uncoated Assay) in pH 6.8 phosphate buffer for MCC spheres:

| Time | Percentage Arimicolomol Dissolved % w/w CR Coat | | | | | |
|---|---|---|---|---|---|---|
| Minutes | 5 | 5 | 5 | 10 | 10 | 10 |
| 1380 | 99.0 | 101.3 | 100.8 | 76.6 | 87.5 | 83.5 |
| 1620 | 98.8 | 102.4 | 101.0 | 81.2 | 93.5 | 88.3 |

Figure 16:
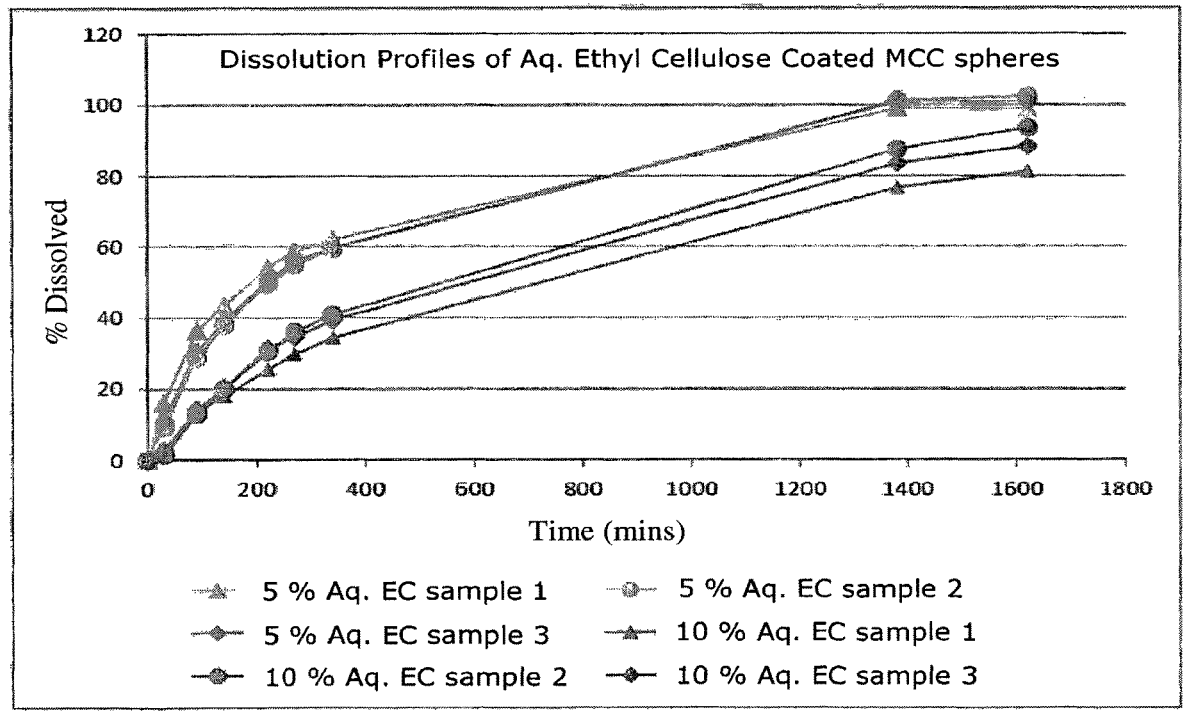
FIG. 16 Dissolution Profile of Microcrystalline Spheres Coated with Ethyl Cellulose to 5% w/w, 10% w/w Weight Gain.

See FIG. 16.

Based on the data obtained there appears to be a difference in the release rates observed when comparing sugar spheres verses MCC spheres, with MCC spheres exhibiting slower release. The MCC spheres exhibit a smaller size, 710-1000 μm compared to sugar spheres, 1000-1100 μm therefore, they possess a larger surface area thus faster release would be anticipated.

Based on the data the following conclusions may be inferred for EC controlled release coating: Sugar and microcrystalline cellulose spheres were successfully loaded with drug. Coating spheres with a 5% ethyl cellulose layer resulted in 53.8% of drug released after 4 hours for sugar spheres and 56.4% of drug release after 4½ hours for MCC spheres. Coating spheres with a 10% ethyl cellulose layer resulted in 31.3% of drug released after 4 hours for sugar spheres and 33.5% of drug release after 4½ hours for MCC spheres. The data suggest a coated sphere offer a suitable controlled release approach.

Evaluation of Coated Beads: EC/HPMC Based Approach and Poly(meth)acrylate Based Approach. Can be evaluated as presented above for the EC based approach.

Example 3: Extended Release HME-Granules of Arimoclomol

Evaluation of Hot Melt Extrusion (HME) for varying dissolution release rates for extended-release formulations for Arimoclomol.

Aim: To develop an extended release formulation of Arimoclomol in Compritol® 888 and to assess the practicalities of incorporating high contents of Arimoclomol in a Compritol® 888 matrix and producing powders of different particle sizes that may be used as either capsule or sachet fills. The investigative process will evaluate the effect of drug loading and particle size on drug dissolution profiles.

Arimoclomol/Compritol® 888 formulations of 33, 50 and 66 wt % Arimoclomol were successfully produced by hot melt extrusion and subjected to size reduction to produce discreet particle size distributions by sieving. Particles produced in this manner demonstrated no observable degradation.

Granules of the particle size ranges 710-500, 1000 710 and ≥1000 μm were subjected to dissolution testing in pH 6.8 phosphate buffer solution and demonstrated various extended release profiles of Arimoclomol. Release rates were found to be dependent on both particle size and Arimoclomol concentration.

Subsequent analysis of the particles subjected to dissolution by SEM demonstrated the formation of a porous structure, consistent with the formation of a tortuous pathway release mechanism formed by the dissolution of the Arimoclomol leaving behind a water insoluble Compritol® 888 matrix.

Production of Formulations by Hot Melt Extrusion

Arimoclomol formulations of 33, 50 and 66 wt % active in Compritol® 888 (C888) were targeted for production by hot melt extrusion using a Thermo Scientific Pharma 11 co-rotating twin screw extruder to produce solid products from Arimoclomol/C888 powder mixes.

The compositions for the HME formulations are detailed in Table 21 (Formulation compositions for 50 g batches of material to be extruded):

| Ingredient | Supplier | Lot number | Nominal content (wt %) | Weight required (g) | Weight recorded (g) |
|---|---|---|---|---|---|
| 33 wt % formulation | | | | | |
| Arimoclomol | Orphayme | 130109 | 33 | 16.5 | 16.5 |
| C888 | Gattefossé | 145245 | 67 | 33.5 | 33.5 |
| 50 wt % formulation | | | | | |
| Arimoclomol | Orphayme | 130109 | 50 | 25.0 | 25.0 |
| C888 | Gattefossé | 145245 | 50 | 25.0 | 25.0 |
| 66 wt % formulation | | | | | |
| Arimoclomol | Orphayme | 130109 | 67 | 33.5 | 33.5 |
| C888 | Gattefossé | 145245 | 33 | 16.5 | 16.5 |

A nominal feed rate of raw material to the extruder of 1.4-1.6 g/min was selected. An extrusion screw speed of 100 rpm was selected based on previous findings and literature. The heating profile of the extruder was set to the configuration detailed in

TABLE 22

(Heating configuration of the hot melt extruder for the production all extruded blends):

| Die (° C.) | Zone 7 (° C.) | Zone 6 (° C.) | Zone 5 (° C.) | Zone 4 (° C.) | Zone 3 (° C.) | Zone 2 (° C.) | Powder inlet (° C.) |
|---|---|---|---|---|---|---|---|
| 70 | 70 | 70 | 65 | 70 | 68 | 63 | 60 |

The following processing output parameters were observed for the extrusion process in all three blends:

The melt pressure was between 0-8 bar

The melt temperature was between 67-69° C.

The instrument torque was between 11-12%

All extruded dosage strengths were soft/malleable directly out of the hot melt extruder die and on cooling to room temperature presented as a white, waxy and brittle solids. Strand was collected from the extruder in various strand lengths varying from between 5 to 20 cm in length.

Strands produced via hot melt extrusion were placed into a small hand blender and subjected to 5×1 second milling pulses, interspersed by 5 second cooling periods. The ground material was then poured onto a sieve stack consisting of the following sieves: 1000 μm, 710 μm and 500 μm. These were orientated in a vertical direction with the largest sieve at the top of the stack through to the smallest sieve at the bottom of the stack. A metal collection plate was placed on the bottom sieve to collect particles below 500 μm. In orientating the sieves in the manner, the following sieve fractions were obtained: <500 μm, 710-500 μm, 1000-710 μm and ≥1000 μm. The yields of these sieve fractions are presented below in Table 23:

| Batch | Sieve fraction (μm) | Mass collected (g) | Mass collected (%) |
|---|---|---|---|
| 2154_01 | ≥1000 | 5.55 | 16.9 |
| | 1000-710 | 9.00 | 27.4 |
| | 710-500 | 5.76 | 17.5 |
| | ≤500 | 12.58 | 38.2 |
| 2154_02 | ≥1000 | 2.40 | 8.3 |
| | 1000-710 | 7.17 | 24.8 |
| | 710-500 | 5.09 | 17.6 |
| | ≤500 | 14.30 | 49.4 |
| 2154_03 | ≥1000 | 0.65 | 2.1 |
| | 1000-710 | 8.43 | 27.6 |
| | 710-500 | 5.13 | 16.8 |
| | ≤500 | 16.35 | 53.5 |

As the Arimoclomol content increased, so did the fraction of fine material (below 500 μm), accompanied by a reduction in the amount of larger material (above 1000 μm).

Assay and related substances was performed on the mid-particle size (1000-710 μm) to assess for any degradation of Arimoclomol that had occurred during processing to the granules, the results of which are included below in Table 24:

| Sample | Run 1 | Run 2 | Mean (n = 4) |
|---|---|---|---|
| 33 wt % Arimoclomol_1 | 92.31 | 94.27 | 89.9 |
| 33 wt % Arimoclomol_2 | 85.10 | 88.00 | |
| 50 wt % Arimoclomol_1 | 98.09 | 98.92 | 98.3 |
| 50 wt % Arimoclomol_2 | 97.88 | 98.47 | |
| 66 wt % Arimoclomol_1 | 101.44 | 102.16 | 101.8 |
| 66 wt % Arimoclomol_2 | 101.59 | 102.17 | |

No related substances greater than 0.05% sample area were observed in any of the samples analysed.

IR Microscopy of Granules. Infra-red (IR) microscopy was employed to characterise the surface of the granules. Averaged spectra were recorded from 5 granules for 33 wt % granules (710-500 μm), 50 wt % granules (710-500 μm) and 66 wt % granules (710-500 μm). IR spectroscopy demonstrated that in all cases, the surface of the granules is predominantly C888 suggesting good coverage of the Arimoclomol has been achieved through the hot melt extrusion process.

As the amount of Arimoclomol increased in the formulation, so does the amount of the Arimoclomol observed at the surface of the formulation as demonstrated by an increase in intensity of the relevant peak (approximately 1590 cm-1). This is consistent with a decreased covering of Arimoclomol by C888 as the Arimoclomol content increases, the consequences of which are likely to be an increase in observed dissolution rates from the water insoluble matrix.

SEM Analysis of Milled Samples Pre and Post Dissolution. Scanning electron microscopy (SEM) was performed on powdered materials pre- and post-dissolution for all three formulation strengths and for all particles size ranges of 710-500 μm, 1000-710 μm and ≥1000 μm, with the exception of the <500 μm fraction.

In all cases, these data demonstrated that milled extrudate presented predominantly as continuous undulating surface, with discreet angular particles both embedded and at the surface typically, these particles are consistent with the presence of crystalline Arimoclomol.

Scanning electron microscopy (SEM) was performed on granules after being subjected to dissolution experiments. In all cases, the angular particles (crystalline Arimoclomol) had dissolved from the surface of the granule leaving a porous water insoluble matrix.

Granules appeared to become more porous, with an increase in Arimoclomol content. This suggests that the Arimoclomol is able to dissolve away from the C888 matrix to form a tortuous pathway, leading to extended release of Arimoclomol.

Figure 17:
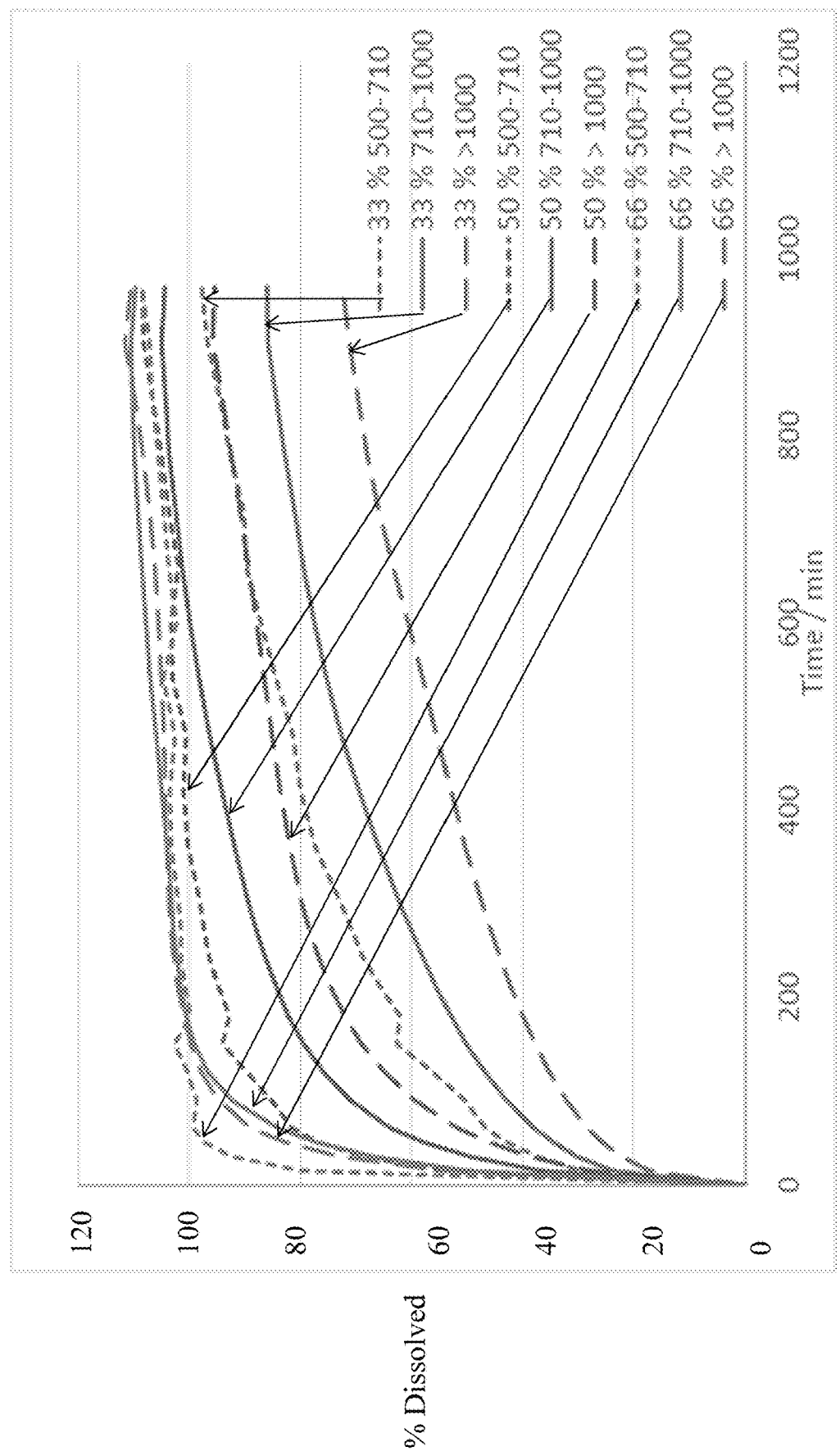
FIG. 17 Dissolution Profile of Hot melt Extrusion Granules of arimoclomol. Dissolution of 33, 50 and 66 wt % powder samples of various particle sizes in pH 6.8 phosphate buffer. Blue lines refer to 33 wt % materials, pink lines refer to 50 wt % materials and green lines refer to 66 wt % material.

Dissolution results. All granules were subjected to dissolution experiments. It was observed that the initial dissolution rate of Arimoclomol increased with increasing the Arimoclomol wt % loading with 66 wt % showing the fastest initial dissolution rate and 33 wt % showing the slowest initial dissolution rate. It can also be seen that the dissolution rate is dependent upon the particle size fraction with the 500-710 µm particle size fraction showing the fastest dissolution rate and the ≥1000 µm particle size fraction showing the slowest dissolution rate. See FIG. 17.

TABLE 25

Individual Data for particle size range of 710-500 µm:

| Time | 33% | | 50% | | 66% | |
|---|---|---|---|---|---|---|
| | % LC Arimoclomol Dissolved | | | | | |
| (mins) | V1 | V2 | V3 | V4 | V5 | V6 |
| 0 | 0.3 | 0.3 | 0.3 | 0.1 | 0.1 | 0.1 |
| 15 | 31.1 | 28.8 | 55.8 | 53.0 | 81.8 | 78.6 |
| 30 | 38.6 | 36.6 | 70.7 | 67.3 | 93.9 | 91.4 |
| 45 | 43.8 | 41.8 | 78.5 | 74.9 | 98.2 | 96.2 |
| 60 | 47.6 | 45.9 | 83.1 | 79.8 | 100.1 | 98.5 |
| 90 | 51.3 | 49.7 | 86.8 | 83.7 | 99.1 | 98.2 |
| 120 | 56.9 | 55.4 | 91.1 | 88.3 | 100.6 | 100.0 |
| 150 | 64.2 | 61.1 | 95.2 | 92.9 | 102.8 | 102.4 |
| 180 | 62.7 | 61.4 | 94.1 | 91.6 | 99.9 | 99.6 |
| 210 | 66.2 | 64.7 | 95.9 | 93.5 | 100.8 | 100.6 |
| 240 | 69.2 | 67.8 | 97.5 | 95.0 | 101.6 | 101.3 |
| 270 | 71.4 | 69.9 | 98.4 | 96.0 | 101.8 | 101.0 |
| 300 | 73.4 | 72.0 | 99.1 | 96.9 | 102.1 | 101.7 |
| 360 | 78.1 | 76.6 | 101.4 | 99.0 | 103.5 | 103.0 |
| 420 | 80.7 | 79.3 | 102.2 | 99.8 | 103.8 | 103.2 |
| 480 | 82.1 | 80.6 | 101.7 | 99.4 | 102.8 | 102.3 |
| 540 | 84.3 | 84.6 | 104.2 | 101.7 | 104.9 | 104.4 |
| 600 | 87.7 | 86.5 | 104.6 | 101.9 | 102.3 | 102.2 |
| 660 | 90.5 | 89.1 | 103.2 | 100.6 | 104.1 | 103.3 |
| 720 | 90.6 | 89.8 | 105.3 | 102.0 | 105.3 | 103.9 |
| 780 | 92.5 | 93.0 | 107.0 | 103.0 | 106.2 | 105.0 |
| 840 | 94.2 | 94.9 | 109.0 | 104.1 | 107.1 | 106.1 |
| 900 | 96.0 | 97.3 | 110.5 | 105.9 | 107.6 | 106.6 |
| 960 | 97.1 | 98.3 | 110.5 | 106.2 | 109.1 | 108.1 |

TABLE 26

Individual Data for particle size range of 1000-710 µm:

| Time | 33% | | 50% | | 66% | |
|---|---|---|---|---|---|---|
| | % LC Arimoclomol Dissolved | | | | | |
| (mins) | V1 | V2 | V3 | V4 | V5 | V6 |
| 0 | 0.1 | 0.3 | 0.1 | 0.1 | 0.4 | 0.4 |
| 15 | 22.1 | 25.6 | 42.8 | 31.3 | 56.1 | 44.2 |
| 30 | 28.8 | 31.8 | 56.8 | 42.4 | 73.0 | 60.7 |
| 45 | 32.8 | 36.0 | 65.3 | 50.1 | 82.5 | 71.7 |
| 60 | 36.4 | 39.4 | 71.6 | 55.8 | 88.5 | 79.4 |
| 90 | 41.4 | 44.5 | 78.4 | 63.6 | 95.4 | 89.4 |
| 120 | 45.4 | 48.3 | 82.6 | 69.1 | 98.4 | 94.7 |
| 150 | 49.1 | 51.3 | 85.7 | 73.2 | 100.2 | 97.9 |
| 180 | 51.6 | 54.2 | 88.1 | 76.3 | 101.2 | 99.9 |
| 210 | 54.3 | 56.7 | 89.6 | 79.0 | 101.9 | 101.0 |
| 240 | 56.4 | 58.9 | 91.2 | 81.2 | 102.4 | 101.8 |
| 270 | 58.7 | 61.1 | 92.4 | 83.3 | 103.0 | 102.6 |
| 300 | 61.0 | 63.2 | 93.7 | 85.0 | 103.1 | 103.0 |

TABLE 26-continued

Individual Data for particle size range of 1000-710 µm:

| Time | 33% | | 50% | | 66% | |
|---|---|---|---|---|---|---|
| | % LC Arimoclomol Dissolved | | | | | |
| (mins) | V1 | V2 | V3 | V4 | V5 | V6 |
| 360 | 64.8 | 67.0 | 95.7 | 88.0 | 104.0 | 103.8 |
| 420 | 68.2 | 70.6 | 97.5 | 90.8 | 105.0 | 104.9 |
| 480 | 71.3 | 73.9 | 99.5 | 93.1 | 106.1 | 105.7 |
| 540 | 73.9 | 76.7 | 101.0 | 95.4 | 107.3 | 106.7 |
| 600 | 76.0 | 78.9 | 102.4 | 97.2 | 108.0 | 107.5 |
| 660 | 78.0 | 80.9 | 103.5 | 98.9 | 108.9 | 108.2 |
| 720 | 79.5 | 82.6 | 104.5 | 100.2 | 109.6 | 108.9 |
| 780 | 81.4 | 84.3 | 105.6 | 101.6 | 110.1 | 109.5 |
| 840 | 82.9 | 85.8 | 105.9 | 102.5 | 110.4 | 109.9 |
| 900 | 84.4 | 87.4 | 106.5 | 103.4 | 110.6 | 110.3 |
| 960 | 84.5 | 87.5 | 105.6 | 103.0 | 109.4 | 109.8 |

TABLE 27

Individual Data for particle size range of ≥1000 µm:

| Time | 33% | | 50% | | 66% | |
|---|---|---|---|---|---|---|
| | % LC Arimoclomol Dissolved | | | | | |
| (mins) | V1 | V2 | V3 | V4 | V5 | v6 |
| 0 | 0.3 | -0.1 | -0.3 | -0.3 | -0.3 | -0.3 |
| 15 | 16.3 | 18.5 | 28.5 | 28.3 | 58.8 | 51.5 |
| 30 | 20.7 | 23.8 | 39.5 | 38.3 | 77.3 | 69.0 |
| 45 | 23.9 | 27.3 | 47.1 | 45.0 | 86.4 | 79.0 |
| 60 | 26.5 | 30.4 | 52.9 | 50.6 | 92.0 | 85.8 |
| 90 | 29.7 | 34.6 | 61.1 | 57.8 | 97.2 | 92.4 |
| 120 | 32.6 | 37.8 | 66.9 | 63.0 | 99.7 | 95.9 |
| 150 | 34.8 | 40.8 | 71.3 | 66.7 | 101.3 | 98.0 |
| 180 | 36.8 | 43.1 | 74.6 | 69.4 | 102.2 | 99.6 |
| 210 | 38.7 | 45.5 | 77.4 | 71.6 | 103.2 | 100.7 |
| 240 | 40.3 | 47.5 | 79.5 | 73.6 | 103.7 | 101.7 |
| 270 | 41.9 | 49.4 | 81.4 | 75.2 | 104.1 | 102.4 |
| 300 | 43.4 | 51.3 | 82.9 | 76.6 | 104.4 | 102.9 |
| 360 | 46.3 | 54.5 | 85.0 | 78.8 | 104.7 | 103.3 |
| 420 | 48.5 | 57.3 | 86.6 | 80.6 | 104.8 | 103.9 |
| 480 | 51.0 | 60.1 | 88.1 | 82.2 | 105.0 | 104.0 |
| 540 | 53.3 | 62.6 | 89.4 | 83.6 | 105.4 | 104.6 |
| 600 | 55.9 | 65.3 | 90.8 | 85.1 | 105.9 | 105.1 |
| 660 | 58.5 | 68.1 | 92.3 | 86.5 | 106.6 | 105.7 |
| 720 | 60.7 | 71.0 | 96.6 | 88.2 | 107.6 | 106.6 |
| 780 | 62.6 | 73.4 | 95.1 | 89.9 | 109.0 | 107.7 |
| 840 | 64.1 | 75.2 | 96.3 | 92.0 | 111.0 | 108.5 |
| 900 | 65.7 | 76.7 | 96.7 | 94.8 | 112.8 | 110.4 |
| 960 | 66.8 | 78.0 | 97.0 | 93.8 | 111.6 | 109.2 |

Example 4: In Vivo Testing of Controlled Release Formulation of Arimoclomol

The modified release formulation according to the present invention is tested in Göttingen male mini-pig PO PK studies with 1 test article (arimoclomol) in a 5 way cross over study: One with the current formulation and 4 modified formulations.

The in-life studies are conducted at Charles River laboratories, UK performed to non-GLP standards. Dose levels to be confirmed.

N=2 mini-pig per condition (10 mini-pigs in total), Göttingen male mini-pig. Animals are fasted prior to study. Time-points PO: 0 (pre-dose), 25 min, 45 min, 1, 2, 4, 6, 8, 12 and 24 hours (10 bleeds).

Plasma is generated by centrifugation as soon as practically possible after collection and the resultant plasma is stored at ca −80° C. until shipment to XenoGesis Ltd. on dry-ice for quantitative bioanalysis under a separate protocol.

Quantitative bioanalysis by LC-MS/MS of all plasma samples from the study are performed (100 study samples plus dose analysis as required and blanks). Plasma samples are prepared by protein precipitation. Separate accurate weighings (to 0.01 mg) of research compound for STD and QC.

Mean Cmax values and AUC can be determined using conventional methods, see e.g. Cudkowicz et al., Muscle & Nerve, July 2008, p. 837-844).

AUC, Tmax and Cmax can be determined as described e.g. in EP 2 481 400 B1.

The invention claimed is:

1. An extended-release pharmaceutical formulation in an oral dosage form comprising:
   an active pharmaceutical ingredient selected from the group consisting of: N-[2-hydroxy-3-(1-piperidinyl)-propoxy]-pyridine-1-oxide-3-carboximidoyl chloride, a stereoisomer of N-[2-hydroxy-3-(1-piperidinyl)-propoxy]-pyridine-1-oxide-3-carboximidoyl chloride, an acid addition salt of N-[2-hydroxy-3-(1-piperidinyl)-propoxy]-pyridine-1-oxide-3-carboximidoyl chloride and an addition salt of a stereoisomer of N-[2-hydroxy-3-(1-piperidinyl)-propoxy]-pyridine-1-oxide-3-carboximidoyl chloride; and
   a release-controlling excipient that provides for extended release of said active pharmaceutical ingredient,
   wherein said formulation reduces inhibition of Organic Cation Transporter 2 (OCT2), as compared to an equivalent amount of the active pharmaceutical ingredient administered by an immediate release oral dosage form and/or by bolus intravenous (IV) injection, and wherein the active pharmaceutical ingredient is present in one dosage form or formulation unit in a total amount of 5-1000 mg per dosage,
   wherein the extended-release pharmaceutical formulation provides for a Cmax of the active pharmaceutical ingredient of less than 15 µM, thereby reducing inhibition of OCT2 in the individual, and
   wherein 85% of the active pharmaceutical ingredient is released from the formulation after at least 6 hours.

2. The pharmaceutical formulation according to claim 1, wherein said formulation provides i) a Cmax of less than or equal to 10 µM, ii) a Cmax which is reduced by a factor of at least 10%, iii) a Cmax which is reduced while maintaining the active pharmaceutical ingredient exposure and/or area under the curve (AUC), iv) a Cmax which is reduced relative to the total exposure provided as expressed by the AUC, v) a Cmax lower than the half-maximal inhibition ($IC_{50}$) of the active pharmaceutical ingredient for OCT2, vi) a Tmax which is increased by a factor of at least 10-20%, vii) an inhibition of OCT2 reduced by a factor of at least 10%, and/or viii) inhibition of OCT2 reduced by maintaining Cmax lower than the half-maximal inhibition ($IC_{50}$) of the active pharmaceutical ingredient for OCT2, as compared to an equivalent amount of the active pharmaceutical ingredient administered by an immediate release oral dosage form and/or by bolus IV injection.

3. The pharmaceutical formulation according to claim 1, wherein said formulation comprises an inner matrix and at least one outer coating, said inner matrix comprising the active pharmaceutical ingredient.

4. The pharmaceutical formulation according to claim 3, wherein said formulation is selected from the group consisting of: a coated tablet, a coated mini-tablet and a coated micro-tablet.

5. The pharmaceutical formulation according to claim 1, wherein said formulation is a coated sphere comprising an inner sphere substrate and an outer coating comprising one or more individual layers, wherein said outer coating comprises the active pharmaceutical ingredient.

6. The pharmaceutical formulation according to claim 5, wherein the outer coating comprises: 1) a drug layer comprising the active pharmaceutical ingredient and 2) a controlled release coat.

7. The pharmaceutical formulation according to claim 6, wherein the outer coating further comprises one or more layers selected from the group consisting of: a seal coat and a film coat.

8. The pharmaceutical formulation according to claim 1, wherein said formulation is in the form of extended-release granules comprising: the active pharmaceutical ingredient; and a release-controlling excipient.

9. The pharmaceutical formulation according to claim 1, wherein said formulation is to be administered once daily or twice daily.

10. The pharmaceutical formulation according to claim 1, wherein said active pharmaceutical ingredient is selected from the group consisting of:
    a. the racemate of N-[2-hydroxy-3-(1-piperidinyl)-propoxy]-pyridine-1-oxide-3-carboximidoyl chloride,
    b. an optically active stereoisomer of N-[2-hydroxy-3-(1-piperidinyl)-propoxy]-pyridine-1-oxide-3-carboximidoyl chloride,
    c. an enantiomer of N-[2-hydroxy-3-(1-piperidinyl)-propoxy]-pyridine-1-oxide-3-carboximidoyl chloride,
    d. (+)-R—N-[2-hydroxy-3-(1-piperidinyl)-propoxy]-pyridine-1-oxide-3-carboximidoyl chloride,
    e. (−)-(S)—N-[2-hydroxy-3-(1-piperidinyl)-propoxy]-pyridine-1-oxide-3-carboximidoyl chloride,
    f. an acid addition salt of N-[2-hydroxy-3-(1-piperidinyl)-propoxy]-pyridine-1-oxide-3-carboximidoyl chloride,
    g. N-[2-hydroxy-3-(1-piperidinyl)-propoxy]-pyridine-1-oxide-3-carboximidoyl chloride citrate,
    h. N-[2-hydroxy-3-(1-piperidinyl)-propoxy]-pyridine-1-oxide-3-carboximidoyl chloride maleate,
    i. (+)-R—N-[2-hydroxy-3-(1-piperidinyl)-propoxy]-pyridine-1-oxide-3-carboximidoyl chloride citrate;
    j. (−)-S—N-[2-hydroxy-3-(1-piperidinyl)-propoxy]-pyridine-1-oxide-3-carboximidoyl chloride citrate;
    k. (+)-R—N-[2-hydroxy-3-(1-piperidinyl)-propoxy]-pyridine-1-oxide-3-carboximidoyl chloride maleate; and
    l. (−)-S—N-[2-hydroxy-3-(1-piperidinyl)-propoxy]-pyridine-1-oxide-3-carboximidoyl chloride maleate.

11. The pharmaceutical formulation according to claim 1, wherein said active pharmaceutical ingredient is (+)-R—N-[2-hydroxy-3-(1-piperidinyl)-propoxy]-pyridine-1-oxide-3-carboximidoyl chloride citrate.

12. An extended-release pharmaceutical formulation in an oral dosage form comprising:
    an active pharmaceutical ingredient selected from the group consisting of: N-[2-hydroxy-3-(1-piperidinyl)-propoxy]-pyridine-1-oxide-3-carboximidoyl chloride, a stereoisomer of N-[2-hydroxy-3-(1-piperidinyl)-propoxy]-pyridine-1-oxide-3-carboximidoyl chloride, an acid addition salt of N-[2-hydroxy-3-(1-piperidinyl)-propoxy]-pyridine-1-oxide-3-carboximidoyl chloride and an addition salt of a stereoisomer of N-[2-hydroxy-3-(1-piperidinyl)-propoxy]-pyridine-1-oxide-3-carboximidoyl chloride; and
    a release-controlling excipient that provides for extended release of said active pharmaceutical ingredient, wherein said formulation comprises an inner matrix and at least one outer coating, said inner matrix comprising the active pharmaceutical ingredient, and wherein 85% of the active pharmaceutical ingredient is released from the formulation after at least 6 hours.

13. The pharmaceutical formulation according to claim 12, wherein said formulation is selected from the group consisting of: a coated tablet, a coated mini-tablet and a coated micro-tablet.

14. The pharmaceutical formulation according to claim 12, wherein the outer coating comprises the active pharmaceutical ingredient.

15. The pharmaceutical formulation according to claim 12, wherein said active pharmaceutical ingredient is (+)-R—N-[2-hydroxy-3-(1-piperidinyl)-propoxy]-pyridine-1-oxide-3-carboximidoyl chloride citrate.

16. The pharmaceutical formulation according to claim 12, wherein the formulation comprises at least one type of hydroxypropylmethylcellulose.

* * * * *